(12) United States Patent
Kawakami et al.

(10) Patent No.: US 8,093,403 B2
(45) Date of Patent: Jan. 10, 2012

(54) PROCESS FOR PRODUCING FUSED IMIDAZOLE COMPOUND, REFORMATSKY REAGENT IN STABLE FORM, AND PROCESS FOR PRODUCING THE SAME

(75) Inventors: Jun-Ichi Kawakami, Yamatokoriyama (JP); Shigeru Nuwa, Kawanishi (JP); Shokyo Miki, Toyonaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 12/648,022

(22) Filed: Dec. 28, 2009

(65) Prior Publication Data

US 2010/0105922 A1 Apr. 29, 2010

Related U.S. Application Data

(62) Division of application No. 10/500,999, filed as application No. PCT/JP03/00092 on Jan. 9, 2003, now Pat. No. 7,662,974.

(30) Foreign Application Priority Data

Jan. 10, 2002 (JP) .................. 2002-003821
Sep. 25, 2002 (JP) .................. 2002-279438

(51) Int. Cl.
C07D 233/64 (2006.01)
(52) U.S. Cl. .................................. 548/341.1
(58) Field of Classification Search ............... 548/341.1
See application file for complete search history.

(56) References Cited

U.S. PATENT DOCUMENTS 5,840,961 A 11/1998 Behling et al.

FOREIGN PATENT DOCUMENTS

EP 1 193 258 A1 4/2002

OTHER PUBLICATIONS

Jaione Maiz et al, Transition Structures for the Reformatsky Reaction a Theoretical (MNDO-PM3) Study, Tetrahedron Letters, 1993, Vo. 34, No. 38, p. 6111-6114.
J. J. Chen et al., "Synthesis and Activity of Conformationally-Constrained Macrocyclic Norstatine-Based Inhibitors of HIV Protease," Bioorganic & Medicinal Chemistry Letters (1996), 6(4): 435-438; XP-002320038.
K. Soai et al., "Enantioselective Reformatsky Reaction with ketones, Asymmetric Synthesis of Beta-(tert-Hydroxy) esters," J. Chem. Soc. Chem. Commun., (193), pp. 811-812; XP002396303, 1993.
F. Orsini et al., "C-Metallated Reformatsky Intermediates. Structure and Reactivity," Tetrahedron, (1984), 40(14): 2781-2787; XP002396304.
F. Orsini et al., "Reformatsky Intermediate. A C-Metallated Species," Tetrahedron Letters, (1982), 23(38): 3945-3948; XP-02396305.
M. Gaudemar et al., "Reformatskii Reaction. Structure of a Zinc Derivative of Ethyl Bromoacetate," Comptas Rendus des Seances de l'Academie des Sciences, Sciences Chimiques, (1968), 267(17): 1053-1056; abstract only; XP-002396307.
J. S. R. Kumar et al., "Steroselective Synthesis of N-Box-Galantinic Acid Ethyl," Tetrahedron Letters, (1999), 40: 1381-1384.
M. Guademar et al., "Organic Chemistry—on the Preparation, the Structure and the Properties of Reformatsky Complexes," C. R. Acad. Sc. Paris, (1996), t. 262, pp. 213-216-Abstract.
Dekker et al., Organometallics, (1984), 3(9), pp. 1403-1407.
Jackson, R.F.W. et al, "Concise Synthesis of Enantiomerically Pure Phenylalanine, Homophenylalanine, and Bishomophenylalanine Derivatives Using Organozinc Chemistry: NMR Studies of Amino Acid-Derived Organozinc Reagents", Journal of Organic Chemistry, 63, 7875-7884, 1998.
European Search Report Application No. 10174774.9-1211/2275411 dated Jan. 20, 2011.

*Primary Examiner* — Laura L. Stockton
(74) *Attorney, Agent, or Firm* — Edwards Wildman Palmer LLP; David G. Conlin; Nicholas J. DiCeglie, Jr.

(57) ABSTRACT

The present invention provides an industrially advantageous process for producing a steroid $C_{17,20}$ lyase inhibitor represented by the general formula (I);

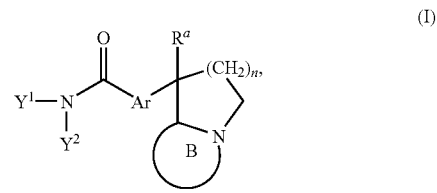

and a Reformatsky reagent in a stable form suitable for the process.

In the present invention, a compound represented by the general formula (I) is produced by reducing a specific β-hydroxy ester compound derivative or a salt thereof obtained from a specific carbonyl compound in a Reformatsky reaction in the presence of a metal hydride complex and a metal halide, and then subjecting it to a ring-closing reaction. In the above Reformatsky reaction, it is useful to use a stable solution of a compound represented by the general formula $BrZnCH_2COOC_2H_5$ or a crystal of the compound which is represented by the formula $(BrZnCH_2COOC_2H_5 \cdot THF)_2$.

18 Claims, 1 Drawing Sheet

An X-ray crystallographic structure for Reformatsky reagent (BrZnCH2COOEt THF)2

PROCESS FOR PRODUCING FUSED IMIDAZOLE COMPOUND, REFORMATSKY REAGENT IN STABLE FORM, AND PROCESS FOR PRODUCING THE SAME

CROSS REFERENCE TO RELATED APPLICATION

This application is a divisional application of U.S. patent application Ser No. 10/500,999 filed Oct. 1, 2004, which is the U.S. National Stage application under 35 U.S.C. §371 of International Patent Application Serial No. PCT/JP03/00092, filed Jan. 9, 2003, which claims the benefit of Japanese Patent Application No. 2002-279438, filed Sep. 25, 2002, and Japanese Patent Application No. 2002-3821 filed Jan. 10, 2002; the disclosures of each of which are expressly incorporated by reference in their entireties.

FIELD OF THE INVENTION

The present invention relates to a fused imidazole compound useful as a steroid $C_{17,20}$ lyase inhibitor, and to an industrially advantageous process for producing an intermediate thereof.

In addition, the present invention relates to a Reformatsky reagent in a stable form and to a process for producing such a Reformatsky reagent at a high reproducibility. More specifically, the Reformatsky reagent according to the present invention includes a stable solution of the Reformatsky reagent and a crystal thereof.

BACKGROUND OF THE INVENTION

Prior Art

Androgen and estrogen, which are sex hormones, have various physiological activities such as cell differentiation, cell proliferation and the like. On the other hand, it has been understood that androgen and estrogen act as a provocation factor in certain diseases. It is known that a steroid $C_{17,20}$ lyase involves in a final stage of an in vivo biosynthesis of androgen. More specifically, a steroid $C_{17,20}$ lyase produces dehydroepiandrosterone and androstendione from 17-hydoxypregnenolone and 17-hyodroxyprogesterone as substrates, which are derived from cholesterols. Therefore, a drug inhibiting a steroid $C_{17,20}$ lyase suppresses production of androgen and production of estrogen produced from androgen as a substrate, and is useful as a pharmaceutical compound preventing or treating diseases in which androgen or estrogen is a provocation factor. Examples of the diseases in which androgen or estrogen is a provocation factor include, but limited to, prostate cancer, prostatemegaly, virilization, hypertrichosis, male pattern baldness, male precocious puberty, breast cancer, uterine cancer, ovarian cancer, mastopathy, myometrisis, endmetriosis, adenomyosis uteri, polycystic ovary syndrome, and the like.

A compound represented by the following general formula (Iz):

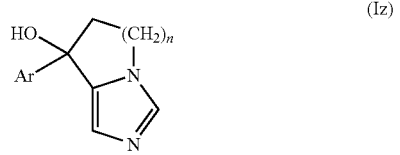

wherein n is an integer of 1 to 3, Ar is an aromatic ring which may have a substituent, and a salt thereof are highly safe, and are useful as an excellent steroid $C_{17,20}$ lyase inhibitor. Especially, useful is the compound represented by the general formula (Iz) wherein Ar is a substituent represented by the following general formula:

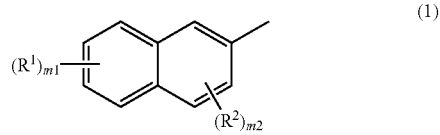

wherein m1 is an integer of 1 to 4, m2 is an integer of 0 to 3, $R^1$ and $R^2$ are, the same or different and independently, a hydrogen atom, a hydroxy group which may have a substituent, a thiol group which may have a substituent, an amino group which may have a substituent, an acyl group, a halogen atom, or a hydrocarbon group which may have a substituent; a substituent represented by the following general formula:

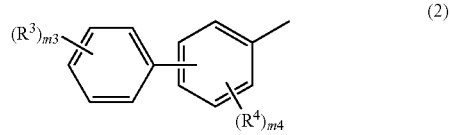

wherein m3 is an integer of 1 to 5, m4 is an integer of 0 to 4, $R^3$ and $R^4$ are, the same or different and independently, a hydrogen atom, a hydroxy group which may have a substituent, a thiol group which may have a substituent, an amino group which may have a substituent, an acyl group, a halogen atom, or a hydrocarbon group which may have a substituent; or a substituent represented by the following general formula:

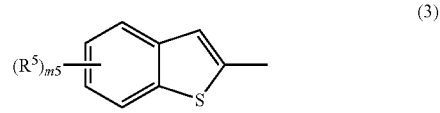

wherein m5 is an integer of 1 to 4, $R^5$ is a hydrogen atom, a hydroxy group which may have a substituent, a thiol group which may have a substituent, an amino group which may have a substituent, an acyl group, a halogen atom, or a hydrocarbon group which may have a substituent, and wherein either of (1) $R^1$ or $R^2$, (2) $R^3$ or $R^4$, or (3) $R^5$ is a substituted or unsubstituted amide group.

As a process for reducing carboxylic acid ester into alcohol by using sodium borohydride, the following techniques have been known in the art: (1) a process comprising reducing an ester with tetrahydrofuran or alcohol in the presence of sodium borohydride and calcium chloride (*Nature*, 1955, 175, 346; *Org. Pro. Res. & Develp.*, 2001, 5, 122-126; JP-A 2000-239202), (2) a process comprising adding dropwise methanol to a solution of ester in t-butanol (*Synthetic Com.*, 1982, 12, 463-467; Yuki Goseikagaku (*Organic Synthesis Chemistry*), 1987, 45, 1148), (3) a process comprising reducing an ester with tetrahydrofuran in the presence of sodium borohydride, zinc chloride and tertiary amine, and the like.

The Reformatsky reaction is a useful reaction in synthesizing β-hydroxy acid and its derivatives, and is reviewed in *Organic Reactions*, 1975, 22, 423; *Synthesis*, 1989, 571; *Angew. Chem., Int. Ed.*, 1993, 32, 164; *Aldrichimica Acta*, 2000, 33, 52 and the like.

According to the Reformatsky reaction, α-bromoester may be reacted with a carbonyl compound such as aldehyde and ketone in the presence of zinc metal to form β-hydroxy ester, which is then hydrolyzed to form a corresponding β-hydroxy acid. Upon adequately selecting ester or carbonyl compound as a starting material, a wide variety of complicated β-hydroxy ester and β-hydroxy acid can be produced.

Moreover, the Reformatsky reaction is aggressively applied to a field of asymmetric syntheses in recent years. Therefore, it goes without saying that the Reformatsky reaction becomes more useful in the near future.

As a reagent used in the Reformatsky reaction (Reformatsky reagent), ethyl bromozincacetate obtained by reacting zinc with ethyl bromoacetate is well known. In particular, a preparation of ethyl bromozincacetate is described in detail in *Monatshefte für Chemie*, 1953, 910; *J. Org. Chem.*, 1987, 52, 4796; *Organometallics*, 1984, 3, 1403; *Bull. Soc. Chim. Fr.*, 1969, 2471 and the like.

REFERENCES

1: JP-A 2000-239202
2: JP-A 302287/1999
3: *Nature*, 1955, 175, 346
4: *Org. Pro. Res. & Develp.*, 2001, 5, 122-126
5: *Synthetic Com.*, 1982, 12, 463-467
6: Yuki Goseikagaku (*Organic Synthesis Chemistry*), 1987, 45, 1148
7: *Organic Reactions*, 1975, 22, 423
8: *Synthesis*, 1989, 571
9: *Angew. Chem., Int. Ed.*, 1993, 32, 164
10: *Aldrichimica Acta*, 2000, 33, 52
11: *J. Org. Chem.*, 1987, 52, 4796
12: *Organometallics*, 1984, 3, 1403
13: *Bull. Soc. Chim. Fr.*, 1969, 2471
14: *Encyclopedia of Reagents for Organic Synthesis*, 1995, 2402
15: *J. Chem. Soc., Chem. Commun.*, 1983, 553
16: *J. Am. Chem. Soc.*, 1943, 65, 239
17: *J. Med. Chem.*, 1977, 20, 721
18: *Monatshefte für Chemie*, 1953, 910
19: *Tetrahedron Lett.*, 1982, 3945
20: *Tetrahedron*, 1984, 2787

The Problems to be Solved by the Invention

To date, a process has not been developed, which industrially satisfies production of a compound represented by the general formula (I), and there is a need to early develop the steroid $C_{17,20}$ lyase inhibitor represented by the general formula (I) as a useful pharmaceuticals. Thus, an object of the present invention is to provide a steroid $C_{17,20}$ lyase inhibitor and a process which is industrially advantageous for producing an intermediate of the above inhibitor.

Further, the present inventors made a detailed research on the prior art to obtain ethyl bromozincacetate which is most common among Reformatsky reagents.

For example, *Bull. Soc. Chim. Fr.*, 1969, 2471 describes that a reaction in synthesizing a Reformatsky reagent proceeds quantitatively under the conditions where absolute methylal which is free of alcohol is used as a solvent and a reaction temperature is maintained at 40° C. or above. Although methylal is considered as a preferable solvent in the article, it is not industrially preferable from the following reasons: methylal is unstable under acidic conditions; extremely pure methylal is required; methylal decomposes to form formaldehyde which is highly reactive and is considered as a cancer-causing substance; and the like. In addition, this article describes that a yield of an ethyl bromozincacetate derivative is low when it is prepared in tetrahydrofuran.

*Monatshefte für Chemie*, 1953, 910 describes a use of diethyl ether which is industrially disadvantageous, and a step for adding methylmagnesium iodide to a mixture of bromoacetate and zinc and heating it. However, since such a process probably causes bumping, scaling-up is very difficult. In many other reports other than relatively recent ones, Reformatsky reagents are prepared by using methylal or diethyl ether under the similar conditions.

Then, the present inventors tried to prepare ethyl bromozincacetate according to the procedures described in the above references by using tetrahydrofuran which is common in preparing Grignard reagents. However, ethyl bromozincacetate could not be reproducibly prepared because the reaction did not initiate or initiated steeply, or yielding was extremely low. Low reproducibility in initiating reactions and steep initiation of reaction are unpleasant in industry processes.

It is generally reported that good preparation results are obtained by cleaning zinc prior to a Reformatsky reaction or a synthesis of a Reformatsky reagent. In the present inventor's work, industrial preferable reproducibility could not be obtained even when zinc was cleaned.

From the above results, it is recognized that a reproducible and industrially advantageous process for producing a Reformatsky reagent is required and the resulting Reformatsky reagent is required to have stability sufficient to stand practical use.

In this context, *Encyclopedia of Reagents for Organic Synthesis*, 1995, 2402 describes that ethyl bromozincacetate presented for a few days in diethyl ether at low temperatures.

*Tetrahedron Lett.*, 1982, 3945 and *Tetrahedron*, 1984, 2787 report that tert-butyl bromozincacetate could be isolated as a crystal, but ethyl bromozincacetate could not be crystallized.

In addition, *J. Chem. Soc., Chem. Commun.*, 1983, 553 and *Organometallics*, 1984, 3, 1403 report that a tert-butyl bromozincacetate-THF binuclear complex $(BrZnCH_2COOtBu.THF)_2$ could be isolated as a crystal, but ethyl bromozincacetate could not be crystallized.

In this context, since reaction products obtained from ethyl bromozincacetate and carbonyl compounds and the like are different from those obtained from tert-butyl bromozincacetate in steric hindrance and stability, it is understood that they may exhibit different reactivities each other in the subsequent derivation reactions.

SUMMARY OF THE INVENTION

The present inventors have made every effort to study a process for producing a compound represented by the general formula (I) to find that surprisingly carboxylic acid ester can be selectively reduced without side effect occurrence by using a metal hydride complex and a metal halide compound. Consequently, the present invention has been accomplished based on the above findings.

More specifically, the present invention relates to (1) A process for producing a compound represented by the general formula (II'):

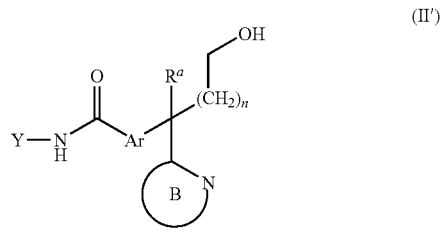

wherein R is an ester residue, $R^a$ is a hydrogen atom or a substituent, Ar is an aromatic hydrocarbon group which may have a substituent, Y is a hydrogen atom or a substituent, a ring B is a nitrogen-containing ring which may have a substituent, n is an integer of 1 to 3 or a salt thereof, which comprises reducing a compound represented by the general formula (III'):

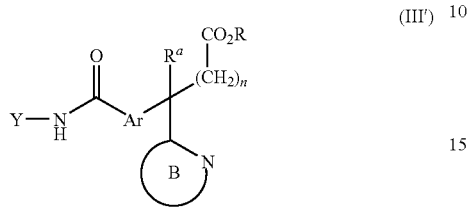

wherein each symbol is defined, above or a salt thereof;

(2) A process for producing a compound represented by the general formula (II):

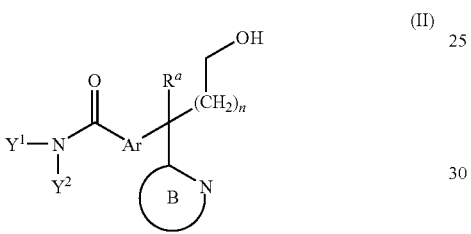

wherein R is an ester residue, $R^a$ is a hydrogen atom or a substituent, Ar is an aromatic hydrocarbon group which may have a substituent, $Y^1$ and $Y^2$ are, the same or different and independently, a hydrogen atom or a substituent, a ring B is a nitrogen-containing ring which may have a substituent, n is an integer of 1 to 3 or a salt thereof, which comprises reducing in the presence of a metal hydride complex and a metal halide compound a compound represented by the general formula (III):

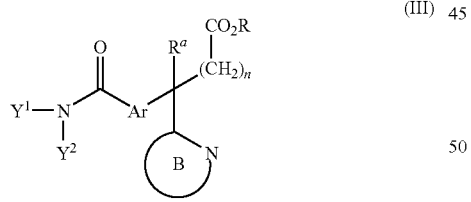

wherein each symbol is defined above or a salt thereof;

(3) A process for producing a compound represented by the general formula (I):

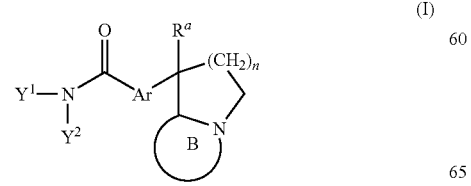

wherein R is an ester residue, $R^a$ is a hydrogen atom or a substituent, Ar is an aromatic hydrocarbon group which may have a substituent, $Y^1$ and $Y^2$ are, the same or different and independently, a hydrogen atom or a substituent, a ring B is a nitrogen-containing ring which may have a substituent, n is an integer of 1 to 3 or a salt thereof, which comprises obtaining a compound represented by the general formula (II):

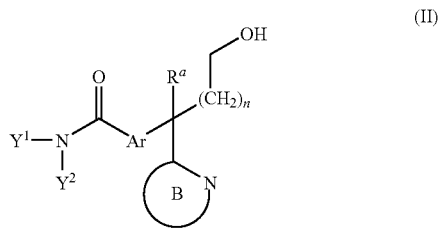

wherein each symbol is defined above or a salt thereof by reducing a compound represented by the general formula (III):

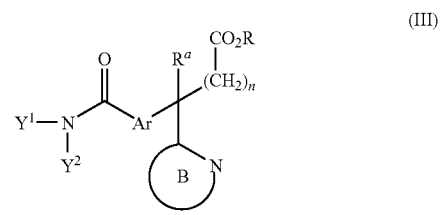

wherein each symbol is defined above or a salt thereof in the presence of a metal hydride complex and a metal halide compound, and then subjecting the compound represented by the general formula (II) to a ring-closing reaction;

(4) The process according to any one of (1) to (3), wherein the ring B is a heterocyclic ring which may have a substituent and one to three heteroatoms arbitrarily selected from a nitrogen atom, a sulfur atom and an oxygen atom other than the nitrogen atom indicated in the formula;

(5) A process for producing a compound represented by the general formula (IIa):

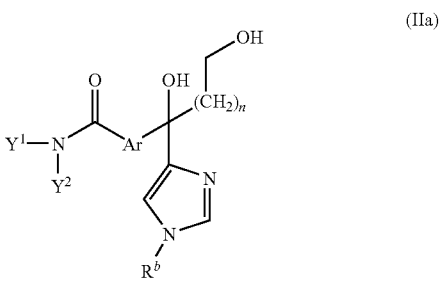

wherein R is an ester residue, Ar is an aromatic hydrocarbon group which may have a substituent, $Y^1$ and $Y^2$ are, the same or different and independently, a hydrogen atom or a substituent, $R^b$ is a protection group, n is an integer of 1 to 3 or a salt thereof, which comprises reducing a compound represented by the general formula

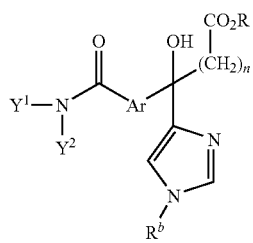

wherein each symbol is defined above or a salt thereof in the presence of a metal hydride complex and a metal halide compound;

(6) A process for producing a compound represented by the general formula (Ia):

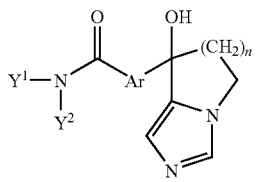

wherein R is an ester residue, Ar is an aromatic hydrocarbon group which may have a substituent, $Y^1$ and $Y^2$ are, the same or different and independently, a hydrogen atom or a substituent, $R^b$ is a protection group, n is an integer of 1 to 3 or a salt thereof, which comprises obtaining a compound represented by the general formula (IIa):

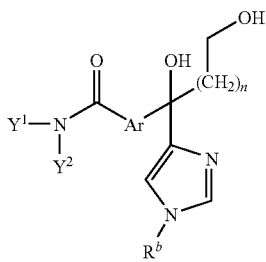

wherein each symbol is defined above or a salt thereof by reducing a compound represented by the general formula (IIIa):

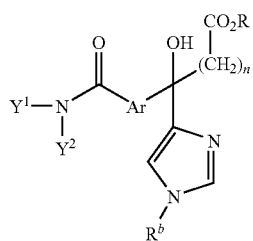

wherein each symbol is defined above or a salt thereof in the presence of a metal hydride complex and a metal halide compound, and then subjecting the compound represented by the general formula (IIa) to a ring-closing reaction;

(7) A process for producing a compound represented by the general formula (IIb):

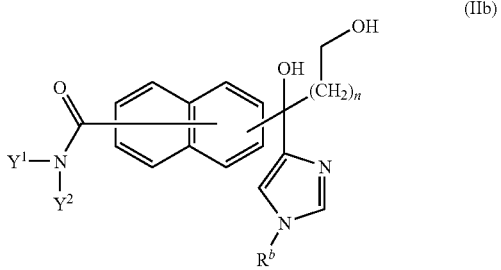

wherein R is an ester residue, $Y^1$ and $Y^2$ are, the same or different and independently, a hydrogen atom or a substituent, $R^b$ is a protection group, n is an integer of 1 to 3 or a salt thereof, which comprises reducing a compound represented by the general formula (IIIb):

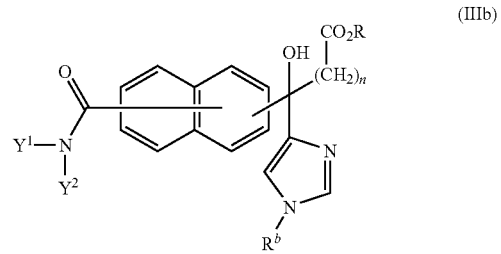

wherein each symbol is defined above or a salt thereof in the presence of a metal hydride complex and a metal halide compound;

(8) A process for producing a compound represented by the general formula (Ib):

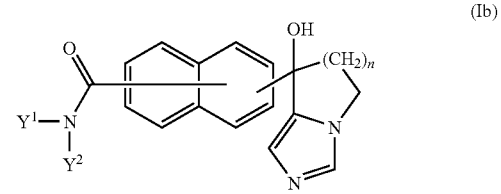

wherein R is an ester residue, $Y^1$ and $Y^2$ are, the same or different and independently, a hydrogen atom or a substituent, $R^b$ is a protection group, n is an integer of 1 to 3 or a salt thereof, which comprises obtaining a compound represented by the general formula (IIb):

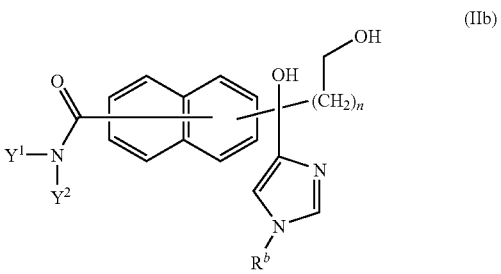

wherein each symbol is defined above or a salt thereof by reducing a compound represented by the general formula (IIIb):

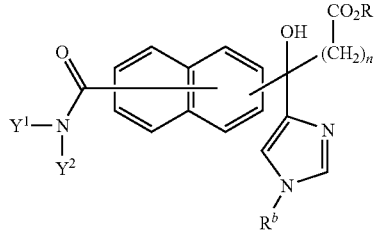

wherein each symbol is defined above or a salt thereof in the presence of a metal hydride complex and a metal halide compound, and then subjecting the compound represented by the general formula (IIb) to a ring-closing reaction;

(9) A process for producing a compound represented by the general formula (IIc):

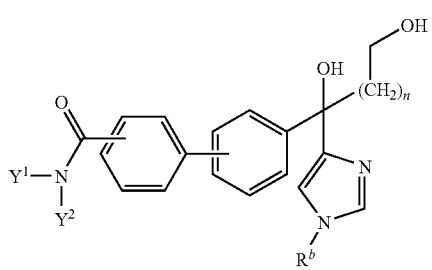

wherein R is an ester residue, $Y^1$ and $Y^2$ are, the same or different and independently, a hydrogen atom or a substituent, $R^b$ is a protection group, n is an integer of 1 to 3 or a salt thereof, which comprises reducing a compound represented by the general formula (IIIc):

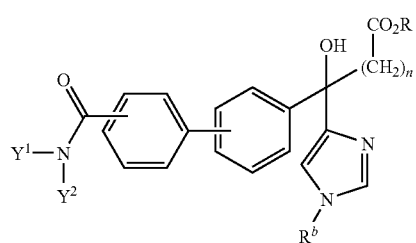

wherein each symbol is defined above or a salt thereof in the presence of a metal hydride complex and a metal halide compound;

(10) A process for producing a compound represented by the general formula (Ic)

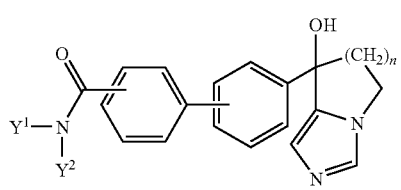

wherein R is an ester residue, $Y^1$ and $Y^2$ are, the same or different and independently, a hydrogen atom or a substituent, $R^b$ is a protection group, n is an integer of 1 to 3 or a salt thereof, which comprises obtaining a compound represented by the general formula (IIc):

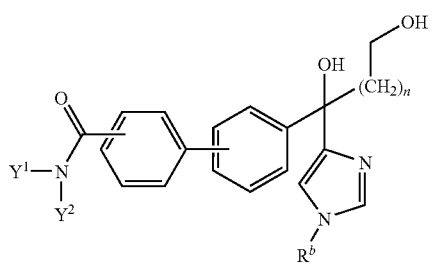

wherein each symbol is defined above or a salt thereof by reducing a compound represented by the general formula (IIIc):

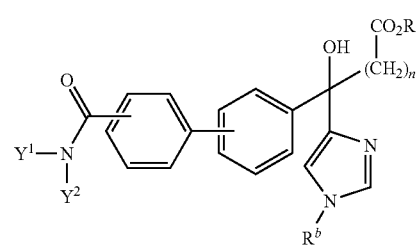

wherein each symbol is defined above or a salt thereof in the presence of a metal hydride complex and a metal halide compound, and then subjecting the compound represented by the general formula (IIc) to a ring-closing reaction;

(11) A process for producing a compound represented by the general formula (IId):

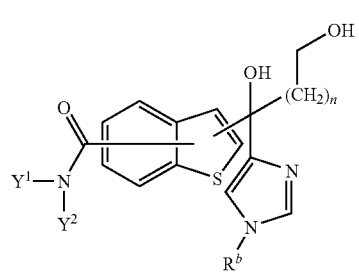

wherein R is an ester residue, $Y^1$ and $Y^2$ are, the same or different and independently, a hydrogen atom or a substituent, $R^b$ is a protection group, n is an integer of 1 to 3 or a salt thereof, which comprises reducing a compound represented by the general formula (IIId):

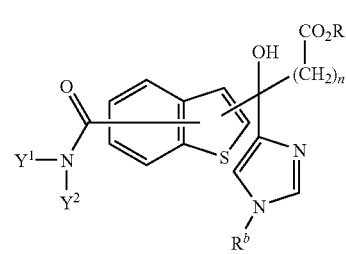

wherein each symbol is defined above or a salt thereof in the presence of a metal hydride complex and a metal halide compound;

(12) A process for producing a compound represented by the general formula (Id):

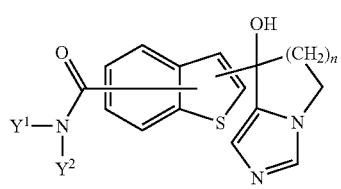

wherein R is an-ester-residue, $Y^1$ and $Y^2$ are, the same or different and independently, a hydrogen atom or a substituent, $R^b$ is a protection group, n is an integer of 1 to 3 or a salt thereof, which comprises obtaining a compound represented by the general formula (IId):

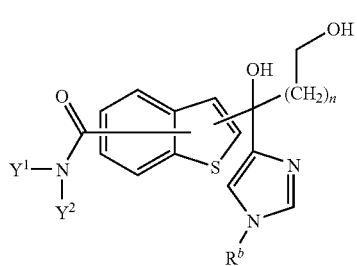

wherein each symbol is defined above or a salt thereof by reducing a compound represented by the general formula (IIId):

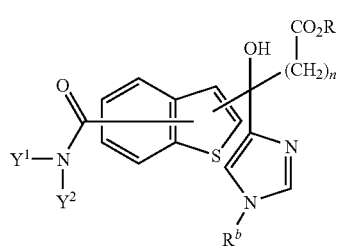

wherein each symbol is defined above or a salt thereof in the presence of a metal hydride complex and a metal halide compound, and then subjecting the compound represented by the general formula (IId) to a ring-closing reaction;

(13) The process according to any one of (1) to (12), wherein Y, $Y^1$ and R are aliphatic hydrocarbon groups;

(14) The process according to any one of (1) to (13), wherein the metal hydride complex is an alkali metal hydride complex;

(15) The process according to (14), wherein the alkali metal hydride complex is sodium borohydride;

(16) The process according to any one of (1) to (13), wherein the metal halide is a calcium halide;

(17) The process according to (16), wherein the calcium halide is calcium chloride;

(18) The process according to (1) or (2), wherein ether and alcohol are used as solvent in a reduction reaction;

(19) The process according to (18), which comprises adding alcohol to a reaction system in ether as a solvent;

(20) The process according to (18) or (19), wherein the ether is a cyclic ether and the alcohol is $C_{1-6}$ alcohol;

(21) The process according to (20), wherein the cyclic ether is tetrahydrofuran and the $C_{1-6}$ alcohol is ethanol or methanol;

(22) A process for producing a primary alcohol, which comprises selectively reducing (i) an esterified carboxyl group and (ii) an esterified carboxy group of a compound having an N-unsubstituted amido group or an N-monosubstituted amido group in an ether-alcohol solvent in the presence of metal hydride complex and a calcium halide;

(23) The process according to (22), which comprises adding alcohol to a reaction system in ether as a solvent;

(24) The process according to (22), wherein the metal hydride complex is an alkali metal hydride complex;

(25) The process according to (22), wherein the calcium halide is calcium chloride; and

(26) The process according to (22), wherein the metal hydride complex is sodium borohydride, the calcium halide is calcium chloride, the ether is tetrahydrofuran and the alcohol is ethanol or methanol.

Further, the present invention relates to

(27) A crystal of ethyl bromozincacetate to which tetrahydrofuran (THF) coordinates;

(28) The crystal of the compound according to (27), wherein a decrease in titer is less than 20%, preferably less than 10%, and more preferably less than 5% two months after its production;

(29) The crystal of the compound according to (27), which is represented by a formula $(BrZnCH_2COOC_2H_5 \cdot THF)_2$;

(30) The crystal of the compound according to (27), which has peaks at 2983, 2897, 1589, 1446, 1371, 1286, 1070, 1022, 858 and 769 ($cm^{-1}$) by IR;

(31) The crystal of the compound according to (27), which has a structure determined by an X-ray crystallography:

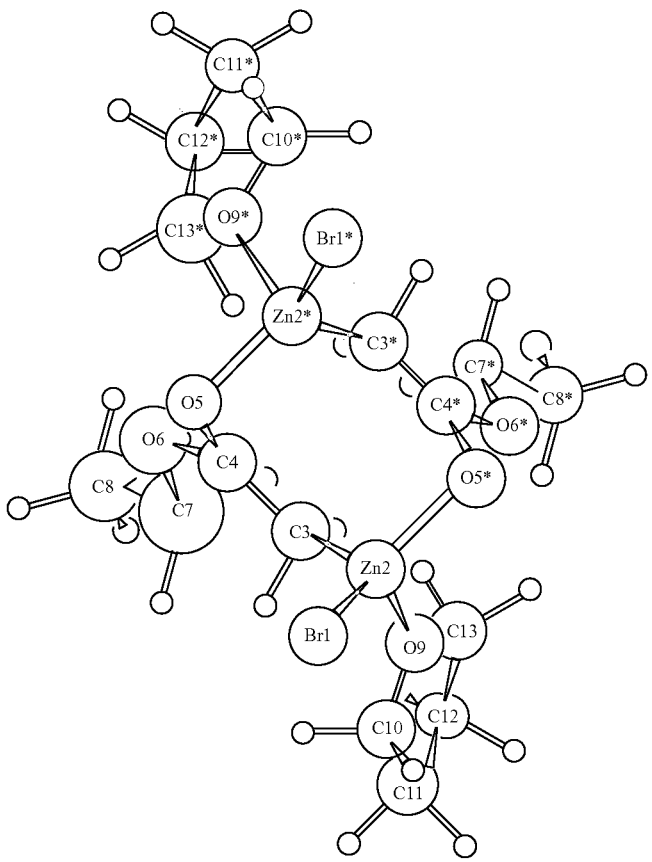

wherein the bond length of Br(1)-Zn(2) is 2.334 Å, the bond length of Zn(2)-C(3) is 1.996 Å, the bond length of Zn(2)-O(5) is 2.029 Å, the bond length of Zn(2)-O(9) is 2.049 Å, the bond length of C(3)-C(4) is 1.21 Å, the bond length of C(4)-O(5) is 1.47 Å, the bond length of C(4)-O(6) is 1.33 Å, the bond length of O(6)-C(7) is 1.46 Å, the bond length of C(7)-C(8) is 1.41 Å, the bond length of O(9)-C(10) is 1.42 Å, the bond length of C(9)-C(13) is 1.42 Å, the bond length of C(10)-C(11) is 1.49 Å, the bond length of C(11)-C(12) is 1.37 Å, and the bond length of C(12)-C(13) is 1.42 Å; and the bond angle of Br(1)-Zn(2)-C(3) is 112.4°, the bond angle of Br(1)-Zn(2)-O(5) is 122.5°, the bond angle of Br(1)-Zn(2)-O(9) is 105.0°, the bond angle of C(3)-Zn(2)-O(5) is 109.9°, the bond angle of C(3)-Zn(2)-O(9) is 91.3°, the bond angle of O(5)-Zn(2)-O(9) is 111.2°, the bond angle of Zn(2)-C(3)-C(4) is 129.6°, the bond angle of C(3)-C(4)-O(5) is 125°, the bond angle of C(3)-C(4)-O(6) is 120.6°, the bond angle of O(5)-C(4)-O(6) is 113°, the bond angle of Zn(2)-O(5)-C(4) is 108.1°, the bond angle of C(4)-O(6)-C(7) is 116°, the bond angle of O(6)-C(7)-C(8) is 111°, the bond angle of Zn(2)-O(9)-C(10) is 122.6°, the bond angle of Zn(2)-O(9)-C(13) is 122.8°, the bond angle of C(10)-O(9)-C(13) is 109.7°, the bond angle of O(9)-C(10)-C(11) is 104°, the bond angle of C(10)-C(11)-C(12) is 108°, the bond angle of C(11)-C(12)-C(13) is 109°, and the bond angle of O(9)-C(13)-C(12) is 106°;

(32) A process for producing a crystal of a compound represented by a formula $(BrZnCH_2COOC_2H_5 \cdot THF)_2$, which comprises reacting a compound represented by a formula $BrZnCH_2COOC_2H_5$ and tetrahydrofuran (THF);

(33) The process according to (32), which comprises dissolving a compound represented by a formula $BrZnCH_2COOC_2H_5$ in tetrahydrofuran (THF), and forming a crystal of the compound represented by a formula $(BrZnCH_2COOC_2H_5 \cdot THF)_2$;

(34) The process according to (32), which comprises dissolving a compound represented by a formula $BrZnCH_2COOC_2H_5$ in 1,2-dimethoxyethane or cyclopentyl methyl ether, adding tetrahydrofuran (THF) to the resulting solution, and forming a crystal of the compound represented by a formula $(BrZnCH_2COOC_2H_5 \cdot THF)_2$;

(35) The process according to (32), which comprises reacting the compound represented by a formula $BrCH_2COOC_2H_5$ and an excess amount of zinc relative to the compound represented by a formula $BrCH_2COOC_2H_5$ in a solvent selected from a group consisting of 2-methyltetrahydrofuran, 1,2-dimethoxyethane and cyclopentyl methyl ether or a mixed solvent in any combination of two or more of them in the presence of an activating agent, adding THF to the resulting solution, and forming a crystal of the compound represented by a formula $(BrZnCH_2COOC_2H_5 \cdot THF)_2$;

(36) A crystal of a compound obtained by the process according to (32);

(37) A process for producing a compound represented by the general formula (V):

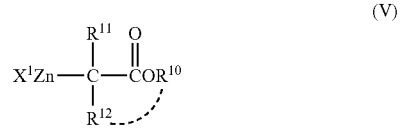

wherein $X^1$ is a bromine atom or an iodine atom; and $R^{11}$ and $R^{12}$ are, the same or different and independently, a hydrogen atom, an aliphatic hydrocarbon group which may have a substituent, an alicyclic hydrocarbon group which may have a substituent, a heterocyclic group which may have a substituent, an aromatic hydrocarbon group which may have a substituent, an aromatic heterocyclic group which may have a substituent, and $R^{10}$ is an ester residue; or $R^{11}$ is a hydrogen atom, an aliphatic hydrocarbon group which may have a substituent, an alicyclic hydrocarbon group which may have a substituent, a heterocyclic group which may have a substituent, an aromatic hydrocarbon group which may have a substituent, an aromatic heterocyclic group which may have a substituent, and $R^{10}$ and $R^{12}$, taken together with the atom to which they are bonded, form a lactone ring which may have a substituent, which comprises reacting a compound represented by the general formula (IV):

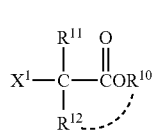

(IV)

wherein $X^1$, $R^{10}$, $R^{11}$ and $R^{12}$ are the same as defined above with zinc in a solvent selected from a group consisting of 2-methyltetrahydrofuran, 1,2-dimethoxyethane, cyclopentyl methyl ether and tetrahydrofuran, or in a mixed solvent in any combination of two or more of them in the presence of an activating agent, wherein zinc exists in an excess amount relative to the compound represented by the general formula (IV);

(38) The process according to (37), wherein zinc exists in an amount more than 1 gram atom and 50 gram atoms or less relative to one mole amount of the compound represented by the general formula (IV);

(39) The process according to (37), wherein $R^{10}$ is a methyl group or an ethyl group;

(40) The process according to (37), wherein the solvent is cyclopentyl methyl ether;

(41) The process according to (37), wherein the solvent is tetarahydrofuran;

(42) The process according to (37), wherein the activating agent is selected from halogen, copper halide, silver halide, 1,2-dihalogenethane, halogen alkylsilane and molecular sieves, wherein halogen is chloride, bromide or iodide;

(43) The process according to (42), wherein the activating agent is halogen alkylsilane;

(44) The process according to (43), wherein the activating agent is chlorotrimethylsilane;

(45) A solution of a compound represented by the general formula (V):

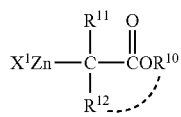

(V)

wherein $X^1$ is a bromine atom or an iodine atom; and $R^{11}$ and $R^{12}$ are, the same or different and independently, a hydrogen atom, an aliphatic hydrocarbon group which may have a substituent, an alicyclic hydrocarbon group which may have a substituent, a heterocyclic group which may have a substituent, an aromatic hydrocarbon group which may have a substituent, an aromatic heterocyclic group which may have a substituent, and $R^{10}$ is an ester residue; or $R^{11}$ is a hydrogen atom, an aliphatic hydrocarbon group which may have a substituent, an alicyclic hydrocarbon group which may have a substituent, a heterocyclic group which may have a substituent, an aromatic hydrocarbon group which may have a substituent, an aromatic heterocyclic group which may have a substituent, and $R^{10}$ and $R^{12}$, taken together with the atom to which they are bonded, form a lactone ring which may have a substituent, in 1,2-dimethoxyethane or cyclopentyl methyl ether;

(46) A solution of ethyl bromozincacetate in 1,2-dimethoxyethane or cyclopentyl methyl ether;

(47) A process for stabilizing a compound represented by the general formula (V):

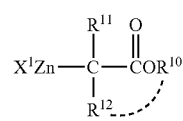

(V)

wherein $X^1$ is a bromine atom or an iodine atom; and $R^{11}$ and $R^{12}$ are, the same or different and independently, a hydrogen atom, an aliphatic hydrocarbon group which may have a substituent, an alicyclic hydrocarbon group which may have a substituent, a heterocyclic group which may have a substituent, an aromatic hydrocarbon group which may have a substituent, an aromatic heterocyclic group which may have a substituent, and $R^{10}$ is an ester residue; or $R^{11}$ is a hydrogen atom, an aliphatic hydrocarbon group which may have a substituent, an alicyclic hydrocarbon group which may have a substituent, a heterocyclic group which may have a substituent, an aromatic hydrocarbon group which may have a substituent, an aromatic heterocyclic group which may have a substituent, and $R^{10}$ and $R^{12}$, taken together with the atom to which they are bonded, form a lactone ring which may have a substituent, by using 1,2-dimethoxyethane or cyclopentyl methyl ether; and

(48) Use of a crystal of the compound according to (27) in a step of producing a compound by a Reformatsky reaction, and the like.

DETAILED DESCRIPTION OF THE INVENTION

Figure 1:
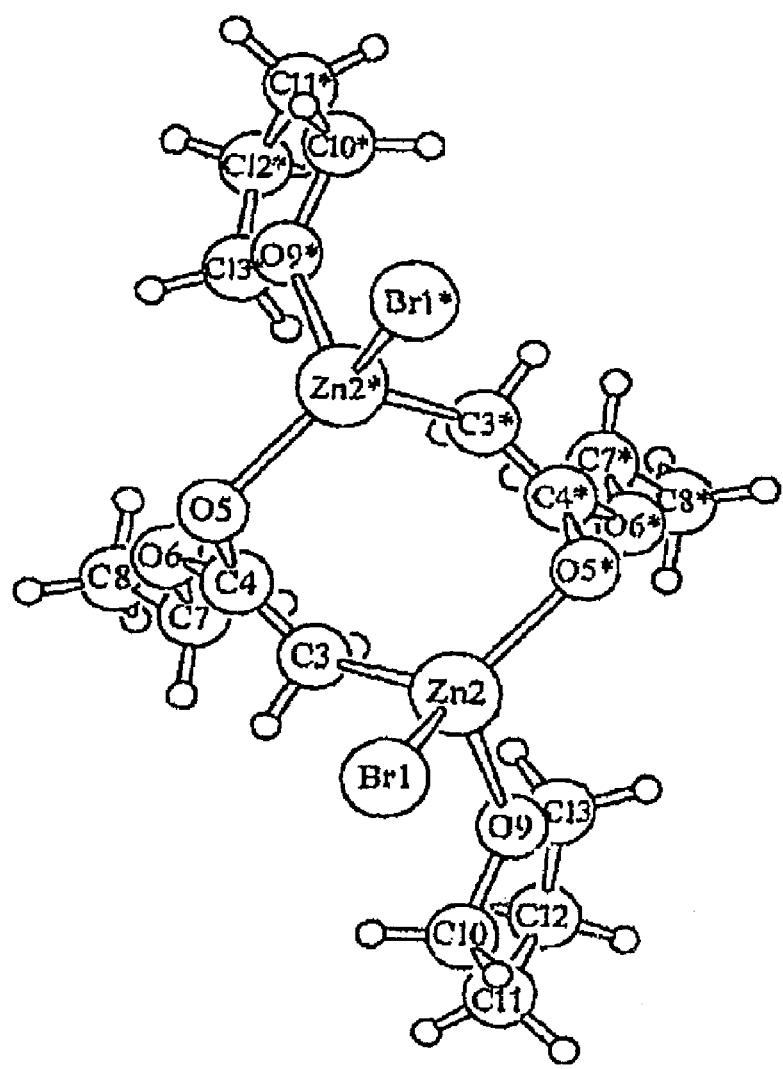
FIG. 1 illustrates an X-ray crystal structure for a crystal of a Reformatsky reagent according to the present invention $((BrZnCH_2COOC_2H_5.THF)_2)$.
Figure 1:

The present invention will be explained in detail below.

For the ester residue represented by R, any residue generally used in organic syntheses may be used without any limitation as far as forming a carboxylic acid or an ester. For example, a substituted or unsubstituted $C_{1\sim8}$ alkyl such as methyl, ethyl, iodoethyl, propyl, isopropyl, butyl, isobutyl, methanesulfonylethyl, trichloroethyl, t-butyl and the like; $C_{2\sim8}$ alkoxyalkyl such as methoxymethyl, methoxyethyl, methylthioethyl and the like; $C_{4\sim8}$ 2-oxacycloalkyl such as tetrahydropyranyl, tetrahydrofuranyl and the like; $C_{3\sim8}$ alkenyl such as propenyl, allyl, prenyl, hexenyl, phenylpropenyl, dimethylhexenyl and the like; $C_{6\sim12}$ aryl such as phenyl, tolyl, diisopropylphenyl, xylyl, trichlorophenyl, pentachlorophenyl, indanyl and the like; $C_{7\sim19}$ aralkyl such as benzyl, methylbenzyl, dimethylbenzyl, methoxybenzyl, ethoxybenzyl, nitrobenzyl, aminobienzyl, diphenylmethyl, phenylethyl, trityl, di-t-butylhydroxybenzyl, phthalidyl, phenacyl and the like; $C_{2\sim15}$ alkanoyloxyalkyl such as acetoxymethyl, acetoxyethyl, propionyloxymethyl, pivaloyloxymethyl, pivaloyloxyethyl, cyclohexaneacetoxyethyl, cyclohexanecarbonyloxycyclohexylmethyl and the like; $C_{3\sim15}$ alkoxycarbonyloxy alkyl such as ethoxycarbonyloxyethyl, isopropoxycarbonyloxyethyl, isopropoxycarbonyloxypropyl, t-butoxycarbonyloxyethyl, isopentyloxycarbonyloxypropyl, cyclohexyloxycarbonyloxyethyl, cyclohexylmethoxycarobonyloxyethyl, bornyloxycarbonyloxyisopropyl and the like; and the like may be used. Preferably, $C_{1\sim8}$ alkyl is used.

For the aromatic hydrocarbon group in "the aromatic hydrocarbon group which may have a substituent" represented by Ar, monocyclic or fused polycyclic aromatic hydrocarbon groups and the like are used, and a $C_{6\sim14}$ aromatic hydrocarbon group is preferably used. Specifically, for example, a $C_{6\sim14}$ aromatic hydrocarbon group such as phenyl, naphthyl anthryl, azulenyl, phenanthryl, phenalenyl, fluorenyl, indacenyl, biphenylenylhaptalenyl, acenaphthylenyl and the like are preferable. Preferably, phenyl, naphthyl, anthryl are used, and more preferably, benzene, 1-naphthyl, 2-naphthyl and the like are used.

The nitrogen-containing ring in "the nitrogen-containing ring which may have a substituent" represented by a ring B means a ring having at least one nitrogen atom as an atom constituting the ring (an atom on the ring). The ring may contain one to three kinds of heteroatoms arbitrarily selected from an oxygen atom, a sulfur atom, a nitrogen atom and the like other than carbon atoms.

Specifically, examples of the nitrogen-containing ring include a 5- or 6-membered monocyclic nitrogen-containing ring such as pyrrole, pyrroline, pyrrolidine, imidazolidine, imidazoline, thiazolidine, oxazolidine, pyrazoline, pyrazolidine, piperidine, piperazine, morpholine, oxazole, isoxazole, thiazole, isothiazole, 1,2-imidazole, 1,3-imidazole, pyrazole, 1,2,3-oxadiazole, 1,2,4-oxadiazole, 1,3,4-oxadiazole, furazan, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine, triazine and the like; and a 8- to 12-membered fused polycyclic nitrogen-containing ring such as indoline, isoindoline, 1H-indazole, benzindazole, benzoxazole, 1,2-benzisoxazole, benzothiazole, 1,2-benzisothiazole, 1H-benzotriazole, quinoline, isoquinoline, cinnoline, quinazoline, quinoxaline, phthalazine, naphthilizine, purine, pteridine, carbazole, α-carboline, β-carboline, γ-carboline, acridine, phenoxazine, phenothiazine, phenazine, phenanthridine, phenanthroline, indolizine, pyrrolo[1,2-b]pylidazine, pyrazolo[1,5-a]pyridine, imidazo[1,2-a]pyridine, imidazo[1,5-a]pyridine, imidazo[1,2-b]pyridazine, imidazo[1,2-a]pyrimidine, 1,2,4-triazolo[4,3-a]pyridine, 1,2,4-triazolo[4,3-b]pyridazine and the like may be used. Preferably, a 5- or 6-membered monocyclic nitrogen-containing ring.

For the aliphatic hydrocarbon group represented by Y, $Y^1$ and R, for example, an aliphatic chain hydrocarbon group and an alicyclic hydrocarbon group and the like may be used.

Examples of the aliphatic chain hydrocarbon group representing an aliphatic hydrocarbon include a linear- or branched-chain aliphatic hydrocarbon such as an alkyl group, an alkenyl group, an alkynyl group and the like.

The alkyl group used in the present invention includes, for example, a $C_{1\sim10}$ alkyl group such as methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl, 2-ethylbutyl, n-heptyl, 1-methyheptyl, 1-ethylhexyl, n-octyl, 1-methylheptyl, nonyl and the like. Preferably, a $C_{1\sim6}$ alkyl group is used.

The alkenyl group used in the present invention includes, for example, a $C_{2\sim6}$ alkenyl group such as vinyl, allyl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl and the like.

The alkynyl group used in the present invention includes, for example, a $C_{2\sim6}$ alkynyl group such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like.

Examples of the alicyclic hydrocarbon group representing an aliphatic hydrocarbon include a saturated or unsaturated alicyclic hydrocarbon group such as a cycloalkyl group, a cycloalkenyl group, a cycloalkanedienyl group and the like.

The cycloalkyl group used in the present invention includes, for example, a $C_{3\sim9}$ cycloalkyl group such as cyclopropyl, cyclobutyl, cyclopentyl, cyclohexyl, cycloheptyl, cyclooctyl, cyclononyl and the like.

The cycloalkenyl group used in the present invention includes, for example, a $C_{3\sim6}$ cycloalkenyl group such as 2-cyclopenten-1-yl, 3-cyclopenten-1-yl, 2-cyclohexen-1-yl, 3-cyclohexen-1-yl, 1-cyclobuten-1-yl, 1-cyclopenten-1-yl and the like.

The cycloalkanedienyl group used in the present invention includes, for example, a $C_{4\sim6}$ cycloalkanedienyl group such as 2,4-cyclopentanedien-1-yl, 2,4-cyclohexanedien-1-yl, 2,5-cyclohexanedien-1-yl and the like.

The substituent from the aromatic hydrocarbon group which may have a substituent represented by Ar and the substituent from the nitrogen-containing ring which may have a substituent represented by the ring B are the same or different, and may be protected by a conventional organic synthesize method, and they are not limited in any manner as far as they do not affect a reaction. Examples of the substituent include (i) an alkyl group which may be substituted; (ii) an alkenyl group which may be substituted; (iii) an alkynyl group which may be substituted; (iv) an aryl group which may be substituted; (v) an aralkyl group which may be substituted; (vi) a cycloalkyl group which may be substituted; (vii) a cycloalkenyl group which may be substituted; (viii) a heterocyclic group which may be substituted; (ix) an amino group which may be substituted; (x) an imidoyl group (e.g., a group represented by a formula —C(U')=N—U, wherein U and U' are a hydrogen atom or a substituent. Preferably, U is a hydrogen atom.); (xi) an amidino group which may be substituted (e.g., a group represented by a formula —C(NT'T")=N-T, wherein T, T' and T" are a hydrogen atom or a substituent. Preferably, T is a hydrogen atom); (xii) a hydroxy group which may be substituted; (xiii) a thiol group which may be substituted; (xiv) an alkylsulfinyl group; (xv) a, carboxylic group which may be esterified or amidated; (xvi) a thiocarbamoyl group which may be substituted; (xvii) a sulfamoyl group which may be substituted; (xviii) a halogen atom (e.g., fluorine, chlorine, bromine, iodine and the like. Chlorine, bromine and the like are preferable.); (xix) a cyano group; (xx) an isocyano group; (xxi) a cyanato group; (xxii) an isocyanato group; (xxiii) a thiocyanato group; (xxiv) an isothiocyanato group; (xxv) a nitro group; (xxvi) a nitroso group; (xxvii) an acyl group from sulfonic acid; (xxviii) an acyl group from carboxylic acid; (xxix) an oxo group; and the like. Any of these substituents may have one to five, preferably one to three substituents at positions capable of being substituted.

For the alkyl group in "the alkyl group which may be substituted" as the substituent, for example, $C_{1-6}$ alkyl such as methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl and the like may be used. The substituent of the alkyl group used in the present invention includes, for example, a lower alkoxyl group (e.g., $C_{1-6}$ alkoxy such as methoxy, ethoxy, propoxy and the like), a halogen atom (e.g., fluorine, chlorine, bromine, iodine and the like), a lower alkyl group (e.g., $C_{1-6}$ alkyl such as methyl, ethyl, propyl and the like), a lower alkenyl group (e.g., $C_{2-6}$ alkenyl such as vinyl, allyl and the like), a lower alkynyl group (e.g., $C_{2-6}$ alkynyl such as ethynyl, propargyl and the like), an amino group which may be substituted, a hydroxy group which may be substituted, a cyano group, an amidino group which may be substituted, a carboxyl group, a lower alkoxycarbonyl group (e.g., $C_{1-6}$ alkoxycarbonyl such as methoxycarbonyl, ethoxycarbonyl and the like), a carbamoyl group which may be substituted (e.g., a carbamoyl group which may be substituted with a $C_{1-6}$ alkyl group or an acyl group which may be substituted with a 5- to 6-membered monocyclic aromatic heterocyclic group such as pyridinyl and the like (e.g., formyl, $C_{2-6}$ alkanoyl, benzoyl, $C_{1-6}$ alkoxycarbonyl which may be halogenated, $C_{1-6}$ alkylsulfonyl which may be halogenated, benzenesulfonyl and the like), 1-azetidinylcarbonyl, 1-pyrrolidinylcarbonyl, piperidinocarbonyl, morpholinocarbonyl, 1-piperazinylcarbonyl and the like). Any of these substituents may have one to three substituents at positions capable of being substituted.

For "the amino group which may be substituted", "the hydroxy group which may be substituted", and "the amidino group which may be substituted" as a substituent for "the alkyl group which may be substituted", a group similar to "the amino group which may be substituted", "the hydroxy group which may be substituted", and "the amidino group which may be substituted" as a substituent for "the aromatic homocyclic or heterocyclic group which may be substituted" which will be mentioned below may be used.

For the alkenyl group, in "the alkenyl group which may be substituted" as the above substituent, for example, $C_{2-6}$ alkenyl such as vinyl, allyl, isopropenyl, 2-methyl allyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl and the like may be used. For the substituent in the alkenyl group, a group similar to a substituent in "the alkyl group which may be substituted" as the above substituent may be used at a similar number.

For the alkynyl group in "the alkynyl group which may be substituted" as the above substituent, for example, $C_{2-6}$ alkynyl such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like may be used. For the substituent in the alkynyl group, a group similar to a substituent in "the alkyl group which may be substituted" as the above substituent may be used at a similar number.

For the aryl group in "the aryl group which may be substituted" as the above substituent, for example, $C_{6-14}$ aryl such as phenyl, naphthyl, anthryl, phenanthryl, acenaphthyrenyl and the like may be used. For the substituent in the aryl group, a group similar to a substituent in "the alkyl group which may be substituted" as the above substituent may be used at a similar number.

For the aralkyl group in "the aralkyl group which may be substituted" as the above substituent, for example, $C_{7-11}$ aralkyl such as benzyl, phenethyl, naphthylmethyl and the like may be used. For the substituent in the aralkyl group, a group similar to a substituent in "the alkyl group which may be substituted" as the above substituent may be used at a similar number.

For the cycloalkyl group in "the cycloalkyl group which may be substituted" as the above substituent, for example, $C_{3-7}$ cycloalkyl such as cyclopropyl, cyclobutyl, cyclopentyl, cyclohexyl, cycloheptyl and the like may be used. For the substituent in "the cycloalkyl group", a group similar to the substituent in "the alkyl group which may be substituted" as the above substituent may be used at a similar number.

For the cycloalkenyl group in "the cycloalkenyl group which may be substituted" as the above substituent, for example, $C_{3-7}$ cycloalkenyl such as cyclopropenyl, cyclobutenyl, cyclopentenyl, cyclohexenyl and the like. For the substituent in the cycloalkenyl group, a group similar to the substituent in "the alkyl group which may be substituted" as the above substituent may be used at a similar number.

For the heterocyclic group in "the heterocyclic group which may be substituted" as the above substituent, for example, an aromatic heterocyclic group, a saturated or unsaturated non-aromatic heterocyclic group (an aliphatic heterocyclic group) and the like having one to three kinds (pareferably one to two kinds) of at least one (preferably one to four, and more preferably one to two) heteroatoms arbitrarily selected from an oxygen atom, a sulfur atom, a nitrogen atom and the like as an atom constituting the ring (an atom on the ring); may be used.

For "the aromatic heterocyclic group", a 5- or 6-membered monocyclic aromatic heterocyclic group such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like; and a 8- to 12-membered fused polycyclic aromatic heterocyclic group such as benzofuranyl, isobenzofuranyl, benzo[b]thienyl, indolyl, isoindolyl, 1H-indazolyl, benzindazolyl, benzoxazolyl, 1,2-benzisoxazolyl, benzothiazolyl, benzopyranyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl and the like (preferably, a heterocyclic group in which the above 5- or 6-membered monocyclic aromatic heterocyclic groups is fused with a benzene ring or a heterocyclic group in which two heterocyclic rings of the same or different ones from the above 5- or 6-membered monocyclic aromatic heterocyclic group are fused, more preferably, a heterocyclic group in which the above 5- or 6-membered monocyclic aromatic heterocyclic group is fused with a benzene ring, and most preferably, benzofuranyl, benzopyranyl, benzo[b]thienyl and the like) may be used.

For "the non-aromatic heterocyclic group", a 3- to 8-membered (preferably, a 5- to 6-membered) saturated or unsaturated (preferably saturated) non-aromatic heterocyclic group (an aliphatic heterocyclic group) such as oxiranyl, azetidinyl, oxetanyl, thietanyl, pyrrolidinyl, tetrahydrofuryl, thioranyl, piperidyl, tetrahydropyranyl, morpholinyl, thiomorpholinyl, piperazinyl and the like; or a non-aromatic heterocyclic group in which a part or all of double bonds in the above monocyclic aromatic heterocyclic group or fused polycyclic aromatic heterocyclic group are saturated, such as 1,2,3,4-tetrahydroquinolyl, 1,2,3,4-tetrahydroisoquinolyl and the like may be used.

For the substituent in "the heterocyclic group which may be substituted" as the substituted, a lower alkyl group (e.g., $C_{1\sim6}$ alkyl such as methyl, ethyl, propyl and the like), a lower alkenyl group (e.g., $C_{2\sim6}$ alkenyl such as vinyl, allyl and the like), a lower alkynyl group (e.g., $C_{2\sim6}$ alkynyl such as ethynyl, propargyl and the like), an acyl group (e.g., $C_{1\sim6}$ alkanoyl such as formyl, acetyl, propionyl, pivaloyl and the like; benzoyl and the like), an amino group which may be substituted, a hydroxy group which may be substituted, a halogen atom (e.g., fluorine, chlorine, bromine, iodine and the like, preferably chlorine, bromine and the like), an imidoyl group which may be substituted, an amidino group which may be substituted and the like may be used. Any of these substituents may have one to five, preferably one to three substituents at positions capable of being substituted.

For "the amino group which may be substituted", "the hydroxy group which may be substituted", "the imidoyl group which may be substituted", and "the amidino group which may be substituted" in "the heterocyclic group which may be substituted" as the above substituent, a group similar to "the amino group which may be substituted", "the hydroxy group which may be substituted", "the imidoyl group which may be substituted", and "the amidino group which may be substituted" as the substituent in an aromatic allocyclic or heterocyclic group which may be substituted" which will be mentioned below may be used.

For the substituent in "the amino group which may be substituted", "the imidoyl group which may be substituted", "the amidino group which may be substituted", "the hydroxy group which may be substituted", and "the thiol group which may be substituted" as the above substituent, for example, a halogen atom (e.g., fluorine, chlorine, bromine, iodine and the like); $C_{1\sim6}$ alkoxy which may be halogenated (e.g., methoxy, ethoxy, trifluoromethoxy, 2,2,2-trifluoroethoxy, trichloromethoxy, 2,2,2-trichloroethoxy and the like); and a lower alkyl group (e.g., $C_{1\sim6}$ alkyl such as methyl, ethyl, propyl, isopropyl, butyl, isobutyl, tert-butyl, pentyl, hexyl and the like) which may be substituted with a substituent selected from a $C_{7\sim11}$ alkylaryl group (e.g., o-tolyl, m-tolyl, p-tolyl, xylyl, mesityl and the like, preferably, $C_{1\sim5}$ alkylphenyl and the like); an acyl group ($C_{1\sim6}$ alkanoyl (e.g., formyl, acetyl, propionyl, pivaloyl and the like), benzoyl, $C_{1\sim6}$ alkylsulfonyl (e.g., methanesulfonyl and the like), benzenesulfonyl and the like); a $C_{1\sim6}$ alkoxycarbonyl group which may be halogenated (e.g., methoxycarbonyl, ethoxycarbonyl, trifluoromethoxycarbonyl, 2,2,2-trifluoroethoxycarbonyl, trichloromethoxycarbonyl, 2,2,2-trichloroethoxycarbonyl and the like), a $C_{1\sim6}$ alkoxycarbonyl group which may be substituted with a phenyl group (e.g., benzyloxycarbonyl and the like); aryl ($C_{6\sim10}$ aryl such as phenyl, 1-naphthyl, 2-naphthyl and the like); aralkyl (e.g., $C_{7\sim10}$ aralkyl such as benzyl, phenethyl and the like, preferably phenyl-$C_{1\sim4}$ alkyl and the like); arylalkenyl (e.g., $C_{8\sim10}$ arylalkenyl such as cinnamyl and the like, preferably phenyl-$C_{2\sim4}$ alkenyl and the like); a heterocyclic group (a group similar to the heterocyclic group in "the heterocyclic group which may be substituted" as the above substituent, preferably pyridyl, and more preferably 4-pyridyl and the like); and the like may be used. Any of these substituents may have one to three substituents at positions capable of being substituted.

The amino group in "the amino group which may be substituted" as the above substituent may be substituted with an imidoyl group which may be substituted (e.g., $C_{1\sim6}$ alkylimidoyl (e.g., formylimidoyl, acetylimidoyl and the like), $C_{1\sim6}$ alkoxyimidoyl, $C_{1\sim6}$ alkylthioimidoyl, amidino and the like); an amino group which may be substituted with 1-2 $C_{1\sim6}$ alkyl groups. Any of these substituents may have one to two substituents at positions capable of being substituted. In addition, two substituents, taken together with a nitrogen atom, may form a cyclic amino group. Such a cyclic amino group may be, for example, a 3- to 8-membered (preferably a 5- or 6-membered) cyclic amino group such as 1-azetidinyl; 1-pyrrolidinyl; piperidino; thiomorpholino; morpholine; 1-piperazinyl; 1-piperazinyl, 1-pyrrolyl, 1-imidazolyl and the like which may have a lower alkyl (e.g., $C_{1\sim6}$ alkyl such as methyl, ethyl, propyl, isopropyl, butyl, tert-butyl, pentyl, hexyl and the like), aralkyl (e.g., $C_{7\sim10}$ aralkyl such as benzyl, phenethyl and the like), aryl (e.g., $C_{6\sim10}$ aryl such as phenyl, 1-naphthyl, 2-naphthyl and the like) at its forth position; and the like.

For the alkylsulfinyl group in "the alkylsulfinyl group which may be substituted" as the above substituent, $C_{1\sim6}$ alkylsulfinyl such as methylsulfinyl, ethylsulfinyl, propylsulfinyl, isopropylsulfinyl, butylsulfinyl, isobutylsulfinyl, sec-butylsulfinyl, tert-butylsulfinyl, pentylsulfinyl, hexylsulfinyl and the like may be used. For the substituent in the alkylsulfinyl, a group similar to the substituent in "the alkyl group which may be substituted" as the above substituent may be used at a similar number.

For "the carboxyl group which may be esterified or amidated" as the above substituent, a carboxyl group, alkoxycarbonyl, aryloxycarbonyl, aralkyloxycarbonyl, carbamoyl, N-monosubstituted carbamoyl and N,N-disubstituted carbamoyl may be used.

For the alkoxycarbonyl, for example, $C_{1\sim6}$ alkoxycarbonyl (lower alkoxycarbonyl) such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl and the like may be used. Among them, $C_{1\sim3}$ alkoxycarbonyl such as methoxycarbonyl, ethoxycarbonyl, propoxycarbonyl and the like are preferably used. The above lower alkoxycarbonyl may have a substituent, and for the substituent, a hydroxyl group; an amino group which may be substituted (the amino group may have one or two substituents such as a lower alkyl group (e.g., $C_{1\sim6}$ alkyl such as methyl, ethyl, propyl, isopropyl, butyl, isobutyl, tert-butyl, pentyl, hexyl and the like, preferably methyl, ethyl and the like) which may be substituted with one to five halogen atoms (e.g., fluorine, chlorine, bromine, iodine and the like); an acyl group (e.g., $C_{1\sim6}$ alkanoyl such as formyl, acetyl, propionyl, pivaloyl and the like; benzoyl and the like), a carboxyl group, $C_{1\sim6}$ alkoxycarbonyl and the like); a halogen atom (e.g., fluorine, chlorine, bromine, iodine and the like); a nitro group; a cyano group; a lower alkoxyl group (e.g., $C_{1\sim6}$ alkoxy such as methoxy, ethoxy, n-propoxy, isopropoxy, n-butoxy, isobutoxy, sec-butoxy, tert-butoxy and the like, preferably methoxy, ethoxy and the like) which may be substituted with one to five halogen atoms (e.g., fluorine, chlorine, bromine, iodine and the like) may be used. Preferably, one, two or three (preferably one or two) of these substituents are substituted with the same or different substituents.

For the aryloxycarbonyl, for example, $C_{6\sim14}$ aryloxycarbonyl such as phenoxycarbonyl, 1-naphthoxycarbonyl, 2-naphthoxycarbonyl, 1-phananthoxycarbonyl and the like are preferably used. The aryloxycarbonyl may have a substituent, and for the substituent, a group similar to the substituent in the alkoxycarbonyl as the above substituent may be used at a similar number.

For the aralkyloxycarbonyl, for example, $C_{7\sim14}$ aralkyloxycarbonyl (preferably, $C_{6\sim10}$ alkoxy-carbonyl and the like) such as benzyloxycarbonyl, phenethyloxycarbonyl and the like are preferably used. The aralkyloxycarbonyl may have a substituent, and for the substituent, a group similar to the substituent in the alkoxycarbonyl as the above substituent may be used at a similar number.

For the N-monosubstituted carbamoyl, for example, a lower alkyl (e.g., $C_{1\sim6}$ alkyl such as methyl, ethyl, propyl, isopropyl, butyl, isobutyl, tert-butyl, pentyl, hexyl and the like); a lower alkenyl (e.g., $C_{2\sim6}$ alkenyl such as vinyl, allyl, isopropenyl, propenyl, butenyl, pentenyl, hexenyl and the like); cycloalkyl (e.g., $C_{3\sim6}$ cycloalkyl such as cyclopropyl, cyclobutyl, cyclopentyl, cyclohexyl and the like); aryl (e.g., $C_{6\sim10}$ aryl such as phenyl, 1-naphthyl, 2-naphthyl and the like); aralkyl (e.g., $C_{7\sim10}$ aralkyl such as benzyl, phenethyl and the like, preferably phenyl-$C_{1\sim4}$ alkyl and the like); arylalkenyl (e.g., $C_{8\sim10}$ arylalkenyl such as cinnamyl and the like, preferably phenyl-$C_{2\sim4}$ alkenyl and the like); a heterocyclic group (e.g., a group similar to the heterocyclic group in "the heterocyclic group which may be substituted" as the above substituent may be used. The lower alkyl, lower alkenyl, cycloalkyl, aryl, aralkyl, arylalkenyl, heterocyclic group may have a substituent, and for the substituent, a group similar to the substituent in the alkoxycarbonyl as the above substituent may be used at a similar number.

The N,N-disubstituted carbamoyl means a carbamoyl group witch has two substituent on the nitrogen atom, as an example of one substituent, a group similar to the substituent in the N-monosubstituted carbamoyl as the above substituent may be used, and as an example for the other substituent, for example, a lower alkyl (e.g., $C_{1\sim6}$ alkyl such as methyl, ethyl, propyl, isopropyl, butyl, tert-butyl, pentyl, hexyl and the like), $C_{3\sim7}$ cycloalkyl (e.g., cyclopropyl, cyclobutyl, cyclopentyl, cyclohexyl and the like), $C_{7\sim10}$ aralkyl (e.g., benzyl, phenethyl and the like, preferably phenyl-$C_{1\sim4}$ alkyl and the like) and the like may be used. In addition, two substituents, taken together with a nitrogen atom, may form a cyclic amino group. Such a cyclic aminocarbamoyl group may be, for example, a 3- to 8-membered (preferably a 5- or 6-membered) cyclic aminocarbonyl group such as 1-azetidinylcarbonyl; 1-pyrrolidinylcarbonyl; piperidinocarbonyl; morpholinocarbonyl; 1-piperazinylcarbonyl which may have a lower alkyl (e.g., $C_{1\sim6}$ alkyl such as methyl, ethyl, propyl, isopropyl, butyl, tert-butyl, pentyl, hexyl and the like), aralkyl (e.g., $C_{7\sim10}$ aralkyl such as benzyl, phenethyl and the like), aryl (e.g., $C_{6\sim10}$ aryl such as phenyl, 1-naphthyl, 2-naphthyl and the like) at its forth position; and the like.

For the substituent in "the thiocarbamoyl group which may be substituted" and "the sulfamoyl group which may be substituted" as the above substituent, a group similar to the substituent for the N-monosubstituted carbamoyl and the N,N-disubstituted carbamoyl in "the carboxyl group which may be esterified or amidated" as the above substituent may be used.

For the acyl from sulfonic acid as the above substituent, for example, a group in which one substituent on the nitrogen atom in the above N-monosubstituted carbamoyl is coupled with sulfonyl is used, and preferably acyl from $C_{1\sim6}$ alkylsulfonyl and the like such as methanesulfonyl, ethanesulfonyl and the like.

For the acyl from carboxylic acid as a substituent, a group in which a hydrogen atom or one substituent on the nitrogen atom in the above N-monosubstituted carbamoyl is coupled with carbonyl may be used, and preferably acyl from $C_{1\sim6}$ alkanoyl such as formyl, acetyl, propionyl, pivaloyl and the like; benzoyl and the like may be used.

$R^a$ is a hydrogen atom or a substituent. When $R^a$ is a substituent, for this substituent a group similar to the substituent in "the aromatic hydrocarbon group which may have a substituent" as the above substituent may be used at a similar number. Preferably, a lower alkoxyl group (e.g., $C_{1\sim6}$ alkoxy such as methoxy, ethoxy, propoxy and the like); a halogen atom (e.g., fluorine, chlorine, bromine, iodine and the like); a lower alkyl group (e.g. $C_{1\sim6}$ alkyl such as methyl, ethyl, propyl and the like); a lower alkenyl group (e.g., $C_{2\sim6}$ alkenyl such as vinyl, allyl and the like); a lower alkynyl group (e.g., $C_{2\sim6}$ alkynyl such as ethynyl, propargyl and the like); an amino group which may be substituted; a hydroxy group which may be substituted; a cyano group; an amidino group which may be substituted; a carbamoyl group which may be substituted (e.g., a $C_{1\sim6}$ alkyl group which may be substituted with a 5- or 6-membered monocyclic aromatic heterocyclic group (e.g., pyridinyl and the like); or a carbamoyl group, 1-azetidinylcarbonyl, 1-pyrrolidinylcarbonyl, piperidinocarbonyl, morpholinocarbonyl, 1-piperazinylcarbonyl and the like which may be substituted with an acyl group (e.g., formyl, $C_{2\sim6}$ alkanoyl, benzoyl, $C_{1\sim6}$ alkoxycarbonyl which may be halogenated, $C_{1\sim6}$ alkylsulfonyl which may be halogenated, benzenesulfonyl and the like), and the like); and the like may be used. Preferably, a hydroxy group which may be substituted may be used. For "the amino group which may be substituted", "the hydroxy group which may be substituted" and "the amidino group which may be substituted", a group similar to the substituent in "the aromatic hydrocarbon group which may have a substituent", "the hydroxy group which may be substituted", and "the amidino group which may be substituted" as the above substituent in "the amino group which may be substituted" may be used.

Y, $Y^1$ and $Y^2$ are, the same or different, a hydrogen atom or a substituent. When Y, $Y^1$ and $Y^2$ are substituents, for these substituents, the same or different groups similar to the substituent in "the amino group which may be substituted" for "the aromatic hydrocarbon group which may have a substituent" as the above substituent may be used at a similar number. Preferably, a lower alkyl group (e.g., $C_{1\sim6}$ alkyl such as methyl, ethyl, propyl, isopropyl, butyl, isobutyl, tert-butyl, pentyl, hexyl and the like) which may be substituted with a substituent selected from a halogen atom (e.g., fluorine, chlorine, bromine, iodine and the like), $C_{1\sim6}$ alkoxy which may be halogenated (e.g., methoxy, ethoxy, trifluoromethoxy, 2,2,2-trifluoroethoxy, trichloromethoxy, 2,2,2-trichloroethoxy and the like) and $C_{7\sim11}$ alkylaryl group (e.g., o-tolyl, m-tolyl, p-tolyl, xylyl, mesityl and the like, preferably $C_{1\sim5}$ alkylphenyl and the like); an acyl group ($C_{1\sim6}$ alkanoyl (e.g., formyl, acetyl, propionyl, pivaloyl and the like); benzoyl; $C_{1\sim6}$ alkylsulfonyl (e.g., methanesulfonyl and the like); benzenesulfonyl and the like); a $C_{1\sim6}$ alkoxycarbonyl group which may be halogenated (e.g., methoxycarbonyl, ethoxycarbonyl, trifluoromethoxycarbonyl, 2,2,2-trifluoroethoxycarbonyl, trichloromethoxycarbonyl, 2,2,2-trichloroethoxycarbonyl and the like); a $C_{1\sim6}$ alkoxycarbonyl group which may be substituted with a phenyl group (e.g., benzyloxycarbonyl and the like); aryl (e.g., $C_{6\sim10}$ aryl such as phenyl, 1-naphthyl, 2-naphthyl and the like); aralkyl (e.g., $C_{7\sim10}$ aralkyl such as benzyl, phenethyl and the like, preferably phenyl-$C_{1\sim4}$ alkyl and the like), arylalkenyl (e.g., $C_{8\sim10}$ arylalkenyl such as cinnamyl and the like, preferably phenyl-$C_{2\sim4}$ alkenyl and the like), a heterocyclic group (a group similar to the heterocyclic group in "the heterocyclic group which may be substituted" as the above substituent, preferably pyridyl, and more preferably 4-pyridyl and the like); an imidoyl group which may be substituted (e.g., $C_{1~6}$ alkylimidoyl (e.g., formylimidoyl, acetylimidoyl and the like), $C_{1~6}$ alkoxyimidoyl, $C_{1~6}$ alkylthioimidoyl, amidino and the like); an amino group which may be substituted with one or two $C_{1~6}$ an alkyl group and the like may be used.

$R^b$ is a protecting group which may be generally used in organic syntheses, and include, not limited to, but for example, formyl, $C_{1~6}$ alkylcarbonyl (e.g., acetyl, propionyl and the like), phenylcarbonyl, $C_{1~6}$ alkyloxycarbonyl (e.g., methoxycarbonyl, ethoxycarbonyl and the like), phenyloxycarbonyl, $C_{7~20}$ aralkyl (e.g., benzyl, phenylethyl, trityl, benzhydryl and the like), $C_{2~10}$ alkylsulfamoyl (e.g., dimethylsulfamoyl and the like), $C_{1~30}$ alkylsulfonyl (e.g., p-toluenesulfonyl, benzenesulfonyl, methylsulfonyl and the like), $C_{7~10}$ aralkyloxy-carbonyl (e.g., alkyloxy-carbonyl such as benzyloxycarbonyl and the like), methoxymethyl, benzyloxymethyl, trimethylsilylethoxymethyl, phthaloyl or N,N-dimethylaminomethylene and the like, each of which may have a substituent. For the substituent, a halogen atom, formyl, a $C_{1~6}$ alkylcarbonyl group, a nitro group and the like may be used, one to about three substituents may be used.

Embodiments for the metal hydride complexes specifically include, for example, an alkali metal hydride complex such as sodium borohydride, lithium borohydride, potassium borohydride, sodium cyanoborohydride, lithium tri(sec-butyl) borohydride, sodium tri(sec-butyl)borohydride and the like; and zinc borohydride and others. Preferably an alkali metal hydride complex such as sodium borohydride, lithium borohydride, potassium borohydride and the like; more preferably sodium borohydride and potassium borohydride; and further preferably sodium borohydride may be used.

Embodiments for the metal halides specifically include, for example, aluminum halides such as aluminum chloride, aluminum bromide and the like; lithium halides such as lithium iodide, lithium chloride, lithium bromide and the like; magnesium halides such as magnesium chloride, magnesium bromide; calcium halides such as calcium chloride, calcium bromide and the like; and boron fluoride, iron chloride, zinc chloride, antimony chloride and the like. Preferably, calcium halides such as calcium chloride and calcium bromide and the like; and more preferably, calcium chloride may be used.

Ether is a compound in which two hydrocarbon residues are coupled with one oxygen atom, and includes a chain and cyclic ether. Embodiments of ether specifically include, for example, an aliphatic single ether such as methyl ether, ethyl ether, propyl ether, butyl ether, isobutyl ether and the like; an aliphatic mixed ether such as methyl ethyl ether, 1,2-dimethoxyethane, bis(2-methoxyethyl)ether, methyl propyl ether, methyl isopropyl ether, methyl butyl ether, ethyl propyl ether, ethyl butyl ether, ethyl isoamyl ether and the like; an aliphatic unsaturated ether such as vinyl ether, allyl ether, methyl vinyl ether, ethyl vinyl ether and the like; an aromatic ether such as anisole, phenetole, phenyl ether, benzyl ether, phenyl benzyl ether and the like; a cyclic ether such as ethylene oxide, propylene oxide, trimethylene oxide, tetrahydrofuran, tetrahydropyran, dioxane and the like. Preferably, an aliphatic single ether such as methyl ether, ethyl ether and the like; an aliphatic mixed ether such as methyl ethyl ether, methyl propyl ether and the like; a cyclic ether such as tetrahydrofuran, tetrahydropyran, dioxane; more preferably a cyclic ether such as tetrahydrofuran, tetrahydropyran, dioxane; and further preferably tetrahydrofuran may be used.

Alcohol is a compound other than phenol in which a hydrogen atom in the hydrocarbon is substituted with a hydroxy group. Embodiments of alcohol specifically includes, for example, an aliphatic saturated alcohol such as methyl alcohol, ethyl alcohol, propyl alcohol, isopropyl alcohol, butyl alcohol and the like; an aliphatic unsaturated alcohol such as allyl alcohol, crotyl alcohol, propargyl alcohol and the like; an alicyclic alcohol such as cyclopentanol, cyclohexanol and the like; an aromatic alcohol such as benzyl alcohol, cinnamyl alcohol and the like; and a heterocyclic alcohol such as furfuryl alcohol and the like. Preferably, an aliphatic saturated alcohol such as methyl alcohol, ethyl alcohol, propyl alcohol, isopropyl alcohol, butyl alcohol; more preferably a $C_{1~6}$ alcohol such as methyl alcohol, ethyl alcohol, propyl alcohol, isopropyl alcohol, butyl alcohol; further preferably methyl alcohol, ethyl alcohol, propyl alcohol; still further preferably methyl alcohol, ethyl alcohol; and most preferably ethyl alcohol may be used.

Salts which may be used in the present invention include, for example, a salt with an inorganic base, an ammonium salt, a salt with an organic base, a salt with an inorganic acid, a salt with an organic acid, a salt with a basic or acidic amino acid and the like. Preferable examples of a salt with an inorganic base include an alkali. metal salt such as a sodium salt, a potassium salt and the like; an alkaline earth metal salt such as a calcium salt, a magnesium salt and the like; an aluminum salt and the like. Preferable examples of a salt with an organic base include salts with trimethylamine, triethylamine, pyridine, picoline, ethanolamine, diethanolamine, triethanolamine, dicyclohexylamine, N,N'-dibenzylethylenediamine and the like. Preferable examples of salts with an inorganic acid include salts with hydrochrolic acid, hydrobromic acid, nitric acid, sulfuric acid, phosphoric acid and the like. Preferable examples of salts with an organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of salts with a basic amino acid include salts with arginine, lysine, ornithine and the like, and preferable examples of salts with an acidic amino acid include salts with aspartic acid, glutamic acid and the like.

According to the present invention, a primary alcohol may be produced by selectively reducing (1) an esterified carboxyl group and (2) an esterified carboxyl group in a compound having an N-unsubstituted amide group or an N-monosubstituted amide group, in an ether-alcohol solvent in the presence of a metal hydride complex and a calcium halide.

The esterified carboxyl group means a carboxyl group having a substituent similar to the above R as an ester residue. For the substituent in the N-monosubstituted amide group, a group similar to the substituent in "the amino group which may be substituted" as the above substituent.

$R^a$ is preferably a hydrogen atom, a $C_{1~6}$ alkyl group, a hydroxy group, a thiol group, or a halogen atom and the like.

R, Y, $Y_1$ and $Y_2$ are, the same or different, preferably a $C_{1~6}$ alkyl group.

Ar is preferably naphthyl, benzothiazolyl, or biphenyl.

The ring B is preferably imidazole or triazole.

n is preferably an integer of 1 to 3 and more preferably 1 or 2.

The metal hydride complex is preferably an alkali metal hydride complex, more preferably an alkali metal borohydride, and further preferably sodium borohydride.

The metal halide is preferably a calcium halide, more preferably calcium chloride.

$R^b$ is preferably a trityl group.

Ether is preferably a cyclic ether, more preferably tetrahydrofuran.

Alcohol is preferably a $C_{1~6}$ alcohol, and more preferably ethanol or methanol.

In the reduction reaction according to the present invention, a mixed solvent of ether and alcohol is preferably used. More preferably, alcohol is added to a reaction system in an ether solvent. Further preferably, a $C_{1-6}$ alcohol is added to a reaction system in a cyclic ether solvent, and still further preferably ethanol or methanol is added to a reaction system in tetrahydrofuran as a solvent.

In a reduction reaction according to the present invention, most preferably, the metal hydride complex is sodium borohydride, the calcium halide is calcium chloride, ether is tetrahydrofuran, the alcohol is ethanol or methanol, and ethanol or methanol is added to a reaction system in tetrahydrofuran as a solvent.

In addition, the present inventors have made every effort to study possibility on an industrially advantageous process for producing a Reformatsky reagent, wherein the process being excellent in reproducibility, and have succeeded in producing a solution of ethyl bromozincacetate in tetrahydrofuran (THF) at a high reproducibility by using an excess amount of zinc relative to ethyl bromoacetate in THF to accomplish the present invention. According to the present process for producing a Reformatsky reagent, a Reformatsky reagent can be produced at high reproducibility with no steep initiation of reaction and no extreme reduction in yielding.

In addition, it has been found that the solution of ethyl bromozincacetate in THF is surprisingly very stable, and that specifically, when the solution is maintained at 0-5° C., the solution can be used as a reagent substantially without any problem in production for at least two months.

Further, the present inventors have first succeeded in crystallizing ethyl bromozincacetate from a THF solution of ethyl bromozincacetate, and have revealed from an X-ray crystallography of the isolated crystal that this crystal has a structure of ethyl bromozincacetate.THF binuclear complex $((BrZnCH_2COOC_2H_5.THF)_2)$.

Use of the ethyl bromozincacetate.THF binuclear complex in this crystal form allows obtaining a derivative of β-hydroxy acid of interest at a high yield even in a Reformatsky reaction wherein the derivative is obtained at a low yield by a conventional process. Thus, the Reformatsky reagent in the crystal form obtained according to the present invention is very useful.

In addition, it has been found that the Reformatsky reagent in this crystal form is also very stable, and specifically, when this crystal is maintained under an inert gas atmosphere at 0-5° C., the crystal can be used as a reagent substantially without any problem in production for at least six months.

Although it has been found that the. THF solution of ethyl bromozincacetate could be prepared reproducibly and the solution was stable as mentioned above, there remains a possibility to occur unexpectedly crystallization of ethyl bromozincacetate in some combinations between a temperature and a concentration in use or storage.

Naturally, crystallization may be avoided by controlling a temperature and a concentration, and even when crystallization has occurred, there is no practical problem after dissolving the crystals again by heating and the like. However, for example in the case where the possibility of crystallization is reduced by decreasing the concentration, productivity decreases. Further, unexpected crystallization during a large scaled production results in a risk which is a critical obstacle in handling and reproducibility.

Therefore, the present inventors further studied on obtaining a stable solution of ethyl bromozincacetate in which crystallization does not occur at a relatively high concentration in order to minimize the above risk in an industrial large scale production without reducing productivity.

JP-A 302287/1999 describes a process for preventing crystallization of a Grignard reagent by adding alkylene glycol ethers to a solution of the Grignard reagent in THF. According to this process, the present inventors prepared ethyl bromozincacetate in THF, and then 1,2-dimethoxyethane (DME) was added to this THF solution but crystallization could not be prevented.

The present inventors have succeeded in preventing crystallization from a solution of Reformatsky reagent at a relatively high concentration by using DME or cyclopentyl methyl ether (CPME) in place of THF as a solvent in a production of a Reformatsky reagent. It may be mainly because under these conditions a crystalline ethyl bromozincacetate.THF complex is not formed due to the absence of THF in a system, and because crystallization of ethyl bromozincacetate itself and a complex thereof with DME or CPME is difficult under the above condition.

It has been found that the resulting solution of a Reformatsky reagent in CPME is very stable without causing crystallization at higher concentrations than that of the above stable THF solution, and that when the solution is maintained at 0-5° C., the solution can be used as a reagent substantially without any problem in production for at least one month.

Further, the present inventors have succeeded in crystallizing and isolating a Reformatsky reagent.THF binuclear complex from these solutions by adding THF to the aforementioned DME solution and CPME solution.

Thus, according to the present invention, a very stable Reformatsky reagent can be provided in a form of a crystal and a solution.

BEST MODE FOR CARRYING OUT THE INVENTION

The present invention will be explained in detail by using Examples, but they never limit the present invention in any way.

[Process for Producing A]

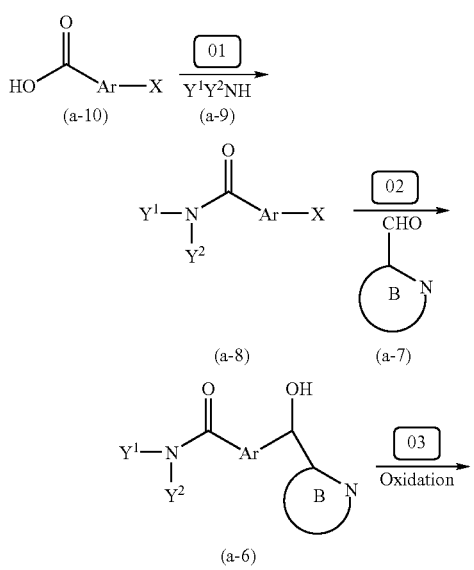

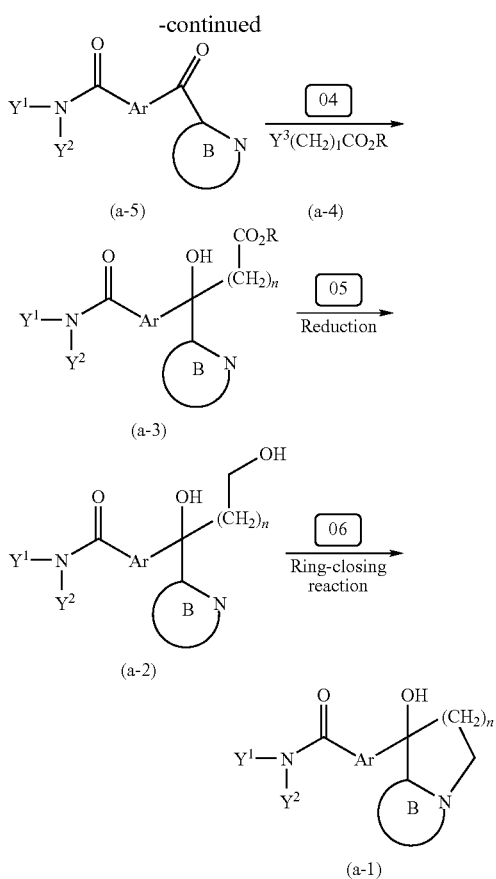

wherein each symbol is the same as defined above, X is a halogen atom, and $Y^3$ is a hydrogen atom or a halogen atom.

[Step 01]

The compound (a-8) is obtained by reacting a compound (a-10) or a reactive derivative thereof with a compound (a-9).

The solvent used in this reaction is not particularly limited as far as not affecting the reaction, and include, for example, aromatic hydrocarbons such as benzene, toluene, xylene and the like; aliphatic hydrocarbons such as hexane, pentane, heptane and the like; esters such as ethyl acetate, butyl acetate and the like; ethers such as diethyl ether, diisopropyl ether, t-butyl methyl ether, tetrahydrofuran, dioxane, 1,2-dimethoxyethane, bis(2-methoxyethyl)ether and the like; aliphatic halogenated hydrocarbons such as methylene chloride, chloroform, dichloroethane and the like; aromatic halogenated hydrocarbons such as chlorobenzene, dichlorobenzene, benzotrifluoride and the like; ketones such as acetone, methyl ethyl ketone and the like; aprotic polar solvents such as N,N-dimethylformamide, N,N-dimethylacetoamide, N-methylpyrrolidone, dimethyl sulfoxide and the like. The aforementioned ethers, esters, aprotic polar solvents are preferable, and particularly tetrahydrofuran, ethyl acetate, N,N-dimethylformamide are preferable. These may be used alone or in combination of any two or more of them at an appropriate ratio.

The amount of the solvent to be used in this reaction is 1~50 parts by weight, preferably 5~25 parts by weight, particularly preferably 5~10 parts by weight relative to the amount of the material compound (a-10).

The halogenating agent used in this reaction includes, for example, thionyl chloride, phosphorus pentachloride and the like, and thionyl chloride is preferable. The amount of thionyl chloride to be used in this reaction is 1~10 equivalents, preferably 1~5 equivalents, and particularly preferably 1~3 equivalents relative to the amount of the material compound (a-10).

The amount of the compound (a-9) to be used in this reaction is 1~10 equivalents, preferably 1-5 equivalents, and particularly preferably 1~3 equivalents relative to the amount of the material compound (a-10).

The base used in this reaction includes, for example, inorganic bases such as lithium hydroxide, potassium hydroxide, sodium hydroxide, sodium carbonate, potassium carbonate, sodium bicarbonate and the like; tertiary amines such as triethylamine, ethyldiisopropylamine, tri(n-propyl)amine, tri(n-butyl)amine, cyclohexyldimethylamine, pyridine, lutidine, N,N-dimethylaniline, N-methylpiperidine, N-methylpyrrolidine, N-methylmorpholine and the like. Particularly, triethylamine, ethyldiisopropylamine are preferable. The amount of these bases to be used is 0~10 equivalents, preferably 0~5 equivalents, and particularly preferably 1~3 equivalents relative to the amount of the material compound (a-10).

The reaction temperature is generally –80~200° C., and preferably 0~30° C.

The reaction time is generally 5 minutes to 48 hours, and preferably 1~5 hours.

In this reaction, a dehydrating condensing agent such as 1-β-dimethylaminopropyl)-3-ethylcarbodiimide, dicyclohexylcarbodiimide and the like may be used in place of a halogenating agent.

[Step 02]

The compound (a-6) is obtained by reacting the compound (a-8) or a reactive derivative thereof with a metal compound such as alkyllithium and the like or a metal compound such as magnesium to form an organic metal compound, and reacting it with the compound (a-7).

The solvent used in this reaction is not particularly limited as far as not affecting the reaction, and includes, for example, aromatic hydrocarbons such as benzene, toluene, xylene and the like; aliphatic hydrocarbons such as hexane, pentane, heptane and the like; ethers such as diethyl ether, diisopropyl ether, t-butylmethyl ether, tetrahydrofuran, dioxane, 1,2-dimethoxyethane, bis(2-methoxyethyl)ether and the like; aliphatic halogenated hydrocarbons such as methylene chloride, chloroform, dichloroethane and the like; aromatic halogenated hydrocarbons such as chlorobenzene, dichlorobenzene, benzotrifluoride and the like. The aforementioned ethers, aliphatic hydrocarbons are preferable, and particularly tetrahydrofuran, toluene, n-hexane are preferable. These may be used alone or in combination of any two or more of them at an appropriate ratio.

The amount of the solvent to be used in this reaction is 1~100 parts by weight, preferably 20~80 parts by weight, particularly preferably 50~70 parts by weight relative to the amount of the material compound (a-8).

The alkyllithium used in this reaction includes, for example, $C_{1-4}$ alkyllithium such as n-butyllithium, s-butyllithium, t-butyllithium and the like. Particularly, n-butyllithium is preferable. The amount of alkyllithium used in this reaction is 1~10 equivalents, particularly preferably 2~3 equivalents relative to the amount of the material compound (a-8).

The reaction temperature is generally –120~0° C., preferably –100~–20° C.

The reaction time is generally 5 minutes to 48 hours, and preferably 1~2 hours.

When X is a halogen atom, this is reacted with magnesium to obtain a Grignard reagent, which is then reacted with the compound (a-7). When the compound (a-8) is reacted with magnesium, the reaction temperature is generally −40~60° C., and preferably −20~40° C. The reaction time is generally 5 minutes to 48 hours, and preferably 1~20 hours.

When alkyllithium is used in this reaction, the existence of an anion obtained by reacting 2-bromobenzene trifluoride with alkyllithium (a benzene trifluoride anion) increases the reaction yield.

[Step 03]

The compound (a-5) is obtained by oxidizing the compound (a-6) by using an oxidizing agent.

The solvent used in this reaction is not particularly limited as far as not affecting the reaction, and includes, for example, aromatic hydrocarbons such as benzene, toluene, xylene and the like; aliphatic hydrocarbons such as hexane, pentane, heptane and the like; esters such as ethyl acetate, butyl acetate and the like; ethers such as diethyl ether, diisopropyl ether, t-butyl methyl ether, tetrahydrofuran, dioxane, 1,2-dimethoxyethane, bis(2-methoxyethyl)ether and the like; aliphatic halogenated hydrocarbons such as methylene chloride, chloroform, dichloroethane and the like; aromatic halogenated hydrocarbons such as chlorobenzene, dichlorobenzene, benzotrifluoride and the like; ketones such as acetone, methyl ethyl ketone and the like; aprotic polar solvents such as acetonitrile, N,N-dimethylformamide, N,N-dimethylacetoamide, N-methylpyrrolidone, dimethyl sulfoxide and the like. The aforementioned aliphatic halogenated hydrocarbons, esters, aprotic polar solvents are preferable, and particularly, dichloromethane, ethyl acetate, N,N-dimethylformamide are preferable. These may be used alone or in combination of any two or more of them at an appropriate ratio.

The amount of the solvent used in this reaction is 1~50 parts by weight, and preferably 10~30 parts by weight relative to the amount of the material compound (a-6).

The oxidizing agent used in this reaction includes, for example, chromic acid-acetic acid, a Jones reagent, anhydrous chromic acid-pyridine complexes, manganese dioxide, silver carbonate-Celite, dimethyl sulfoxide-oxazolyl chloride, aluminum alkoxide-ketone, triphenylbismuth carbonate, tetrapropylammonium-perruthenate, ruthenium tetroxide, hypochlorous acid-acetic acid, periodinane compounds and the like. Particularly, manganese dioxide is preferable. The amount of the oxidizing agent used in this reaction is 1~30 equivalents, and preferably 10~20 equivalents relative to the amount of the material compound (a-6). The reaction temperature is generally −80~200° C., and preferably 30~50° C.

The reaction time is generally 5 minutes to 48 hours, and preferably 3-8 hours.

[Step 04]

The compound (a-3) is obtained by reacting the compound (a-5) with a lithium salt ($Y^3$; a hydrogen atom) or an organic zinc compound ($Y^3$; a halogen atom) prepared from the compound (a-4).

The solvent used in this reaction is not particularly limited as far as not affecting the reaction, and includes, for example, aromatic hydrocarbons such as benzene, toluene, xylene and the like; aliphatic hydrocarbons such as hexane, pentane, heptane and the like; esters such as ethyl acetate, butyl acetate and the like; ethers such as diethyl ether, diisopropyl ether, t-butyl methyl ether, tetrahydrofuran, dioxane, 1,2-dimethoxyethane, bis(2-methoxyethyl)ether and the like; aliphatic halogenated hydrocarbons such as methylene chloride, chloroform, dichloroethane and the like; aromatic halogenated hydrocarbons such as chlorobenzene, dichlorobenzene, benzotrifluoride and the like; ketones such as acetone, methyl ethyl ketone and the like; aprotic polar solvents such as acetonitrile, N,N-dimethylformamide, N,N-dimethylacetoamide, N-methylpyrrolidone, dimethyl sulfoxide and the like. The aforementioned aliphatic hydrocarbons, aromatic hydrocarbons, ethers are preferable, and particularly, tetrahydrofuran, n-hexane are preferable. These may be used alone or in combination of any two or more of them at an appropriate ratio.

The amount of the solvent used in this reaction is 1~50 parts by weight, and preferably 10~30 parts by weight relative to the amount of the material compound (a-5).

The lithium alkylamide used in this reaction includes, for example, lithium dimethylamide, lithium diethylamide, lithium diisopropylamide, lithium dicyclohexylamide, lithium bis(trimethylsilyl)amide and the like. Particularly, lithium diisopropylamide is preferable. The amount of lithium alkylamide used in this reaction is 1~10 equivalents, and preferably 2~4 equivalents relative to the amount of the material compound (a-5).

The reaction temperature is generally −120~0° C., and preferably −100~−20° C.

The reaction time is generally 5 minutes to 20 hours, and preferably 30 minutes to 2 hours.

When the compound (a-3) is obtained by reacting the compound (a-5) with an organic zinc compound (a Reformatsky reagent) in this reaction, the reaction temperature is generally −80~150° C., and preferably −40~20° C. The reaction time is generally 5 minutes to 20 hours, and preferably 30 minutes to 5 hours. The amount of the organic zinc compound used in this reaction is 1~10 equivalents, and preferably 1.2~5 equivalents relative to the amount of the material compound (a-5).

In preparation of a Reformatsky reagent, zinc is used in a form of, for example, powder, flake, wire, and foil, and particularly zinc is preferably used in a form of powder. It is preferable that zinc is treated by a conventional acid cleaning before use, but commercial zinc is used without any treatment. It is preferable that excess amount of zinc is used relative to one mole amount of the sub material compound (a-4) in preparation of a Reformatsky reagent. Specifically, it is preferable that zinc exists in an amount more than 1 gram atom, more preferably more than 1 gram atom and 50 gram atoms or less, further preferably more than 1 gram atom and 5 gram atoms or less, and most preferably more than 1 gram atom and 3 gram atoms or less. It is better that the water content in a solvent used in preparing a Reformatsky reagent is less, and it is particularly preferable that the content is 0.005% or less. Optionally, a stabilizer (2,6-di-t-butyl-4-methyl-phenol and the like) may be added to tetrahydrofuran. It is preferable that zinc is activated.

An activating agent used in the present invention includes, for example, iodine, 1,2-dibromoethane, copper halide, silver halide, chlorotrimethylsilane, molecular sieves and the like, and particularly chlorotrimethylsilane is preferable. Zinc-Copper couple, Rieke Zn, Zinc-Silver-Graphite, zinc chloride-lithium, zinc chloride-lithium naphthalide, zinc and zinc compounds activated with super sonic and the like. The reaction temperature in preparation of a Reformatsky reagent is generally −80~150° C., and preferably −10~40° C. The reaction time is generally 1 minute to 20 hours, and preferably 20 minutes to 1 hour.

Optically active compounds may be obtained by reacting the compound (a-5) with an organic zinc compound in the presence of an appropriate asymmetric ligand. The asymmetric ligand includes, for example, an optical active amino alcohol derivative and an optically active amine derivative. Embodiments of the optically active amino alcohol derivative include cinchona alkaloids such as cinchonine, chinchonidine, quinidine, quinine and the like; N-methylephedrine, norephedrine, 3-exo-(dimethylamino)isoborneol, 1-methyl- 2-pyrrolidinemethanol, 1-benzyl-2-pyrrolidinemethanol, 2-[hydroxy(diphenyl)methyl]-1-methylpyrrolidine and the like. By selecting an asymmetric ligand used, a compound having a desired configuration may be obtained.

Ester interchange of the compound (a-3) may also be carried out by using an organic titanium compound such as titanium isopropoxide, titanium ethoxide, titanium methoxide and the like.

[Step 05]

The compound (a-2) is obtained by reducing reaction of the compound (a-3) or a reactive derivative thereof in the presence of a metal hydride complex and a metal halide.

The solvent used in this reaction is not particularly limited as far as not affecting the reaction, and includes, for example, aromatic hydrocarbons such as benzene, toluene, xylene and the like; aliphatic hydrocarbons such as hexane, pentane, heptane and the like; ethers such as diethyl ether, diisopropyl ether, t-butyl methyl ether, tetrahydrofuran, dioxane, 1,2-dimethoxyethane, bis(2-methoxyethyl)ether and the like; aliphatic halogenated hydrocarbons such as methylene chloride, chloroform, dichloroethane and the like; aromatic halogenated hydrocarbons such as chlorobenzene, dichlorobenzene, benzotrifluoride and the like; alcohols such as methanol, ethanol, 1-propanol, 2-propanol, 1-butanol, 2-butanol, 2-methyl-1-propanol and the like; aprotic polar solvents such as acetonitrile, N,N-dimethylformamide, N,N-dimethylacetoamide, N-methylpyrrolidone, dimethyl sulfoxide and the like. These may be used alone or in combination of any two or more of them at an appropriate ratio. The aforementioned ethers, alcohols are preferable, and particularly, a mixed solvent of ethers-alcohols is preferable. More preferably, alcohols are added in a reaction system in ethers as a reaction solvent. Particularly, a mixed solvent such as tetrahydrofuran-ethanol, tetrahydrofuran-methanol is preferable, and further preferably ethanol or ethanol is added to a reaction system in tetrahydrofuran as a reaction solvent.

The amount of the solvent used in this reaction is 1~50 parts by weight, and preferably 10~30 parts by weight relative to the amount of the material compound (a-3).

The metal hydride complex used in this reaction includes, for example, alkali metal hydride complexes such as sodium borohydride, lithium borohydride, potassium borohydride, sodium cyanoborohydride and the like; and zinc borohydride and others. Preferably, alkali metal hydride complexes such as sodium borohydride, lithium borohydride, potassium borohydride and the like are used, more preferably sodium borohydride, potassium borohydride are used, and most preferably sodium borohydride is used. The amount of the metal hydride complex used in this reaction is 2~20 equivalents, and particularly preferably 6~10 equivalents relative to the amount of the material compound (a-3).

The metal halide used in this reaction includes, for example, aluminum halides such as aluminum chloride, aluminum bromide and the like; lithium halides such as lithium iodide, lithium chloride, lithium bromide and the like; magnesium halides such as magnesium chloride, magnesium bromide and the like; calcium halides such as calcium chloride, calcium bromide and the like; zinc halides such as zinc chloride, zinc bromide and the like; iron chloride; tin chloride; boron fluoride and the like. Preferably, calcium halides such as calcium chloride, calcium bromide and the like; zinc halides such as zinc chloride, zinc bromide and the like are used, and more preferably calcium halides such as calcium chloride, calcium bromide and the like, and most preferably calcium chloride is used. The amount of the metal halide in this reaction is 1~10 equivalents, and particularly preferably 3~5 equivalents relative to the amount of the material compound (a-3).

The reaction temperature is generally −80~200° C., and preferably 0~50° C.

The reaction time is generally 5 minutes to 48 hours, and preferably 3~24 hours.

[Step 06]

The compound (a-1) is obtained by converting the alcohol residue in the compound (a-2) into a leaving group, and reacting it in the presence or in the absence of a base.

The solvent used in this reaction is not particularly limited as far as not affecting the reaction, and includes, for example, aromatic hydrocarbons such as benzene, toluene, xylene and the like; aliphatic hydrocarbons such as hexane, pentane, heptane and the like; ethers such as diethyl ether, diisopropyl ether, t-butyl methyl ether, tetrahydrofuran, dioxane, 1,2-dimethoxyethane, bis(2-methoxyethyl)ether and the like; aliphatic halogenated hydrocarbons such as methylene chloride, chloroform, dichloroethane and the like; aromatic halogenated hydrocarbons such as chlorobenzene, dichlorobenzene, benzotrifluoride and the like; alcohols such as methanol, ethanol, 1-propanol, 2-propanol, 1-butanol, 2-butanol, 2-methyl-1-propanol and the like; aprotic polar solvents such as acetonitrile, dimethylformamide, N,N-dimethylacetoamide, N-methylpyrrolidone, dimethyl sulfoxide and the like. The aforementioned aromatic hydrocarbons, ethers, alcohols, aprotic polar solvents are preferable, and particularly toluene, tetrahydrofuran, ethanol, methanol, acetonitrile are preferable. More preferably, tetrahydrofuran, methanol, acetonitrile are used. These may be used alone or in combination of any two or more of them at an appropriate ratio.

The amount of the solvent used in this reaction is 1~50 parts by weight, and preferably 10~30 parts by weight relative to the amount of the material compound (a-2).

The leaving group introducing agent includes, for example, alkylsulfonyl halides such as methanesulfonyl chloride, p-toluenesulfonyl chloride and the like; and halogenating agents such as carbon tetrachloride-triphenylphosphine, N-chlorosuccinimide-triphenylphosphine, thionyl chloride, lithium chloride, carbon tetrabromide-triphenylphosphine, N-bromosuccinimide-triphenylphosphine, phosphorus tribromide, phosphorus bromide, sodium bromide, sodium iodide, imidazole-iodine-triphenylphosphine and the like. Preferably, alkylsulfonyl halides such as methanesulfonyl chloride, p-toluenesulfonyl chloride and the like is used, and particularly methanesulfonyl chloride is preferable. The amount of the leaving group introducing agent is 1~10 equivalents, preferably 1~5 equivalents, and particularly preferably 1~2 equivalents relative to the amount of the material compound (a-2).

The base used in this reaction includes, for example, tertiary amines such as triethylamine, ethyldiisopropylamine, tri(n-propyl)amine, tri(n-butyl)amine, cyclohexyldimethylamine, pyridine, lutidine, N,N-dimethylaniline, N-methylpiperidine, N-methylpyrrolidine, N-methylmorpholine and the like. Particularly, triethylamine, ethyldiisopropylamine are preferable. The amount of these bases is 0~10 equivalents, and particularly preferably 2~6 equivalents relative to the amount of the material compound (a-2).

The reaction temperature is generally 30~120° C., and preferably 50~80° C.

The reaction time is generally 5 minutes to 48 hours, and preferably 2~5 hours.

The compounds (a-10) and (a-7), which are starting material in the above step, may be synthesized by a generally known synthesis in an organic chemistry field, or methods described in or methods analogue to those in *J. Am. Chem. Soc.,* 1943, 65, 239 for the compound (a-10); and *J. Med. Chem.,* 1977, 20, 721 for the compound (a-7).

The compound obtained in each of the above steps may be isolated or purified from the reaction mixture by using a known means per se, for example, extracting, concentrating, neutralizing, filtering, recrystallizing, column chromatography, thin layer chromatography and the like, or the reaction mixture itself may be used as a material for the following step.

When the compound is obtained in a free form by each reaction according to the present invention, the free form may be converted into a salt thereof using a conventional method, and when the compound is obtained in a salt form, the salt form may be converted into a free form or other salt form.

In addition the above compound or a salt thereof may be a hydrate, and both hydrate and anhydrate thereof are within a scope of the present invention.

In addition, the present invention provides a crystal of ethyl bromozincacetate which is known to be a Reformatsky reagent. Particularly, the present invention provides a crystal of ethyl bromozincacetate to which tetrahydrofuran (THF) coordinates, and more specifically, the present invention provides a compound represented by a formula $(BrZnCH_2COOC_2H_5 \cdot THF)_2$.

The present crystal of ethyl bromozincacetate to which THF coordinates has peaks at 2983, 2897, 1589, 1446, 1371, 1286, 1070, 1022, 858 and 769 (cm$^{-1}$) by FT-IR.

The present crystal of ethyl bromozincacetate to which THF coordinates has a structure determined by an X-ray crystallography shown in FIG. 1, wherein the structure having bond lengths listed in Table 1, bond angles listed in Table 2 and crystallographic data and structure refinement listed in Table 3.

According to the present invention, the compound represented by the formula $(BrZnCH_2COOC_2H_5 \cdot THF)_2$ may be crystallized from a solution of $BrZnCH_2COOC_2H_5$ in THF.

A crystal of the compound represented by the formula $(BrZnCH_2COOC_2H_5 \cdot THF)_2$ may be isolated by crystallizing the compound represented by the formula $(BrZnCH_2COOC_2H_5 \cdot THF)_2$ from a solution of $BrZnCH_2COOC_2H_5$ in THF by using alone or in combination of any of a conventional crystallizing method such as standing, stirring, concentrating, cooling, seeding and the like, and then filtrating the crystal. It is preferable that the above step is carried out under an inert gas such as nitrogen, argon and the like.

Alternatively, according to the present invention, the crystal of the compound represented by the formula $(BrZnCH_2COOC_2H_5 \cdot THF)_2$ may be formed by reacting the compound represented by the formula. $BrZnCH_2COOC_2H_5$ with THF upon addition of THF in a solution of $BrZnCH_2COOC_2H_5$ in 1,2-dimethoxyethane or cyclopentyl methyl ether.

For example, the crystal of the compound represented by the formula $(BrZnCH_2COOC_2H_5 \cdot THF)_2$ may be isolated by adding THF in a solution of $BrZnCH_2COOC_2H_5$ in 1,2-dimethoxyethane or cyclopentyl methyl ether, crystallizing the compound represented by the formula $(BrZnCH_2COOC_2H_5 \cdot THF)_2$ from the resulting mixed solution by using alone or in combination of any of a conventional crystallizing method such as standing, stirring, concentrating, cooling, seeding and the like, and then filtrating the crystal. It is preferable that the above step is carried out under an inert gas such as nitrogen, argon and the like.

Alternatively, according to the present invention, the crystal of the compound represented by a formula $(BrZnCH_2COOC_2H_5 \cdot THF)_2$ may be formed by reacting the compound represented by a formula $BrCH_2COOC_2H_5$ with an excess amount of zinc relative to the compound represented by a formula $BrCH_2COOC_2H_5$ in the presence of an activating agent in an organic solvent selected from a group consisting of 2-methyl-tetrahydrofuran, 1,2-dimethoxyethane and cyclopentyl methyl ether or a mixed solvent in combination of any two or more of the aforementioned organic solvents, followed by adding THF to the resultant solution.

Further, the present invention provides a process for producing a compound represented by the general formula (V):

(V)

wherein $X^1$ is a bromine atom or an iodine atom; and $R^{11}$ and $R^{12}$ are, the same or different and independently, a hydrogen atom, an aliphatic hydrocarbon group which may have a substituent, an alicyclic hydrocarbon group which may have a substituent, a heterocyclic group which may have a substituent, an aromatic hydrocarbon group which may have a substituent, an aromatic heterocyclic group which may have a substituent, and $R^{10}$ is an ester residue; or $R^{11}$ is a hydrogen atom, an aliphatic hydrocarbon group which may have a substituent, an alicyclic hydrocarbon group which may have a substituent, a heterocyclic group which may have a substituent, an aromatic hydrocarbon group which may have a substituent, an aromatic heterocyclic group which may have a substituent, and $R^{10}$ and $R^{12}$, taken together with the atom to which they are bonded, form a lactone ring which may have a substituent, which comprises reacting a compound represented by the general formula (IV):

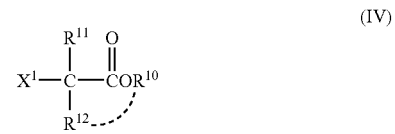

(IV)

wherein $X^1$, $R^{10}$, $R^{11}$ and $R^{12}$ are the same as defined above with zinc in a solvent selected from a group consisting of 2-methyltetrahydrofuran, 1,2-dimethoxyethane, cyclopentyl methyl ether and tetrahydrofuran, or in a mixed solvent in any combination of two or more of them in the presence of an activating agent, wherein zinc exists in an excess amount relative to the compound represented by the general formula (IV).

In the compound represented by the general formula (IV), for the aliphatic hydrocarbon group in "the aliphatic hydrocarbon group which may have a substituent", for example, a linear- or branched-chain aliphatic hydrocarbon such as an alkyl group, alkenyl group, alkynyl group and the like may be used.

For the alkyl group, for example, $C_{1-10}$ alkyl groups (preferably, $C_{1-6}$ alkyl groups and the like) such as methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl, 2-ethylbutyl, n-heptyl, 1-methylheptyl, 1-ethylhexyl, n-octyl, 1-methylheptyl, nonyl and the like may be used.

For the alkenyl group, for example, $C_{2-6}$ alkenyl groups such as vinyl, allyl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl and the like may be used.

For the alkynyl group, for example, $C_{2-6}$ alkynyl groups such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like may be used.

The aliphatic hydrocarbon group in "the alicyclic hydrocarbon group which may have a substituent" includes, for example, saturated or unsaturated alicyclic hydrocarbon groups such as a cycloalkyl group, a cycloalkenyl group, a cycloalkanedienyl group and the like.

For the cycloalkyl group, for example, $C_{3-9}$ cycloalkyl such as cyclopropyl, cyclobutyl, cyclopentyl, cyclohexyl, cycloheptyl, cyclooctyl, cyclononyl and the like may be used.

For the cycloalkenyl group, for example, $C_{3-6}$ cycloalkenyl groups such as 2-cyclopenten-1-yl, 3-cyclopenten-1-yl, 2-cyclohexen-1-yl, 3-cyclohexen-1-yl, 1-cyclobuten-1-yl, 1-cyclopenten-1-yl and the like may be used.

For the cycloalkanedienyl group, for example, $C_{4-6}$ cycloalkanedienyl groups such as 2,4-cyclopentanedien-1-yl, 2,4-cyclohexanedien-1-yl, 2,5-cyclohexanedien-1-yl and the like may be used.

For the heterocyclic group in "the heterocyclic group which may have a substituent", for example, 3- to 8-membered saturated or unsaturated non-aromatic heterocyclic groups (aliphatic heterocyclic groups) such as oxiranyl, azetidinyl, oxetanyl, thietanyl, pyrrolidinyl, tetrahydrofuryl, thioranyl, piperidyl, tetrahydropyranyl, morpholinyl, thiomorpholinyl, piperazinyl and the like; or non-aromatic heterocyclic groups in which a part or all of double bonds in the above monocyclic aromatic heterocyclic group or fused polycyclic aromatic heterocyclic group are saturated, such as 1,2,3,4-tetrahydroquinolyl, 1,2,3,4-tetrahydroisoquinolyl and the like may be used.

For the aromatic hydrocarbon group in "the aromatic hydrocarbon group which may have a substituent", monocyclic or fused polycyclic aromatic hydrocarbon groups and the like are used, and $C_{6-14}$ aromatic hydrocarbon group is preferably used. Specifically, for example, $C_{6-14}$ aromatic hydrocarbon groups such as phenyl, naphthyl, anthryl, azulenyl, phenanthryl, phenalenyl, fluorenyl, indacenyl, biphenylenyl-haptalenyl, acenaphthylenyl and the like are preferable.

For the aromatic heterocyclic group in "the aromatic heterocyclic group which may have a substituent", 5- or 6-membered monocyclic aromatic heterocyclic groups such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like; and 8- to 12-membered fused polycyclic aromatic heterocyclic groups such as benzofuranyl, isobenzofuranyl, benzo[b]thienyl, indolyl, isoindolyl, 1H-indazolyl, benzindazolyl, benzoxazolyl, 1,2-benzisoxazolyl, benzothiazolyl, benzopyranyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl and the like may be used.

The aforementioned substituents are not particularly limited as far as not decomposing the Reformatsky reagent, and include, for example, a halogen atom (e.g., fluorine, chlorine, bromine, iodine and the like); $C_{1-6}$ alkoxy which may be halogenated (e.g., methoxy, ethoxy, trifluoromethoxy, 2,2,2-trifluoroethoxy, trichloromethoxy, 2,2,2-trichloroethoxy and the like); and a lower alkyl group (e.g., $C_{1-6}$ alkyl such as methyl, ethyl, propyl, isopropyl, butyl, isobutyl, tert-butyl, pentyl, hexyl and the like) which may be substituted with a substituent selected from $C_{7-11}$ alkylaryl groups (e.g., $C_{1-5}$ alkylphenyl such as o-tolyl, m-tolyl, xylyl, mesityl and the like, and the like); $C_{1-6}$ alkylsulfonyl (e.g., methanesulfonyl and the like), benzenesulfonyl and the like; a $C_{1-6}$ alkoxycarbonyl group which may be halogenated (e.g., methoxycarbonyl, ethoxycarbonyl, trifluoromethoxycarbonyl, 2,2,2-trifluoroethoxycarbonyl, trichloromethoxycarbonyl, 2,2,2-trichloroethoxycarbonyl and the like), a $C_{1-6}$ alkoxycarbonyl group which may be substituted with a phenyl group (e.g., benzyloxycarbonyl and the like); aryl ($C_{6-10}$ aryl such as phenyl, 1-naphthyl, 2-naphthyl and the like); aralkyl (e.g., $C_{7-10}$ aralkyl such as benzyl, phenethyl and the like, preferably phenyl-$C_{1-4}$ alkyl and the like); arylalkenyl (e.g., $C_{8-10}$ arylalkenyl such as cinnamyl and the like, preferably phenyl-$C_{2-4}$ alkenyl and the like); a heterocyclic group (a group similar to the heterocyclic group in "the heterocyclic group which may be substituted" as the above substituent; a nitro group and the like may be used. Any of these substituents may have one to three substituents at positions capable of being substituted.

The above described process is characterized in that zinc exists in an excess amount relative to the compound represented by the general formula (IV). In the above process, zinc is used in a form of, for example, powder, flake, wire, and foil, and particularly zinc is preferably used in a form of powder. In the above process, it is preferable that excess amount of zinc is used relative to one mole amount of the compound represented by the general formula (IV). Specifically, it is preferable that zinc exists in an amount more than 1 gram atom, more preferably more than 1 gram atom and 50 gram atoms or less, further preferably more than 1 gram atom and 5 gram atoms or less, and most preferably more than 1 gram atom and 3 gram atoms or less. It is preferable that zinc is cleaned with an acid or a base before use, but commercial zinc is used without any treatment when the content of the zinc is more than about 95%. Particularly, when commercial zinc is used, it is preferable to use for example chlorotrimethylsilane and the like as an activating agent.

In particular, the present invention provides a process for producing a bromozincacetate compound wherein $R^{11}$ and $R^{12}$ are hydrogen atoms, and $X^1$ is a bromine atom in the formulas (IV) and (V), and more preferably ethyl bromozincacetate wherein $R^{11}$ and $R^{12}$ are hydrogen atoms, $X^1$ is a bromine atom, and $R^{10}$ is an ethyl group in the formulas (IV) and (V).

In the present invention, an organic solvent selected from a group consisting of 2-methyl-tetrahydrofuran, 1,2-dimethoxyethane, cyclopentyl methyl ether and tetrahydrofuran, or a mixed solvent in combination of any two or more of the aforementioned organic solvents are used, preferably tetrahydrofuran, 1,2-dimethoxyethane, or cyclopentyl methyl ether are used, and more preferably, cyclopentyl methyl ether or tetrahydrofuran are used.

It is better that the water content in a solvent used in preparing a Reformatsky reagent is less, and it is particularly preferable that the content is 0.005% or less. Optionally, a stabilizer (2,6-di-t-butyl-4-methyl-phenol and the like) may be added to tetrahydrofuran.

To a mixture of zinc and tetrahydrofuran is added chlorotrimethylsilane and the like in order to activate zinc, and then ethyl bromoacetate (or a solution of tetrahydrofuran) is added dropwise. By controlling a dropping speed of ethyl bromoacetate, a rapid temperature increase is avoided and a mild preparation can be carried out. A supernatant of the resulting mixture or a solution obtained by removing with filtration of insoluble materials may be used in a Reformatsky reaction. Alternatively, the resulting mixture itself may be used in the reaction according to the situation. In a similar way, a compound represented by the general formula (V) may be prepared. In the above process, the reaction temperature is generally −80~150° C., and preferably −10~50° C. The reaction time is generally 1 minute to 20 hours, and preferably 20 minutes to 6 hours.

According to the present invention, when the compound represented by the general formula (IV) is reacted with zinc, an activating agent activating zinc is required. The activating agent which may be used in the present invention includes, for example, halogen, copper halide, silver halide, 1,2-dihaloethane, alkylsilane halide, molecular sieves and the like, wherein halogen represents chlorine, bromine, or iodine.

For the activating agent which may be used in the present invention, particularly alkylsilane halides such as chlorotrimethylsilane and the like are preferable.

Further, the present invention provides a solution of a compound represented by the general formula (V):

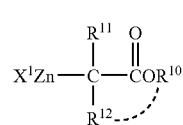

(V)

wherein $X^1$ is a bromine atom or an iodine atom; and $R^{11}$ and $R^{12}$ are, the same or different and independently, a hydrogen atom, an aliphatic hydrocarbon group which may have a substituent, an alicyclic hydrocarbon group which may have a substituent, a heterocyclic group which may have a substituent, an aromatic hydrocarbon group which may have a substituent, an aromatic heterocyclic group which may have a substituent, and $R^{10}$ is an ester residue; or $R^{11}$ is a hydrogen atom, an aliphatic hydrocarbon group which may have a substituent, an alicyclic hydrocarbon group which may have a substituent, a heterocyclic group which may have a substituent, an aromatic hydrocarbon group which may have a substituent, an aromatic heterocyclic group which may have a substituent, and $R^{10}$ and $R^{12}$, taken together with the atom to which they are bonded, form a lactone ring which may have a substituent in 1,2-dimethoxyethane or cyclopentyl methyl ether. Particularly, the present invention provides a solution of ethyl bromozincacetate in 1,2-dimethoxyethan or cyclopentyl methyl ether.

Still further, the present invention provides a process for stabilizing ethyl bromozincacetate by using 1,2-dimethoxyethane or cyclopentyl methyl ether. That is, use of 1,2-dimethoxyethane or cyclopentyl methyl ether as a solvent prevents the compound represented by the general formula (V) from crystallizing to form a stable solution.

EXAMPLES AND REFERENCE EXAMPLES

The following Preparation Examples, Examples and Reference Examples illustrate the present invention in more detail, but the present invention is not limited to them.

Symbols used herein mean as follows: s: singlet, d: doublet, t: triplet, q: quartet, quint: quintet, dd: double doublet, m: multiplet, s br: broad, J: coupling constant, room temperature: 15~30° C., THF: tetrahydrofruan, IPE: isopropyl ether, DME: 1,2-dimethoxyethane, DMF: dimethylformamide Me: $CH_3$—, Et: $CH_3CH_2$—, $^nPr$: $CH_3CH_2CH_2$—, $^tBu$: $(CH_3)_3C$—, Trityl: $(C_6H_5)_3C$—.

Reference Example 1

Preparation of 6-bromo-N-methyl-2-naphthamide

4 Liters of ethyl acetate and 25 mL of DMF were added to 500 g (1.99 mol) of 6-bromo-2-naphthoic acid. 188 mL (2.61 mol, 1.3 eq) of thionyl chloride was added dropwise at 30° C. or lower. The mixture was stirred at 65° C. for 30 minutes. After cooled to 25° C., a mixture of 408 mL (3.93 mol, 2 eq) of a 40% solution of methylamine in methanol and 558 mL (4.01 mol, 2 eq) of triethylamine was added dropwise at 25° C. or lower. The mixture was stirred at 25° C. for 3 hours. 2.5 Liters of water was added dropwise at 25° C. or lower. Crystals were filtered, and washed successively with 1.25 liters of a mixed solution of methanol/water=1/4. Vacuum drying (50° C.) to a constant weight afforded 422 g of 6-bromo-N-methyl-2-naphthamide (yield 80%).

$^1$H NMR (CDCl$_3$+CD$_3$OD): δ 3.04 (3H, s), 7.60 (1H, dd, J=8.6, 1.8 Hz), 7.78 (2H, d, J=8.6 Hz), 7.85 (1H, dd, J=8.6, 1.8 Hz), 8.03 (1H, d, J=1.8 Hz), 8.25 (1H, s).

Reference Example 2

Preparation of 6-[hydroxy(1-trityl-1H-imidazol-4-yl)methyl]-N-methyl-2-naphthamide Under nitrogen atmosphere, 5.8 liters of THF was added to 105.6 g (0.40 mol, 1.2 eq) of 6-bromo-N-methyl-2-naphtamide, the mixture was warmed to 50° C. to dissolve it. 500 mL (0.50 mol, 2.4 eq) of a 1.6 M solution of n-butyllithium in hexane was added dropwise at −65° C. or lower over 35 minutes. The mixture was stirred at −65° C. for 1 hour. A solution of 112.7 g (0.33 mol) of 1-trityl-4-formyl-1H-imidazole in 810 mL of THF was added dropwise at −65° C. or lower over 40 minutes. The mixture was stirred at −65° C. for 2 hours. 1.5 Liters of an aqueous saturated ammonium chloride solution was added dropwise at −20° C. or lower, and the mixture was warmed to 30° C. After separation of the layers, the organic layer was washed with 1.5 liters of an aqueous saturated sodium chloride solution two times. After concentration under reduced pressure, 1 liter of ethyl acetate was added to the residue, and the mixture was stirred at 25° C. for 3 hours. Crystals were filtered, and washed with ethyl acetate. Vacuum drying (50° C.) to a constant weight afforded 87.9 g of 6-[hydroxy(1-trityl-1H-imidazol-4-yl)methyl]-N-methyl-2-naphthamide (yield 50%).

$^1$H NMR (DMSO-d$_6$): δ 2.82 (3H, d, J=4.4 Hz), 5.76 (2H, q, J=6.6 Hz), 6.78 (1H, s), 7.06-7.09 (6H, m), 7.26 (1H, s), 7.33-7.42 (9H, m), 7.53 (1H, d, J=8.5 Hz) 7.88-7.93 (4H, m) 8.36 (1H, s), 8.55 (1H, d, J=4.5 Hz).

Reference Example 3

Preparation of N-methyl-6-[(1-trityl-1H-imidazol-4-yl)carbonyl]-2-naphthamide 2.4 Liters of ethyl acetate and 200 g (2.3 mol, 15 eq) of manganese dioxide were added to 80 g (0.15 mol) of 6-[hydroxy(1-trityl-1H-imidazol-4-yl)methyl]-N-methyl-2-naphthamide. The mixture was stirred at 40~45° C. for 6 hours, filtered with Celite, and the filtered material was washed with 300 mL of ethyl acetate two times. After the filtrate was concentrated under reduced pressure, 200 mL of ethyl acetate and 400 mL of IPE were added to the concentration residue, followed by stirring at 0° C. for 2 hours. Crystals were filtered, and washed with 200 mL of IPE. Vacuum drying (50° C.) to a constant weight afforded 69.8 g of N-methyl-6-[(1-trityl-1H-imidazol-4-yl)carbonyl]-2-naphthamide (yield 88%).

$^1$H NMR (CDCl$_3$): δ 3.07 (3H, d, J=4.8 Hz), 6.39 (1H, d, J=4.7 Hz), 7.11-7.19 (6H, m), 7.30-7.39 (9H, m), 7.57 (1H, d, J=1.2 Hz), 7.81-8.01 (4H, m) 8.29 (2H, dd, J=8.6, 1.4 Hz), 8.99 (1H, s).

Reference Example 4

Preparation of ethyl 3-hydroxy-3-{6-[(methylamino)carbonyl]-2-naphthyl}-3-(1-trityl-1H-imidazol-6-yl)propanoate Under nitrogen atmosphere, 7.1 mL (50.6 mmol, 3 eq) of diisopropylamine was added to 200 mL of THF. At −73~−68° C., 31.6 mL (50.6 mmol, 3 eq) of a 1.6 M solution of n-butyllithium in hexane was added dropwise over 10 minutes. After stirred at 75~−68° C. for 10 minutes, 5 mL of ethyl acetate was added dropwise at −75~−70° C. over 5 minutes. After stirred at −75~−70° C. for 30 minutes, a solution of 8.8 g (16.8 mmol) of N-methyl-6-[(1-trityl-1H-imidazol-4-yl)carbonyl]-2-naphthamide in 22 mL of THF was added dropwise at −75~−65° C. over 5 minutes. After stirred at −75~−65° C. for 30 minutes, the mixture was warmed to −30° C. After stirred for 5 minutes, 50 mL of an aqueous saturated ammonium chloride solution was added dropwise at −70~−40° C., and a temperature was rised to room temperature. After the layers were separated, the aqueous layer was re-extracted with 100 mL of ethyl acetate. The organic layers were combined, and washed with 50 mL of an aqueous saturated sodium chloride solution. After concentration under reduced pressure, 100 mL of n-heptane was added to the concentration residue, followed by stirring at room temperature for 30 minutes. Crystals were filtered, and washed with 50 mL of n-heptane. Vacuum drying (50° C.) to a constant weight afforded 9.82 g of ethyl 3-hydroxy-3-{6-[(methylamino)carbonyl]-2-naphthyl}-3-(1-trityl-1H-imidazol-4-yl)propanoate (yield 96%).

$^1$H NMR (CDCl$_3$): δ 1.13 (3H, t, J=7.1 Hz), 3.05 (3H, d, J=4.8 Hz), 3.33 (2H, dd, J=9.8, 16 Hz), 4.04-4.13 (2H, m), 5.14 (1H, s), 6.35 (1H, brs), 6.84 (1H, d, J=1.5 Hz), 7.07-7.11 (6H, m), 7.26-7.38 (10H, m), 7.69-7.84 (4H, m) 8.03 (1H, s), 8.22 (1H, s).

Example 1

Preparation of 6-[1,3-dihydroxy-1-(1-trityl-1H-imidazol-4-yl)propyl]-N-methyl-2-naphthamide 360 mL of ethanol and 156 mL of THF were added to 26.7 g (0.71 mol, 8eq) of sodium borohydride. 39.3 g (0.35 mol, 4 eq) of calcium chloride was added at 0° C., and the mixture was stirred at 1~3° C. for 30 minutes. A solution of 60 g (98 mmol) of ethyl 3-hydroxy-3-{6-[(methylamino)carbonyl]-2-naphthyl}-3-(1-trityl-1H-imidazol-4-yl)propanoate in 204 mL of THF was added dropwise at 0° C. The mixture was stirred at 0~10° C. for 30 minutes, and at 20~26° C. for 5 hours. 360 mL of water, and 1.44 liters of 1N hydrochloric acid were successively added dropwise. The mixture was stirred at 25° C. for 1 hour. Crystals were filtered, and washed with 500 mL of water two times. Vacuum drying (50° C.) to a constant weight afforded 54.5 g of 6-[1,3-dihydroxy-1-(1-trityl-1H-imidazol-4-yl)propyl]-N-methyl-2-naphthamide (yield 87%).

$^1$H NMR (CDCl$_3$): δ 2.27-2.39 (1H, m), 2.48-2.56 (1H, m), 3.05 (3H, d, J=4.7 Hz), 3.53 (1H, brs), 3.72 (2H, t, J=4.7 Hz), 4.44 (1H, s), 6.38 (1H, d, J=4.4 Hz), 6.79 (1H, s), 7.11-7.14 (6H, m), 7.25-7.41 (10H, m), 7.51 (1H, d, J=8.5 Hz), 7.70-7.76 (3H, m) 7.96 (1H, s), 8.20 (1H, s).

Example 2

Preparation of 6-[1,3-dihydroxy-1-(1-trityl-1H-imidazol-4-yl)propyl]-N-methyl-2-naphthamide Under nitrogen atmosphere, 52.9 mL (0.37 mol, 3 eq) of diisopropylamine was added to 1.3 liters of THF. 234 mL (0.37 mol, 3 eq) of a 1.6 M solution of n-butyllithium in hexane was added dropwise at −65° C. or lower over 23 minutes. After stirred at −65° C. for 20 minutes, 36.6 mL (0.37 mol, 3 eq) of ethyl acetate was added dropwise at −65° C. or lower over 10 minutes. After stirred at −65° C. for 45 minutes, a solution of 65 g (0.13 mol) of N-methyl-6-[(1-trityl-1H-imidazol-4-yl)carbonyl]-2-naphthamide in 260 mL of THF was added dropwise at −65° C. or lower over 25 minutes. The mixture was stirred at −65° C. for 1 hour, and at −4~−30° C. for 2 hours. After 370 mL of an aqueous saturated ammonium chloride solution was added dropwise at −20° C. or lower, the mixture was warmed to 30° C. After the layers were separated, the organic layer was washed with 370 mL of an aqueous saturated ammonium chloride solution two times. Concentration under reduced pressure afforded 102 g of ethyl 3-hydroxy-3-{6-[(methylamino)carbonyl]-2-naphthyl}-3-(1-trityl-1H-imidazol-4-yl)propanoate.

2.9 g (76.6 mol, 8 eq) of sodium borohydride was added to a solution of 5.8 g of ethyl 3-hydroxy-3-{6-[(methylamino)carbonyl]-2-naphthyl}-3-(1-trityl-1H-imidazol-4-yl)propanoate in 40 mL of THF, and 4.25 g (38.2 mol, 4 eq) of calcium chloride was added at 0~5° C. 40 mL of ethanol was added dropwise at 0~5° C. over 15 minutes. The mixture was stirred at 0~5° C. for 30 minutes, and at 40~45° C. for 7 hours. 215 mL of water was added at 25° C., and 76.6 mL of 1N hydrochloric acid was added dropwise. The mixture was stirred at 50~55° C. for 1 hour, and at 25° C. for 4 hours. Crystals were filtered, and washed with 30 mL of water two times. Vacuum drying (50° C.) to a constant weight afforded 5.3 g of 6-[1,3-dihydroxy-1-(1-trityl-1H-imidazol-4-yl)propyl]-N-methyl-2-naphthamide (yield 94%).

$^1$H MNR was consistent with the compound obtained in Example 1.

Example 3

Preparation of 6-[7-hydroxy-6,7-dihydro-5H-pyrrolo[1,2-c]imidazol-7-yl]-N-methyl-2-naphthamide 20 mL of THF and 1.23 mL (3.14 mmol, 2 eq) of diisopropylethylamine were added to 2 g (3.523 mmol) of 6-[1,3- dihydroxy-1-(1-trityl-1H-imidazol-4-yl)propyl]-N-methyl-2-naphtamide. 20 mL of THF was further added. 0.35 mL (4.58 mmol, 1.3 eq) of methylsulfonyl chloride was added dropwise at 2~3° C., and the mixture was stirred at 2~3° C. for 25 minutes. 16 mL of dimethyl sulfoxide was added dropwise at 2~3° C., and the mixture was stirred at 0~3° C. for 45 minutes. 0.2 mL of methylsulfonyl chloride and 0.5 mL of diisopropylethylamine were added at 0~3° C., and the mixture was stirred at 0~3° C. for 20 minutes. 4 mL of water was added dropwise at 0~8° C., and the layers were separated. The aqueous layer was re-extracted with 10 mL of ethyl acetate two times, the organic layers were combined, and washed with 4 mL of an aqueous saturated sodium chloride solution two times. The material was dried with magnesium sulfate, and concentrated under reduced pressure. The concentration residue was dissolved in 15 mL of acetonitrile, and the solution was stirred at 60~63° C. for 20 minutes. To the reaction solution were added 4.5 mL of methanol and 1.23 mL (3.14 mmol, 2 eq) of diisopropylethylamine. The mixture was stirred at 60~63° C. for 2 hours. After cooled to 25° C., 30 mL of an aqueous saturated ammonium chloride solution and 40 mL of ethyl acetate were added, and the layers were separated. The organic layer was back extracted with 10 mL of 0.5N hydrochloric acid-aqueous saturated ammonium chloride solution. The aqueous layers were combined, a pH was adjusted to 8 with a 30% aqueous sodium hydroxide solution, followed by stirring at 25° C. for 18 hours and 15 minutes, and at 0~5° C. for 1 hour and 25 minutes. Crystals were filtered, and washed with water. Vacuum drying (50° C.) to a constant weight afforded 0.87 g. of 6-[7-hydroxy-6,7-dihydro-5H-pyrrolo[1,2-c]imidazol-7-yl]-N-methyl-2-naphthamide (yield 80%).

$^1$H NMR ((CDCl$_3$+CD$_3$OD): δ 2.89-3.02 (2H, m), 3.04 (3H, d, J=4.6 Hz), 4.12-4.25 (1H, m), 4.27-4.43 (1H, m), 6.79 (1H, s), 7.20 (1H, q, J=4.6 Hz), 7.54 (1H, s), 7.63 (1H, dd, J=8.6, 1.8 Hz), 7.83 (2H, s), 7.89 (1H, d, J=8.6 Hz), 8.03 (1H, s), 8.28 (1H, s).

Example 4

Preparation of ethyl(3S)-3-hydroxy-3-{6-[(methylamino)carbonyl]-2-naphthyl}-3-(1-trityl-1H-imidazol-4-yl)propanoate Under argon atmosphere, 10 liters of THF and 253 mL (2 mol) of chlorotrimethylsilane were added to 2616 g (40 mol) of zinc powders. The mixture was stirred at 25° C. for 30 minutes. A solution of 2212 mL (20 mol) of ethyl bromoacetate in 25 L of THF was added dropwise at 25~35° C. 21.2 g (72 mmol, 1.25 eq) of (+)-cinchonine was added to 431 mL (0.23 mol) of the above Reformatsky reagent at 0~5° C. 18.6 mL (230 mmol, 4 eq) of pyridine was added dropwise at 0~5° C. over 7 minutes. The mixture was stirred at 0~5° C. for 20 minutes. A solution of 30 g (57.5 mmol) of N-methyl-6-[(1-trityl-1H-imidazol-4-yl)carbonyl]-2-naphthamide in 300 mL of THF was added dropwise at −42~−40° C. over 30 minutes. The mixture was stirred at −45~−40° C. for 1 hour. 430 mL of 1N hydrochloric acid was added dropwise, diluted with 430 mL of ethyl acetate, and stirred at 20~25° C. for 30 minutes.

After the layers were separated, the organic layer was washed successively with 290 mL of 1N hydrochloric acid, 290 mL of water and 290 mL of an aqueous saturated sodium bicarbonate solution two times, and 290 mL of an aqueous saturated sodium chloride solution. After concentrated under reduced pressure, 90 mL of ethyl acetate was added to the concentration residue, and the mixture was warmed to 50° C. to dissolve it. The solution was stirred at 20~25° C. for 1 hour.

90 mL of IPE was added, followed by stirring at 0~5° C. for 2 hours. Crystals were filtered, and washed with 30 mL of IPE. Vacuum drying (50° C.) to a constant weight afforded 29.2 g of ethyl (3S)-3-hydroxy-3-{6-[(methylamino)carbonyl]-2-naphthyl}-3-(1-trityl-1H-imidazol-4-yl)propanoate (yield 83%, enantiomer excess 93.5% ee).

$^1$H NMR (CDCl$_3$): δ 1.13 (3H, t, J=7.1 Hz), 3.05 (3H, d, J=4.8 Hz), 3.33 (2H, dd, J=98, 16 Hz), 4.04-4.13 (2H, m), 5.14 (1H, s), 6.35 (1H, brs), 6.84 (1H, d, J=1.5 Hz), 7.07-7.11 (6H, m), 7.26-7.38 (10H, m), 7.69-7.84 (4H, m) 8.03 (1H, s), 8.22 (1H, s).

Example 5

Preparation of 6-[(1S)-1,3-dihydroxy-1-(1-trityl-1H-imidazol-4-yl)propyl]-N-methyl-2-naphthamide 13 mL of THF was added to 1.3 g (2.13 mmol) of ethyl (3S)3-hydroxy-3-{6-[(methylamino)carbonyl]-2-naphthyl}-3-(1-trityl-1H-imidazol-4-yl)propanoate, and 0.645 g (17.1 mmol, 8 eq) of sodium borohydride was added. 0.95 g (8.53 mmol, 4 eq) of calcium chloride was added at 2° C. 13 mL of ethanol was added dropwise at 2° C. over 15 minutes. The mixture was stirred at 3~4° C. for 30 minutes, and at 40~43° C. for 4 hours. 56 mL of water was added dropwise. 17.1 mL of 1N hydrochloric acid was added dropwise, followed by dilution with 40 mL of ethyl acetate. Then, the layers were separated. The aqueous layer was re-extracted with 20 mL of ethyl acetate. The organic layers were combined, and washed with 20 mL of an aqueous saturated sodium chloride solution two times. After concentration under reduced pressure, IPE was added to the concentration residue, crystals were loosened, filtered and washed with IPE. Vacuum drying (50° C.) to a constant weight afforded 1.08 g of 6-[(1S)-1,3-dihydroxy-1-(1-trityl-1H-imidazol-4-yl)propyl]-N-methyl-2-naphthamide (yield 89%, enantiomer excess 92.0% ee).

$^1$H NMR (CDCl$_3$): δ 2.27-2.39 (1H, m), 2.48-2.56 (1H, m), 3.05 (3H, d, J=4.7 Hz), 3.53 (1H, brs), 3.72 (2H, t, J=4.7 Hz), 4.44 (1H, s), 6.38 (1H, d, J=4.4 Hz), 6.79 (1H s), 7.11-7.14 (6H, m), 7.25-7.41 (10H, m), 7.51 (1H, d, J=8.5 Hz), 7.70-7.76 (3H, m) 7.96 (1H, s), 8.20 (1H, s).

Example 6

Preparation of 6-[(1S)-1,3-dihydroxy-1-(1-trityl-1H-imidazol-4-yl)propyl]-N-methyl-2-naphthamide 0.095 g (2.51 mmol, 8 eq) of sodium borohydride was added to 1.3 mL of ethanol and 1.3 mL of THF. 0.14 g (1.26 mmol, 4 eq) of calcium chloride was added at 0~5° C., and the mixture was stirred at the same temperature for 30 minutes. 0.188 g (0.314 mmol) of methyl (3S)-3-hydroxy-3-{6-[(methylamino)carbonyl]-2-naphthyl}-3-(1-trityl-1H-imidazol-4-yl)propanoate was added at 0~5° C., and the mixture was stirred for 30 minutes. The mixture was stirred at room temperature for 4.5 hours. 7 mL of water was added dropwise at 35° C. or lower. 2.5 mL of 1N hydrochloric acid was added dropwise, followed by dilution with 10 mL of ethyl acetate. Then, the layers were separated. The organic layer was washed successively with 2 mL of an aqueous saturated sodium bicarbonate solution and 2 mL of an aqueous saturated sodium chloride solution. After concentrated under reduced pressure, the concentration residue was loosened with 2 mL of IPE, crystals were filtered, and washed with 1 mL of IPE. Vacuum drying (40° C.) to a constant weight afforded 0.16 g of 6-[(1S)-1,3-dihydroxy-1-(1-trityl-1H-imidazol-4-yl)propyl]-N-methyl-2-naphthamide (yield 90%).

¹H NMR was consistent with the compound obtained in Example 5.

Example 7

Preparation of 6-[(7S)-hydroxy-6,7-dihydro-5H-pyrrolo[1,2-c]imidazol-7-yl]-N-methyl-2-naphthamide 7 mL of THF and 0.42 mL (2.47 mmol, 4 eq) of diisopropylethylamine were added to 0.35 g (0.62 mmol) of 6-[(1S)-1,3-dihydroxy-1-(1-trityl-1H-imidazol-4-yl)propyl]-N-methyl-2-naphthamide. 0.072 mL (0.93 mmol, 1.5 eq) of methylsulfonyl chloride was added dropwise at 0~5° C., and the mixture was stirred at 0~5° C. for 40 minutes. 1.8 mL of methanol and 3.5 mL of acetonitrile were added, and the mixture was stirred at 60~65° C. for 4 hours. After cooled to 25° C., 7 mL of ethyl acetate was added, 3.5 mL of 0.5N hydrochloric acid-aqueous saturated ammonium chloride solution was added dropwise at 0~5° C., and 1 mL of water was added. The aqueous layer was taken, and the organic layer was back extracted with 2 mL of 0.5N hydrochloric acid-aqueous saturated ammonium chloride solution two times.

The aqueous layers were combined, and a pH was adjusted to 8 with a 1N aqueous sodium hydroxide solution. The material was stirred at 25° C. for 2 hours, and at 0~5° C. for 2 hours. Crystals were filtered, and washed with water. Vacuum drying (50° C.) to a constant weight afforded 0.87 g of 6-[(7S)-hydroxy-6,7-dihydro-5H-pyrrolo[1,2-c]imidazol-7-yl]-N-methyl-2-naphthamide (yield 62%, enantiomer excess 98.2% ee).

¹H NMR ((CDCl₃+CD₃OD): δ 2.89-3.02 (2H, m), 3.04 (3H, d, J=4.6 Hz), 4.12-4.25 (1H, m), 4.27-4.43 (1H, m), 6.79 (1H, s), 7.20 (1H, q, J=4.6 Hz), 7.54 (1H, s), 7.63 (1H, dd, J=8.6, 1.8 Hz), 7.83 (2H, s), 7.89 (1H, d, J=8.6 Hz), 8.03 (1H, s), 8.28 (1H, s).

Example 8

Preparation of 6-[(1S)-1,3-dihydroxy-1-(1-trityl-1H-imidazol-4-yl)propyl]-N-methyl-2-naphthamide Under argon atmosphere, 8 mL of THF and 0.15 mL (1.18 mmol) of chlorotrimethylsilane were added to 1.04 g (16 mmol) of zinc powders, and the mixture was stirred at 35~40° C. for 5 hours. A solution of 2.36 mL (16 mmol) of tent-butyl bromoacetate in 20 mL of THF was added dropwise at 45~52° C. over 10 minutes. The mixture was stirred at 65~67° C. for 1 hour, and cooled to 25° C. 8.5 mL of THF was added to 1.32 g (4.5 mmol, 1.25 eq) of (+)-cinchonine. The 25. above Reformatsky reagent was added dropwise at 4~6° C. for 15 minutes. 1.16 mL (14.4 mmol, 4 eq) of pyridine was added dropwise at 5~7° C. over 2 minutes. The mixture was stirred at 5~6° C. for 30 minutes. A solution of 1.88 g (3.6 mmol) of N-methyl-6-[(1-trityl-1H-imidazol-4-yl)carbonyl]-2-naphthamide in 15 mL of THF was added dropwise at −44~−39° C. over 7 minutes. The mixture was stirred at −44~−35° C. for 5 hours and 20 minutes. 10 mL of 1N hydrochloric acid was added dropwise, and warmed to 0° C. The mixture was diluted with 50 mL of ethyl acetate, 10 mL of 1N hydrochloric acid was added, and the layers were separated. The organic layer was washed successively with 20 mL of 1N hydrochloric acid two times, 20 mL of water, 20 mL of an aqueous saturated sodium bicarbonate solution. To the organic layer were added 10 mL of 0.1N hydrochloric acid, 10 mL of water and 10 mL of ethyl acetate, and the layers were separated. The organic layer was washed with 20 mL of an aqueous saturated sodium chloride solution, and concentrated under reduced pressure at 20° C. 10 mL of n-hexane was added to the concentration residue, crystals were loosened, filtered, and washed with 10 mL of n-hexane.

Air-drying to a constant weight afforded 2.48 g of tert-butyl (3S)-3-hydroxy-3-{6-[(methylamino)carbonyl]-2-naphthyl}-3-(1-trityl-1H-imidazol-4-yl)propanoate (enantiomer excess 95.0% ee).

¹H NMR (CDCl₃): δ 1.30 (9H, s), 3.05 (3H, d, J=4.8 Hz), 3.25 (2H, dd, J=80, 16 Hz), 5.26 (1H, s), 6.34 (1H, d, J=4.7 Hz), 6.87 (1H, d, J=1.5 Hz), 7.07-7.11 (6H, m), 7.25-7.37 (10H, m), 7.70-7.84 (4H, m) 8.04 (1H, s), 8.21 (1H, s).

6.5 mL of ethanol and 6.5 mL of THF were added to 0.47 g (12.5 mmol, 8 eq) of sodium borohydride. 0.7 g (6.27 mmol, 4 eq) of calcium chloride was added at 4~5° C., and the mixture was stirred at 4~5° C. for 35 minutes. 1 g (1.57 mmol) of tert-butyl (3S)-3-hydroxy-3-{6-[(methylamino)carbonyl]-2-naphthyl}-3-(1-trityl-1H-imidazol-4-yl)propanoate was added at 5° C. The mixture was stirred at 23~29° C. for 6 hours. 35 mL of water was added dropwise. 12.5 mL of 1N hydrochloric acid was added dropwise, diluted with 20 mL of ethyl acetate, and the layers were separated. The aqueous layer was re-extracted with 20 mL of ethyl acetate. The organic layers were combined, and washed successively with 10 mL of water and 10 mL of an aqueous saturated sodium chloride solution. After concentrated under reduced pressure, the concentration residue was dissolved in 1 mL of ethanol, and allowed to stand overnight. Crystals were filtered, and washed with 0.2 mL of ethanol. The filtrate was concentrated under reduced pressure, 0.5 mL of ethyl acetate and 1 mL of IPE were added to the concentration residue, crystals were loosened, filtered, and washed with 0.75 mL of ethyl acetate/IPE=1/10.75 ml. Vacuum drying (40° C.) to a constant weight afforded 0.5 g of 6-[(1S)-1,3-dihydroxy-1-(1-trityl-1H-imidazol-4-yl)propyl]-1H-methyl-2-naphthamide (yield 61%).

¹H NMR was consistent with the compound obtained in Example 5.

Example 9

Preparation of isopropyl(3S)-3-hydroxy-3-{6-[(methylamino)carbonyl]-2-naphthyl}-3-(1-trityl-1H-imidazol-4-yl)propanoate 50 mL of 0.1N hydrochloric acid was added to 5 g of zinc powders, the mixture was stirred vigorously for 10 minutes, filtered, and washed successively with 30 mL of water, 30 mL of ethanol, and 30 mL of ether. Zinc was filtered, followed by vacuum drying at 100° C. for 8 hours. Under argon atmosphere, 4 mL of THF and 0.075 mL (0.59 mmol) of chlorotrimethylsilane were added to 0.52 g (8 mmol) of the zinc powders. The mixture was stirred at 25~28° C. for 2 minutes, and a solution of 1.04 mL (8 mmol) of isopropyl bromoacetate in 10 mL of THF was added over 10 minutes. The mixture was stirred at 45~50° C. for 45 minutes. A solution of 0.94 g (1.8 mmol) of N-methyl-6-[(1-trityl-1H-imidazol-4-yl)carbonyl]-2-naphthamide in 7.5 mL of THF was added dropwise at −33~35° C. over 5 minutes. The mixture was stirred at −43~35° C. for 30 minutes, at 15~25° C. for 3 hours, and at 45~50° C. for 50 minutes. 5 mL of 1N hydrochloric acid was added dropwise at 25° C., diluted with 25 mL of ethyl acetate, 5 mL of 1N hydrochloric acid was added, and the layers were separated. The organic layer was washed successively with 5 mL of 1N hydrochloric acid two times, 10 mL of water, 5 mL of an aqueous saturated sodium bicarbonate solution, and 5 mL of an aqueous saturated sodium chloride solution. After concentrated under reduced pressure, 2 mL of ethyl acetate was added to the concentration residue. Crystals were filtered, and washed with 1 mL of ethyl acetate. Vacuum drying (40° C.) to a constant weight afforded 0.78 g of isopropyl(3S)-3-hydroxy-3-{6-[(methylamino)carbonyl]-2-naphthyl}-3-(1-trityl-1H-imidazol-4-yl)propanoate (yield 70%).

$^1$H NMR (CDCl$_3$): δ 1.06 (3H, d, J=6.3 Hz), 1.13 (3H, d, J=6.3 Hz), 3.06 (3H, d, J=4.8 Hz), 3.30 (2H, dd, J=86, 16 Hz), 4.93 (1H, quint, J=6.3 Hz), 5.20 (1H, s), 6.33 (1H, d, J=4.1 Hz), 6.84 (1H, d, J=1.3 Hz), 7.07-7.11 (6H, m), 7.26-7.39 (10H, m), 7.71-7.83 (4H, m), 8.02 (1H, s), 8.21 (1H, s).

Example 10

Preparation of 6-[1,3-dihydroxy-1-(1-trityl-1H-Imidazol-4-yl)propyl]-N-methyl-2-naphthamide 3 mL of THF and 0.17 g (1.25 mmol, 8 eq) of zinc chloride were added to 0.095 g (2.51 mmol, 8 eq) of sodium borohydride. The mixture was stirred at 25° C. for 10 minutes. 0.2 g (0.31 mmol) of isopropyl (3S)-3-hydroxy-3-{6-[(methylamino)carbonyl]-2-naphthyl}-3-(1-trityl-1H-imidazol-4-yl)propanoate was added. The mixture was stirred at 40° C. for 31 hours. After cooled to 25° C., 3 droplets of water was added dropwise, 11 mL of water, 1 mL of an aqueous saturated ammonium chloride solution and 12 mL of ethyl acetate were added, and the layers were separated. The organic layer was washed successively with a mixed solution of 1 mL of an aqueous saturated ammonium chloride solution and 8 mL of water, and 8 mL of water 2 times. After concentrated under reduced pressure, the concentration residue was loosened with 4 mL of water, and crystals were filtered. Vacuum drying (40° C.) to a constant weight afforded 0.15 g of 6-[1,3-dihydroxyl-1-(1-trityl-1H-imidazol-4-yl)propyl]-N-methyl-2-naphthamide (yield 76%).

$^1$H NMR was consistent with the compound obtained in Example 1.

Example 11

Preparation of 6-[(1S)-1,3-dihydroxy-1-(1-trityl-1H-imidazol-4-yl)propyl]-N-methyl-2-naphthamide 8 mL of THF and 0.15 mL (1.18 mmol) of chlorotrimethylsilane were added to 1.04 g (16 mmol) of zinc powders, and the mixture was stirred at 35~40° C. for 5 minutes. A solution of 2.36 mL (16 mmol) of tert-butyl bromoacetate in 20 mL of THF was added dropwise at 45~52° C. over 10 minutes. The mixture was stirred at 65~67° C. for 1 hour, and cooled to 25° C. 8.5 mL of THF was added to 1.32 g (4.5 mmol, 1.25 eq) of (+)-cinchonine. The above Reformatsky reagent was added dropwise at 4~6° C. over 15 minutes. 1.16 mL (14.4 mmol, 4 eq) of pyridine was added dropwise at 5~7° C. over 2 minutes. The mixture was stirred at 5~6° C. for 30 minutes. A solution of 1.88 g (3.6 mmol) of N-methyl-6-[(1-trityl-1H-imidazol-4-yl)carbonyl]-2-naphthamide in 15 mL of THF was added dropwise at −44~−39° C. over 7 minutes. The mixture was stirred at −44~−35° C. for 5 hours and 20 minutes. 10 mL of 1N hydrochloric acid was added, and the mixture was warmed to 0° C. The mixture was diluted with 50 mL of ethyl acetate, 10 mL of 1N hydrochloric acid was added, and the layers were separated. The organic layer was washed successively with 20 mL of 1N hydrochloric acid 2 times, 20 mL of water, and 20 mL of an aqueous saturated sodium bicarbonate solution. To the organic layer were added 10 mL of 0.1N hydrochloric acid, 10 mL of water and 10 mL of ethyl acetate, and the layers were separated. The organic layer was washed with 20 mL of an aqueous saturated sodium chloride solution, and concentrated at 20° C. or lower under reduced pressure. 10 mL of n-hexane was added to the concentration residue, crystals were loosened, filtered, and washed with 10 mL of n-hexane. Air drying to a constant weight afforded 2.48 g of tert-butyl(3S)-3-hydroxy-3-{6-[(methylamino)carbonyl]-2-naphthyl}-3-(1-trityl-1H-imidazol-4-yl)propanoate (enantiomer excess 95.0% ee).

15 mL of THF was added to 0.47 g (12.5 mmol, 8 eq) of sodium borohydride. 0.85 g (6.27 mmol, 4 eq) of zinc chloride was added at 30° C., and the mixture was stirred at 35~37° C. for 15 minutes. 1 g (1.57 mmol) of tert-butyl (3S)-3-hydroxy-3-{6-[(methylamino)carbonyl]-2-naphthyl}-3-(1-trityl-1H-imidazol-4-yl)propanoate was added at 35° C. The mixture was stirred at 45~49° C. for 24 hours and 30 minutes. 5 mL of water was added dropwise at 35° C. or lower. 15 mL of water and 5 mL of an aqueous saturated ammonium chloride solution were added, and the mixture was stirred at 20~25° C. for 6 hours. After diluted with 50 mL of ethyl acetate, 10 mL of ethanol and 10 mL of water, insoluble materials were filtered. The filtrate was separated, and the organic layer was washed successively with 20 mL of water and 20 mL of an aqueous saturated sodium chloride solution. After concentrated under reduced pressure, 1 mL of ethyl acetate and 2 mL of IPE were added to the concentration residue, crystals were loosened, filtered, and washed with 1.25 mL of ethyl acetate/IPE=1/1 two times. Vacuum drying (40° C.) to a constant weight afforded 0.48 g of 6-[(1S)-1,3-dihydroxy-1-(1-trityl-1H-imidazol-4-yl)propyl]-N-methyl-2-naphthamide (yield 58%).

$^1$H MMR was consistent with the compound obtained in Example 5.

Example 12

Preparation of 6-[1,3-dihydroxy-1-(1-trityl-1H-imidazol-4-yl)propyl]-N,N-diisopropyl-2-naphthamide 1.5 mL of ethanol and 1.5 mL of THF were added to 0.11 g (2.94 mmol, 8 eq) of sodium borohydride. 0.16 g (1.47 mmol, 4 eq) of calcium chloride was added at 0° C., and the mixture was stirred at 0~3° C. for 25 minutes. 0.25 g (0.37 mmol) of ethyl 3-{6-[(diisopropylamino)carbonyl]-2-naphthyl}-3-hydroxy-3-(1-trityl-1H-imidazol-4-yl)propanoate was added at 0° C. The mixture was stirred at 20~23° C. for 8 hours and 15 minutes. 13 mL of water was added dropwise, and the mixture was stirred at 25° C. for 15 minutes. Crystals were filtered, and washed with water. Vacuum drying (50° C.) to a constant weight afforded 0.21 g of 6-[1,3-dihydroxy-1-(1-trityl-1H-imidazol-4-yl)propyl]-N,N-diisopropyl-2-naphthamide (yield 90%).

$^1$H NMR (CDCl$_3$): δ 1.34 (12H, br s), 2.27-2.40 (1H, m), 2.48-2.61 (1H, m), 3.70 (2H, t, J=5.0 Hz), 3.83 (3H, br s), 4.54 (1H, s), 6.78 (1H, d, J=1.6 Hz), 7.08-7.17 (6H, m), 7.28-7.40 (11H, m), 7.51 (1H, dd, J=8.4, 1.8 Hz), 7.71-7.81 (3H, m), 7.97 (1H, s).

Reference Example 5

Preparation of ethyl(3S)-3-hydroxy-3-{6-[(methylamino)carbonyl]-2-naphthyl}-3-(1-trityl-1H-imidazol-4-yl)propanoate Under argon atmosphere, a solution of 8.44 mL (76.5 mmol) of ethyl bromoacetate in 35 mL of THF was added to a solution of 5 g of Rieke-Zn in 105 mL of THF at 19~21° C.

over 20 minutes. The mixture was stirred at 20~25° C. for 20 minutes, and allowed to stand for 3 hours and 30 minutes. 1.26 g (4.3 mmol, 1.25 eq) of (+)-cinchonine was added to 30 mL of the above Reformatsky reagent at 8° C. 1.1 mL (13.8 mmol, 4 eq) of pyridine was added dropwise at 5~7° C. The mixture was stirred at 4~7° C. for 15 minutes, and a solution of 1.79 g (3.4 mmol) of N-methyl-6-[(1-trityl-1H-imidazol-4-yl)carbonyl]-2-naphthamide in 15 mL of THF was added dropwise at −8~−6° C. The mixture was stirred at −10~−8° C. for 2 hours and 30 minutes. 10 mL of 1N hydrochloric acid was added dropwise, and the mixture was warmed to 0° C. After diluted with 50 mL of ethyl acetate, 10 mL of 1N hydrochloric acid was added, and the layers were separated.

The organic layer was washed successively with 20 mL of 1N hydrochloric acid two times, 20 mL of water, 20 mL of an aqueous saturated sodium bicarbonate solution, and 20 mL of an aqueous saturated sodium chloride solution. After concentrated under reduced pressure, 4 mL of ethyl acetate and 2 mL of IPE were added to the concentration residue. Crystals were filtered, and washed with 2 mL of ethyl acetate three times. Vacuum drying (40° C.) to a constant weight afforded 1.41 g of ethyl (3S)-3-hydroxy-3-{6-[(methylamino)carbonyl]-2-naphtyl}-3-(1-trityl-1H-imidazol-4-yl)propanoate(yield 68%, enantiomer excess 63.1% ee).

$^1$H NMR was consistent with the compound obtained in Example 4.

Reference Example 6

Preparation of ethyl (3S)-3-hydroxy-3-{6-[(methylamino)carbonyl]-2-naphthyl}-3-(1-trityl-1H-imidazol-4-yl)propanoate 150 mL of ethanol and 6.9 mL (23.5 mmol, 3 eq) of titanium tetraisopropoxide were added to 5 g (7.84 mmol) of tert-butyl (3S)-3-hydroxy-3-{6-[(methylamino)carbonyl]-2-naphtyl}-3-(1-trityl-1H-imidazol-4-yl)propanoate. The mixture was stirred at 60~65° C. for 28 hours and 40 minutes. 50 mL of 1N hydrochloric acid was added to at 0~10° C., followed by dilution with 150 mL of ethyl acetate. 50 mL of an aqueous saturated sodium chloride solution was added, and the layers were separated. The organic layer was washed successively with a mixed solution of 25 mL of 1N hydrochloric acid and 65 mL of an aqueous saturated sodium chloride solution two times, 25 mL of an aqueous saturated sodium bicarbonate solution, and 50 mL of an aqueous saturated sodium chloride solution two times. After concentrated under reduced pressure, 50 mL of ethyl acetate, 10 mL of THF and 10 mL of water were added to the concentration residue and the layers were separated. The organic layer was washed with 10 mL of an aqueous saturated sodium chloride solution two times. After concentrated under reduced pressure, 15 mL of IPE was added to the concentrated residue, crystals were loosened, filtered, and washed with 5 mL of. IPE two times. Vacuum drying (40° C.) to a constant weight afforded 3.8 g of ethyl (3S)-3-hydroxy-3-{6-[(methylamino)carbonyl]-2-naphtyl}-3-(1-trityl-1H-imidazol-4-yl)propanoate (yield 80%, enantiomer excess 94.8% ee).

$^1$H NMR was consistent with the compound obtained in Example 4.

Further, a Reformatsky reagent in a stable form useful for a Reformatsky reaction which is used in STEP 04 of synthesizing a steroid $C_{17,20}$ lyase inhibitor of the present invention was synthesized.

Example 13

Preparation of ethyl bromozincacetate.THF binuclear complex crystal ((BrZnCH$_2$COOEt.THF)$_2$)

Under argon atmosphere, 200 mL of THF and 5 mL (39.4 mmol) of chlorotrimethylsilane were added to 52.3 g (0.8 gram atoms) of zinc powders, and the mixture was stirred at 20~25° C. for 30 minutes. A solution of 44.4 mL (0.4 mol) of ethyl bromoacetate in 500 mL of THF was added dropwise at 22~45° C. The mixture was stirred at 32~45° C. for 1 hour, and allowed to cool to 25° C.

After cooling, zinc was removed by filtration under nitrogen atmosphere, followed by washing with 150 mL of THF. The filtrate was concentrated to about 150 mL under reduced pressure (crystals precipitated). After stirring under ice-cooling, crystals were filtered at nitrogen pressure. After washing with 20 mL of THF, nitrogen was supplied to completion of removal of a liquid to obtain 88.9 g of ethyl bromozincacetate THF binuclear complex crystals ((BrZnCH$_2$COOEt.THF)$_2$) (white crystals, yield 73%).

$^1$H NMR (DMSO-d6), (ppm): δ 1.10 (6H, t, J=7.1 Hz), 1.20 (4H, s), 1.74-1.82 (8H, m), 3.54-3.66 (8H, m), 3.84 (4H, q, J=7.1 Hz).

$^{13}$C NMR (DMSO-d$_6$), (ppm): δ 177.7, 67.3, 57.5, 25.4, 19.6, 15.0.

$^1$H NMR (pyridine-d$_5$), (ppm): δ 1.06 (6H, t, J=7.1 Hz), 1.86 (4H, s), 1.57-1.69 (8H, m), 3.59-3.72 (8H, m), 4.07 (4H, q, J=7.1 Hz).

NMR (pyridine-d$_5$), (ppm): δ 179.4, 67.6, 58.0, 25.6, 18.7, 14.7.

$^1$H NMR (THF-d$_8$), (ppm): δ 1.17 (6H, t, J=7.1 Hz), 1.86 (4H, s), 1.69-1.79 (8H, m), 3.54-3.64 (8H, m), 4.04 (4H, q, J=7.1Hz).

$^{13}$C NMR (THF-d$_8$), (ppm): δ 187.0, 68.2, 61.6, 22.0, 61.6, 14.7.

FT-IR (Micro-ATR method) (cm$^{-1}$): 3512, 2983, 2897, 1736, 1695, 1589, 1446, 1371, 1286, 1244, 1070, 1022, 918, 858, 769.

Example 14

X-Ray Crystallographic Structural Analysis of ethyl bromozincacetate.THF binuclear complex crystal ((BrZnCH$_2$COOEt.THF)$_2$)

A structure of the resulting ethyl bromozincacetate.THF binuclear complex crystal ((BrZnCH$_2$COOE.THF)$_2$) was analyzed by X-ray crystallography. This confirmed that this crystal has a structure shown in FIG. 1. Bond lengths and bond angles in this structure are shown in Table 1 and Table 2, and crystallographic data and precise structural data are shown in Table 3.

TABLE 1

Bond Lengths for Crystal of Ethyl Bromozincacetate•THF Binuclear Complex ((BrZnCH$_2$COOEt•THF)$_2$)

| BOND LENGTH | (Å) |
|---|---|
| Br(1)—Zn(2) | 2.334 |
| Zn(2)—O(5) | 2.029 |
| C(3)—C(4) | 1.21 |
| C(4)—O(6) | 1.33 |
| C(7)—C(8) | 1.41 |
| C(9)—C(13) | 1.42 |
| C(11)—C(12) | 1.37 |

TABLE 1-continued

Bond Lengths for Crystal of Ethyl Bromozincacetate•THF Binuclear Complex ((BrZnCH$_2$COOEt•THF)$_2$)

| BOND LENGTH | (Å) |
|---|---|
| Zn(2)—C(3) | 1.996 |
| Zn(2)—O(9) | 2.049 |
| C(4)—O(5) | 1.47 |
| O(6)—C(7) | 1.46 |
| O(9)—C(10) | 1.42 |
| C(10)—C(11) | 1.49 |
| C(12)—C(13) | 1.42 |

TABLE 2

Bond Angles for Crystal of Ethyl Bromozincacetate•THF Binuclear Complex ((BrZnCH$_2$COOEt•THF)$_2$)

| BOND ANGLE | (°) |
|---|---|
| Br(1)—Zn(2)—C(3) | 112.4 |
| Br(1)—Zn(2)—O(9) | 105.0 |
| C(3)—Zn(2)—O(9) | 91.3 |
| Zn(2)—C(3)—C(4) | 129.6 |
| C(3)—C(4)—O(6) | 120.6 |
| Zn(2)—O(5)—C(4) | 108.1 |
| O(6)—C(7)—C(8) | 111 |
| Zn(2)—O(9)—C(13) | 122.8 |
| O(9)—C(10)—C(11) | 104 |
| C(11)—C(12)—C(13) | 109 |
| Br(1)—Zn(2)—O(5) | 122.5 |
| C(3)—Zn(2)—O(5) | 109.9 |
| O(5)—Zn(2)—O(9) | 111.2 |
| C(3)—C(4)—O(5) | 125 |
| O(5)—C(4)—O(6) | 113 |
| C(4)—O(6)—C(7) | 116 |
| Zn(2)—O(9)—C(10) | 122.6 |
| C(10)—O(9)—C(13) | 109.7 |
| C(10)—C(11)—C(12) | 108 |
| O(9)—C(13)—C(12) | 106 |

TABLE 3

Crystallographic Data and Structure Refinenment

| | |
|---|---|
| Molecular Formula | C$_8$H$_{15}$BrO$_3$Zn |
| Formula Weight | 304.49 |
| Crystal Color, Habit | colorless, prismatic |
| Crystal System | monoclinic |
| Lattice Parameters | a = 19.93(1) Å |
| | b = 8.347(7) Å |
| | c = 17. 860(8) Å |
| | β = 125.94(3) |
| | V = 2405(2) Å$^3$ |
| Space Group | C2/c(#15) |
| Z Value | 8 |
| D$_{calc}$ | 1.682 g/cm$^3$ |
| No. of Independent Reflections | 2074 (R$_{int}$ = 0.086) |
| No. of Observed Reflections | 1509 |
| No. of Variables | 118 |
| Residuals: R; R$_w$ | 0.079; 0.233 |
| Goodness of Fit Indicator | 1.04 |
| Max Shift/Error in Final Cycle | 0.00 |
| Maximum peak in Final Diff. Map | 1.21e$^-$/Å$^3$ |
| Minimum peak in Final Diff. Map | −1.40e$^-$/Å$^3$ |

Example 15

Preparation of ethyl bromozincacetate.THF binuclear complex crystal ((BrZnCH$_2$COOEt.THF)$_2$)

Under argon atmosphere, 100 mL of cyclopentyl methyl ether and 5.1 mL (40 mmol) of chlorotrimethylsilane were added to 52.3 g (0.8 gram atoms) of zinc powders, and the mixture was stirred at 20~25° C. for 20 minutes. A solution of 42.2 mL (0.4 mol) of ethyl bromoacetate in 250 mL of cyclopentyl methyl ether was added dropwise at 30~40° C. The mixture was stirred at 30~40° C. for 30 minutes, and allowed to cool to 25° C.

After cooling, zinc was removed by filtration under nitrogen atmosphere. 65 mL (0.80 mmol) of THF was added dropwise to the filtrate at 0~10° C. to precipitate crystals. After stirred for 2 hours, crystals were filtered under nitrogen pressure. After washed with 40 mL of cyclopentyl methyl ether, nitrogen was supplied until completion of removal of a liquid, to obtain 113 g of ethyl bromozincacetate.THF binuclear complex crystal ((BrZnCH$_2$COOEt.THF)$_2$) (white crystals, yield corrected based on contained solvent 75.0%.

$^1$H NMR was consistent with the compound obtained in Example 13.

Example 16

Preparation of ethyl 3-hydroxy-3-phenylpropanoate

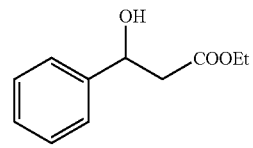

Under nitrogen atmosphere, 30 mL of THF was added to 3.96 g (6.50 mmol, 0.65 equivalent (equivalent relative to a carbonyl compound as a starting raw material; the same, hereinafter)) of (BrZnCH$_2$COOEt.THF)$_2$. Under argon atmosphere, a solution of 1.06 g (10 mmol) of benzaldehyde in 5 mL of THF was added dropwise while stirring at 0~5° C. The mixture was stirred at 0~5° C. for 3 hours. 25 mL of 1N hydrochloric acid was added dropwise at 20° C. or lower, followed by dilution with 50 mL of ethyl acetate. Then, the layers were separated. The organic layer was washed successively with 10 mL (×2) of 1N hydrochloric acid, 20 mL of an aqueous saturated sodium chloride solution, 20 mL (×2) of an aqueous saturated sodium bicarbonate solution and 20 mL of an aqueous saturated sodium chloride solution.

After washing, the organic layer was dried with anhydrous magnesium sulfate. Concentration under reduced pressure afforded 1.76 g of the desired product (yield 91%).

$^1$H NMR (CDCl$_3$), (ppm): δ 1.27 (3H, t, J=7.1 Hz), 2.67-2.82 (2H, m), 3.26 (1H, d, J=3.4 Hz), 4.19 (2H, q, J=7.1 Hz), 5.14 (1H, quint, J=4.0 Hz), 7.27-7.40 (5H, m).

Example 17

Preparation of ethyl 3-(2-furyl)-3-hydroxypropanoate

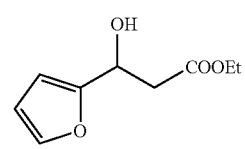

Under nitrogen atmosphere, 30 mL of THF was added to 6.09 g (10 mmol, 1.0 equivalent) of (BrZnCH$_2$COOEt.THF)$_2$. Under argon atmosphere, a solution of 0.96 g (10 mmol) of 2-furfural in 5 mL of THF was added dropwise while stirring at 0~5° C. The mixture was stirred at 0~5° C. for 3 hours. 25 mL of 1N hydrochloric acid was added dropwise at 20° C. or lower, followed by dilution with 50 mL of ethyl acetate. Then, the layers were separated. The organic layer was washed successively with 10 mL of 1N hydrochloric acid, 20 mL of an aqueous saturated sodium chloride solution, 20 mL (×3) of an aqueous saturated sodium bicarbonate solution, and 20 mL of an aqueous saturated sodium chloride solution. After washing, the organic layer was dried with anhydrous magnesium sulfate. Concentration under reduced pressure afforded 1.77 g of the desired product (yield 91%).

$^1$H NMR (CDCl$_3$), (ppm): δ 1.27 (3H, t, J=7.1 Hz), 2.79-2.95 (2H, m), 3.24 (1H, brs), 4.19 (2H, q, J=7.1 Hz), 5.14 (1H, brs), 6.28 (1H, d, J=3.2 Hz), 6.33 (1H, d, J=1.7 Hz), 7.38 (1H, d, J=1.6 Hz).

Example 18

Preparation of ethyl 3-hydroxy-3-phenylbutanoate

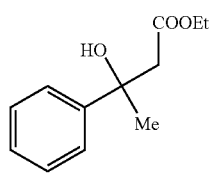

Under nitrogen atmosphere, 30 mL of THF was added to 3.96 g (6.50 mmol, 0.65 equivalent) of (BrZnCH$_2$COOEt.THF)$_2$. Under argon atmosphere, a solution of 1.20 g (10 mmol) of acetophenone in 5 mL of THF was added dropwise while stirring at 0~5° C. The mixture was stirred at 0~5° C. for 3 hours. 25 mL of 1N hydrochloric acid was added dropwise at 20° C. or lower, followed by dilution with 50 mL of ethyl acetate. Then, the layers were separated. The organic layer was washed successively with 10 mL (×2) of hydrochloric acid, 20 mL of an aqueous saturated sodium chloride solution, 20 mL (×2) of an aqueous saturated sodium bicarbonate solution, and 20 mL of an aqueous saturated sodium chloride solution. The organic layer was dried with anhydrous magnesium sulfate. Concentration under reduced pressure afforded 1.99 g of the desired product (yield 96%).

$^1$H NMR (CDCl$_3$), (ppm): δ 1.13 (3H, t, J=7.1 Hz), 1.54 (3H, s), 2.88 (2H, dd, J=56.7, 15.9 Hz), 4.06 (2H, q, J=7.1 Hz), 4.37 (1H, s), 7.20-7.47 (5H, m).

Example 19

Preparation of ethyl(1-hydroxycyclohexyl)acetate

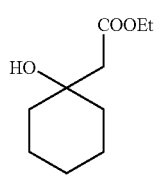

Under nitrogen atmosphere, 30 mL of THF was added to 6.09 g (10 mmol, 1.0 equivalent) of (BrZnCH$_2$COOEt.THF)$_2$. Under argon atmosphere, a solution of 0.98 g (10 mmol) of cyclohexanone in 5 mL of THF was added dropwise while stirring at 0~5° C. The mixture was stirred at 20~25° C. for 3 hours. 15 mL of 1N hydrochloric acid was added dropwise at 20° C. or lower, followed by dilution with 50 mL of ethyl acetate. Then, the layers were separated. The organic layer was washed successively with 10 mL (×2) of 1N hydrochloric acid, 10 mL of an aqueous saturated sodium chloride solution, 20 mL (×2) of an aqueous saturated sodium bicarbonate solution, and 10 mL (×2) of an aqueous saturated sodium chloride solution. After washing, the organic layer was dried with anhydrous magnesium sulfate. Concentration under reduced pressure afforded 1.76 g of the desired product (yield 95%).

$^1$H NMR (CDCl$_3$), (ppm): δ 1.28 (3H, t, J=7.1 Hz), 1.38-1.74 (10H, m), 2.46 (2H, s), 3.40 (1H, s), 4.17 (2H, q, J=7.1Hz).

Example 20

Preparation of ethyl(1-hydroxycyclopentyl)acetate

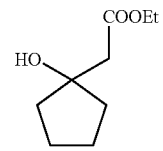

Under nitrogen atmosphere 30 mL of THF was added to 6.09 g (10 mmol, 1.0 equivalent) of BrZnCH$_2$COOEt.THF)$_2$. Under argon atmosphere, a solution of 0.84 g (10 mmol) of cyclopentanone in 5 mL of THF was added dropwise while stirring at 0~5° C. The mixture was stirred at 20~25° C. for 3 hours. 15 mL of 1N hydrochloric acid was added dropwise at 20° C. or lower, followed by dilution with 50 mL of ethyl acetate. Then, the layers were separated. The organic layer was washed successively with 10 mL (×2) of 1N hydrochloric acid, 10 mL of an aqueous saturated sodium chloride solution, 20 mL (×2) of an aqueous saturated sodium bicarbonate solution, and 10 mL (×2) of an aqueous saturated sodium chloride solution. After washing, the organic layer was dried with anhydrous magnesium sulfate. Concentration under reduced pressure afforded 1.73 g of the desired product (yield 94%).

$^1$H NMR (CDCl$_3$), (ppm): δ 1.28 (3H, t, J=7.1 Hz), 1.54-1.68 (4H, m), 1.77-1.89 (4H, m), 2.60 (2H, s), 3.37 (1H, s), 4.18 (2H, q, J=7.1 Hz).

Example 21

Preparation of ethyl(1-hydroxycyclohex-2-en-1-yl)acetate

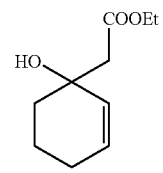

Under nitrogen atmosphere, 30 mL of THF was added to 6.09 g (10 mmol, 1.0 equivalent) of (BrZnCH$_2$COOEt.THF)$_2$. Under argon atmosphere, a solution of 0.96 g (10 mmol) of 2-cyclohexen-1-one in 5 mL of THF was added dropwise while stirring at 0~5° C. The mixture was stirred at 0~5° C. for 3 hours. 15 mL of 1N hydrochloric acid was added dropwise at 20° C. or lower, followed by dilution with 50 mL of ethyl acetate. Then, the layers were separated. The organic layer was washed successively with 10 mL (×2) of 1N hydrochloric acid, 10 mL of an aqueous saturated sodium chloride solution, 20 mL (×2) of an aqueous saturated sodium bicarbonate solution, and 10 mL (×2) of an aqueous saturated sodium chloride solution. After washing, the organic layer was dried with anhydrous magnesium sulfate. Concentration under reduced pressure afforded 1.61 g of the desired product (yield 94%).

$^1$H NMR (CDCl$_3$), (ppm): δ 1.28 (3H, t, J=7.1 Hz), 1.60-2.05 (6H, m), 2.55 (2H, dd, J=19.3, 15.6 Hz), 3.57 (1H, s), 4.19 (2H, q, J=7.1 Hz), 5.67 (1H, d, J=10.0 Hz), 5.80-5.86 (1H, m).

Example 22

Preparation of ethyl(4E)-3-hydroxy-3,5-diphenylpent-4-enoate

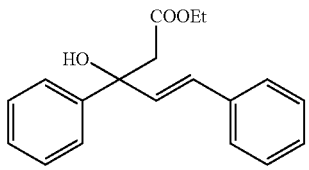

Under nitrogen atmosphere, 15 mL of THF was added to 3.05 g mmol, 1.0 equivalent) of (BrZnCH$_2$COOEt.THF)$_2$. Under argon atmosphere, a solution of 1.04 g (5 mmol) of (E)-chalcone in 2.5 mL of THF was added dropwise while stirring at 0~5° C. The mixture was stirred at 0~5° C. for 3 hours. 7.5 mL of 1N hydrochloric acid was added dropwise at 20° C. or lower, followed by dilution with 25 mL of ethyl acetate. Then, the layers were separated. The organic layer was washed successively with 5 mL (×2) of 1N hydrochloric acid, 5 mL of an aqueous saturated sodium chloride solution, 10 mL (×2) of an aqueous saturated sodium bicarbonate solution, and 5 mL (×2) of an aqueous saturated sodium chloride solution. After washing, the organic layer was dried with anhydrous magnesium sulfate. Concentration under reduced pressure afforded 1.44 g of the desired product (yield 97%).

$^1$H NMR (CDCl$_3$), (ppm): δ 1.17 (3H, t, J=7.1 Hz), 3.04 (2H, dd, 22.8, 15.7 Hz), 4.11 (2H, q, J=7.1 Hz), 4.81 (1H, s), 6.42 (1H, d, J=16.0 Hz), 6.66 (1H, d J=16.0 Hz), 7.25-7.53 (10H, m).

Example 23

Preparation of ethyl 3-hydroxy-3-phenylhex-4-enoate

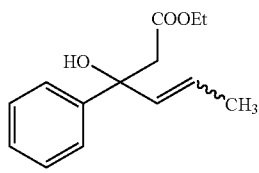

Under nitrogen atmosphere, 15 mL of THF was added to 3.05 g (5 mmol, 1.0 equivalent) of (BrZnCH$_2$COOEt.THF)$_2$. Under argon atmosphere, a solution of 0.73 g (5 mmol) of phenyl propenyl ketone in 2.5 mL of THF was added dropwise while stirring at 0~5° C. The mixture was stirred at 20~25° C. for 3 hours. 7.5 mL of 1N hydrochloric acid was added dropwise at 20° C. or lower, followed by dilution with 25 mL of ethyl acetate. Then, the layers were separated. The organic layer was washed successively with 5 mL (×2) of 1N hydrochloric acid, 5 mL of water, 10 mL (×2) of an aqueous saturated sodium bicarbonate solution, and 5 mL (×2) of an aqueous saturated sodium chloride solution. After washing, the organic layer was dried with anhydrous magnesium sulfate. After concentration under reduced pressure, purification with silica gel column (developing solvent; ethyl acetate/n-hexane=1/3) afforded 1.09 g of the desired product (yield 93%).

$^1$H NMR (CDCl$_3$), (ppm): δ 1.16 (3H, t, J=7.1 Hz), 1.69 (3H, d, J=5.2 Hz), 2.91 (2H, dd, J=24.2, 15.8 Hz), 4.09 (2H, q, J=7.1 Hz), 5.60-5.76 (2H, m), 7.23-7.46 (5H, m).

Example 24

Preparation of diethyl(2E)-4-hydroxy-4-phenylhex-2-enedioate

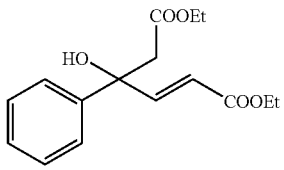

Under nitrogen atmosphere, 15 mL of THF was added to 3.05 g (5 mmol, 1.0 equivalent) of (BrZnCH$_2$COOEt.THF)$_2$. Under argon atmosphere, a solution of 1.02 g (5 mmol) of trans-ethyl 3-benzoylacrylate in 2.5 mL of THF was added dropwise while stirring at 0~5° C. The mixture was stirred at 20~25° C. for 3 hours. 7.5 mL of 1N hydrochloric acid was added dropwise at 20° C. or lower, followed by dilution with 25 mL of ethyl acetate. Then, the layers were separated. The organic layer was washed successively with 5 mL (×2) of 1N hydrochloric acid, 5 mL of water, 10 mL (×2) of an aqueous saturated sodium bicarbonate solution, and 5 mL (×2) of an aqueous saturated sodium chloride solution. After washing, the organic layer was dried with anhydrous magnesium sulfate. Concentration under reduced pressure afforded 1.42 g of the desired product (yield 97%).

$^1$H NMR (CDCl$_3$), (ppm): δ 1.18 (3H, t, J=7.1 Hz), 1.26 (3H, t, J=7.1 Hz), 2.99 (2H, dd, J=36.0, 16.1 Hz), 4.08-4.20 (4H, m), 4.84 (1H, s), 6.14 (1H, d, J=15.5 Hz), 7.06 (1H, d, J=15.5 Hz), 7.23-7.46 (5H, m).

Example 25

Preparation of ethyl(4E)-3-hydroxy-3-methyl-5-phenylpent-4-enoate

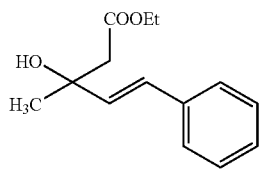

Under nitrogen atmosphere, 15 mL of THF was added to 3.05 g (5 mmol, 1.0 equivalent) of (BrZnCH$_2$COOEt.THF)$_2$. Under argon atmosphere, a solution of 0.73 g (5 mmol) of trans-4-phenyl-3-buten-2-one in 2.5 mL of THF was added dropwise while stirring at 0~5° C. The mixture was stirred at 20~25° C. for 3 hours. 8.5 mL of 1N hydrochloric acid was added dropwise at 20° C. or lower, followed by dilution with 25 mL of ethyl acetate. Then, the layers were separated. The organic layer was washed successively with 5 mL (×2) of 1N hydrochloric acid, 5 mL of water, 10 mL (×2) of an aqueous saturated sodium bicarbonate solution, and 5 mL (×2) of an aqueous saturated sodium chloride solution. After washing, the organic layer was dried with anhydrous magnesium sulfate. Concentration under reduced pressure afforded 1.17 g of the desired product (yield 100%).

$^1$H NMR (CDCl$_3$), (ppm): δ 1.23 (3H, t, J=7.1 Hz), 1.42 (3H, s), 2.66 (2H ,dd, J=19.5, 15.6 Hz), 4.05 (1H, s), 4.15 (2H, q, J=7.1 Hz), 6.27 (1H, d, J=16.0 Hz), 6.64 (1H, d, J=16.0 Hz), 7.20-7.39 (5H, m).

Example 26

Preparation of ethyl(4E)-3-hydroxy-3-pentylhex-4-enoate

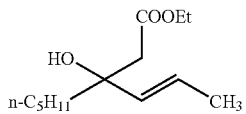

Under nitrogen atmosphere, 15 mL of. THF was added to 3.05 g (5 mmol, 1.0 equivalent) of (BrZnCH$_2$COOEt.THF)$_2$. Under argon atmosphere, a solution of 0.70 g (5 mmol) of trans-3-nonen-2-one in 2.5 mL of THF was added dropwise while stirring at 0~5° C. The mixture was stirred at 20~25° C. for 3 hours. 8.5 mL of 1N hydrochloric acid was added dropwise at 20° C. or lower, followed by dilution with 25 mL of ethyl acetate. Then, the layers were separated. The organic layer was washed successively with 5 mL (×2) of 1N hydrochloric acid, 5 mL of water, 10 mL (×2) of an aqueous saturated sodium bicarbonate solution, and 5 mL (×2) of an aqueous saturated sodium chloride solution. After washing, the organic layer was dried with anhydrous magnesium sulfate. Concentration under reduced pressure afforded 1.13 g of the desired product (yield 99%).

$^1$H NMR (CDCl$_3$), (ppm): δ 0.88 (3H, t, J=6.8 Hz), 1.23-1.40 (12H, m), 2.00 (2H, q, J=7.7 Hz), 2.54 (2H, dd, J=18.7, 15.5 Hz), 3.84 (1H, s), 4.15 (2H, q, J=7.1 Hz), 5.49-5.71 (2H, m).

Example 27

Preparation of ethyl(1-hydroxycyclohex-2-en-1-yl)acetate

Under nitrogen atmosphere, 20 mL of toluene was added to 3.05 g (5 mmol, 1.0 equivalent) of (BrZnCH$_2$COOEt.THF)$_2$. Under argon atmosphere, a solution of 0.48 g (5 mmol) of 2-cyclohexen-1-one in 5 mL of toluene was added dropwise while stirring at 0~5° C. The mixture was stirred at 0~5° C. for 3 hours. 10 mL of 1N hydrochloric acid was added dropwise at 20° C. or lower, followed by dilution with 25 mL of ethyl acetate. Then, the layers were separated. The organic layer was washed successively with 5 mL (×2) of 1N hydrochloric acid, 5 mL (×2) of an aqueous saturated sodium bicarbonate solution, and 10 mL (×2) of an aqueous saturated sodium chloride solution. After washing, the organic layer was dried with anhydrous magnesium sulfate. Concentration under reduced pressure afforded 0.87 g of the desired product (yield 95%).

$^1$N NMR was consistent with the compound obtained in Example 21.

Example 28

Preparation of ethyl(1-hydroxycyclohex-2-en-1-yl)acetate

Under nitrogen atmosphere, 20 mL of ethyl acetate was added to 3.05 g (5 mmol, 1.0 equivalent) of (BrZnCH$_2$COOEt.THF)$_2$. Under argon atmosphere, a solution of 0.48 g (5 mmol) of 2-cyclohexen-1-one in 5 mL of ethyl acetate was added dropwise while stirring at 0~5° C. The mixture was stirred at 0~5° C. for 3 hours. 10 mL of 1N hydrochloric acid was added dropwise at 20° C. or lower, followed by dilution with 25 mL of ethyl acetate. Then, the layers were separated. The organic layer was washed successively with 5 mL (×2) of 1N hydrochloric acid, 5 mL (×2) of an aqueous saturated sodium chloride solution, 10 mL (×2) of an aqueous saturated sodium bicarbonate solution, and 10 mL of an aqueous saturated sodium chloride solution. After washing, the organic layer was dried with anhydrous magnesium sulfate. Concentration under reduced pressure afforded 0.80 g of the desired product (yield 87%).

$^1$H NMR was consistent with the compound obtained in Example 21.

Example 29

Preparation of ethyl 3-oxo-3-phenylpropanoate

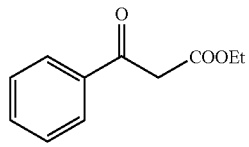

Under nitrogen atmosphere, 30 mL of THF was added to 12.2 g (20 mmol, 4.0 equivalent) of (BrZnCH$_2$COOEt.THF)$_2$. Under argon atmosphere, a solution of 1.03 g (5 mmol) of benzonitrile in 2.5 mL of THF was added dropwise while stirring at 0~5° C. The mixture was stirred at 20~25° C. for 27 hours. 15 mL of 10% hydrochloric acid was added dropwise at 20° C. or lower, and the mixture was stirred at 20~25° C., followed by dilution with 50 mL of ethyl acetate. Then, the layers were separated. The organic layer was washed successively with 15 mL of 1N hydrochloric acid, 20 mL of an aqueous saturated sodium chloride solution, 20 mL (×3) of an aqueous saturated sodium bicarbonate solution, and 20 mL of an aqueous saturated sodium chloride solution. After washing, the organic layer was dried with anhydrous magnesium sulfate. Concentration under reduced pressure afforded 1.64 g of the desired product (yield 85%).

$^1$H NMR (CDCl$_3$), (ppm): δ [1.26 (t, J=7.1 Hz), 1.34 (t, J=7.1Hz)] (3H), [3.99 (s), 5.67 (s), 12.6 (s)] (2H), 4.18-4.31 (2H, m), 7.44-7.96 (5H, m).

Example 30

Preparation of ethyl 3-(4-methylphenyl)-3-oxopropanoate

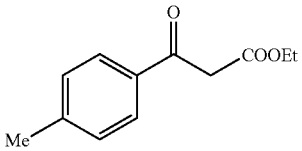

Under nitrogen atmosphere, 30 mL of THF was added to 6.09 g (10 mmol, 1.0 equivlanet) of (BrZnCH$_2$COOEt.THF)$_2$. Under argon atmosphere, a solution of 1.17 g (10 mmol) of p-tolunitrile in 5 mL of THF was added dropwise while stirring at 0~5° C. The mixture was stirred 20~25° C. for 46 hours. 15 mL of 10% hydrochloric acid was added dropwise at 20° C. or lower, and the mixture was stirred at 20~25° C. for 1 hour, followed by dilution with 50 mL of ethyl acetate. Then, the layers were separated. The organic layer was washed successively with 15 mL of 1N hydrochloric acid, 20 mL of an aqueous saturated sodium chloride solution, 20 mL (×2) of an aqueous saturated sodium bicarbonate solution and 20 mL of an aqueous saturated sodium chloride solution. After washing, the organic layer was dried with anhydrous magnesium sulfate. Concentration under reduced pressure afforded 1.88 g of the desired product (yield 91%).

$^1$H NMR (CDCl$_3$), (ppm): δ [1.25 (t, J=7.1 Hz), 1.33 (t, J=7.1 Hz)] (3H), [2.39 (s), 2.42 (s)] (3H), [3.96 (s), 5.63 (s), 12.6 (s)] (2H), 4.17-4.24 (2H, m), 7.20-7.86 (4H, m).

Example 31

Preparation of ethyl 3-(4-methoxyphenyl)-3-oxopropanoate

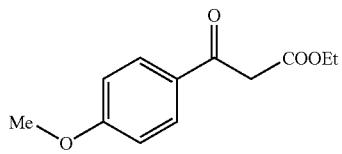

Under nitrogen atmosphere, 30 mL of THF was added to 6.09 g (10 mmol, 1.0 equivalent) of (BrZnCH$_2$COOEt.THF)$_2$. Under argon atmosphere, a solution of 1.33 g (10 mmol) of anisonitrile in 5 mL of THF was added dropwise while stirring at 0~5° C. The mixture was stirred at 20~25° C. for 92 hours. 15 mL of 10% hydrochloric acid was added dropwise at 20° C. or lower, and the mixture was stirred at 20~25° C. for 1 hour and 35 minutes, followed by dilution with 50 mL of ethyl acetate. Then, the layers were separated. The organic layer was washed successively with 15 mL of 1N hydrochloric acid, 20 mL of an aqueous saturated sodium chloride solution, 20 mL (×2) of an aqueous saturated sodium bicarbonate solution, and 20 mL of an aqueous saturated sodium chloride solution. After washing, the organic layer was dried with anhydrous magnesium sulfate. Concentration under reduced pressure afforded 2.08 g of the desired product (yield 94%).

$^1$H NMR (CDCl$_3$), (ppm): δ [1.25 (t, J=7.1 Hz), 1.33 (t, J=7.1 Hz)] (3H), 3.87 (3H, s), [3.94 (s), 5.58 (s), 12.6 (s)] (2H), 4.17-4.24 (2H, m), 6.94 (d, 2H, J=8.8 Hz), 7.93 (d, 2H, J=8.8 Hz).

Example 32

Preparation of ethyl 3-(4-fluorophenyl)-3-oxopropanoate

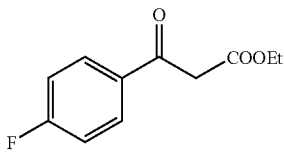

Under nitrogen atmosphere, 30 mL of. THF was added to 6.09 g (10 mmol, 1.0 equivalent) of (BrZnCH$_2$COOEt.THF)$_2$. Under argon atmosphere, a solution of 1.21 g (10 mmol) of 4-fluorobenzonitrile in 5 mL of THF was added dropwise while stirring at 0~5° C. The mixture was stirred at 20~25° C. for 26 hours. 15 mL of 10% hydrochloric acid was added dropwise at 20° C. or lower, and the mixture was stirred at 20~25° C. for 1 hour, followed by dilution with ethyl acetate. Then, the layers were separated. The organic layer was washed successively with 15 mL of 1N hydrochloric acid, 20 mL of an aqueous saturated sodium chloride solution, 20 mL (×2) of an aqueous saturated sodium bicarbonate solution, and 20 mL of an aqueous saturated sodium chloride solution. After washing, the organic layer was dried with anhydrous magnesium sulfate. Concentration under reduced pressure afforded 1.96 g of the desired product (yield 93%).

$^1$H NMR (CDCl$_3$), (ppm): δ [1.26 (t, J=7.1 Hz), 1.34 (t, J=7.1 Hz)] (3H), [3.96 (s), 5.61 (s), 12.6 (s)] (2H), 4.18-4.25 (2H, m), 7.07-8.02 (4H, m).

Example 33

Preparation of ethyl 3-(2-fluorophenyl)-3-oxopropanoate

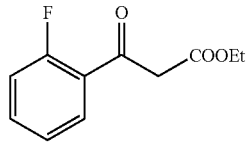

Under nitrogen atmosphere, 30 mL of THF was added to 6.09 g (10 mmol, 1.0 equivalent) of (BrZnCH$_2$COOEt.THF)$_2$. Under argon atmosphere, a solution of 1.21 g (10 mmol) of 2-fluorobenzonitrile in 5 mL of THF was added dropwise while stirring at 0~5° C. The mixture was stirred at 20° C.~25° C. for 46 hours. 15 mL of 10% hydrochloric acid added dropwise at 20° C. or lower, and the mixture was stirred at 20~25° C. for 1. hour, followed by dilution with 50 mL of ethyl acetate. Then, the layers were separated. The organic layer was washed successively with 15 mL of 1N hydrochloric acid, 20 mL of an aqueous saturated sodium chloride solution, 20 mL (×2) of an aqueous saturated sodium bicarbonate solution, and 20 mL of an aqueous saturated sodium chloride solution. After washing, the organic layer was dried with anhydrous magnesium sulfate. Concentration under reduced pressure afforded 1.94 g of the desired product (yield 92%).

$^1$H NMR (CDCl$_3$), (ppm): δ [1.26 (t, J=7.1 Hz), 1.34 (t, J=7.1 Hz)] (3H), [3.98 (s), 5.84 (s), 12.6 (s)] (2H), 4.17-4.28 (2H, m), 7.08-7.97 (4H, m).

Example 34

Preparation of ethyl 3-(4-nitrophenyl)-3-oxopropanoate

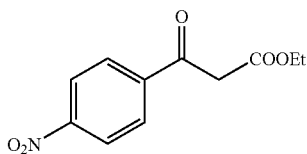

Under nitrogen atmosphere, 30 mL of THF was added to 6.09 g (10 mmol, 1.0 equivalent) of (BrZnCH$_2$COOEt.THF)$_2$. Under argon atmosphere, a solution of 1.48 g (10 mmol) of p-nitrobenzonitrile in 10 mL of THF was added dropwise while stirring at 0~5° C. The mixture was stirred at 20~25° C. for 21 hours. 15 mL of 10% hydrochloric acid was added dropwise at 20° C. or lower, and the mixture was stirred at 20~25° C. for 2 hours, followed by dilution with 50 mL of ethyl acetate. Then, the layers were separated. The organic layer was washed successively with 15 mL of 1N hydrochloric acid, 20 mL of an aqueous saturated sodium chloride solution, 20 mL (×2) of an aqueous saturated sodium bicarbonate solution, and 20 mL of an aqueous saturated sodium chloride solution. After washing, the organic layer was dried with anhydrous magnesium sulfate. After concentration under reduced pressure, crystals were loosened with n-hexane, filtered, and washed with n-hexane. After vacuum drying (40° C.), 2.09 g of the desired product was obtained (yield 88%).

$^1$H NMR (CDCl$_3$), (ppm): δ [1.26 (t, J=7.1 Hz), 1.35 (t, J=7.1 Hz)] (3H), [4.03 (s), 5.76 (s), 12.6 (s)] (2H), 4.19-4.34 (2H, m), 7.92-8.35 (4H, m).

Example 35

Preparation of ethyl(1-hydroxy-4-oxocyclohexa-2,5-dien-1-yl)acetate

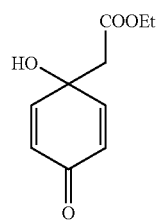

Under nitrogen atmosphere, 6 mL of THF was added to 1.22 g (2 mmol, 0.6 equivalent) of (BrZnCH$_2$COOEt.THF)$_2$. Under argon atmosphere, a solution of 0.36 g (3.33 mmol) of p-benzoquinone in 2.5 mL of THF was added dropwise while stirring at 0~5° C. The mixture was stirred at 20~25° C. for 1 hour. 5 mL of 1N hydrochloric acid was added dropwise at 20° C. or lower, followed by dilution with 25 mL of ethyl acetate. Then, the layers were separated. The organic layer was washed successively with 5 mL (×2) of 1N hydrochloric acid, 5 mL of water, 5 mL (×2) of an aqueous saturated sodium bicarbonate solution, and 5 mL (×2) of an aqueous saturated sodium chloride solution. After washing, the organic layer was dried with anhydrous magnesium sulfate. After concentration under reduced pressure, purification with silica gel column (developing solvent; ethyl acetate/n-hexane=1/3, 1/2) afforded 0.46 g of the desired product (yield 70%).

$^1$H NMR (CDCl$_3$), (ppm): δ 1.27 (3H, t, J-7.1 Hz), 2.70 (2H, s), 4.19 (2H, q, J=7.1 Hz), 4.36 (1H, s), 6.17 (2H, d, J=10.1 Hz), 6.98 (2H, d, J=10.1 Hz).

Example 36

Preparation of ethyl(1-hydroxy-2,5-dimethyl-4-oxocyclohexa-2,5-dien-1-yl)acetate

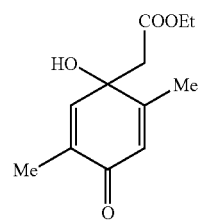

Under nitrogen atmosphere, 6 mL of THF was added to 1.22 g (2 mmol, 0.6 equivalent) of (BrZnCH$_2$COOEt.THF)$_2$. Under argon atmosphere, a solution of 0.45 g (3.33 mmol) of 2,5-dimethyl-p-benzoquinone in 3 mL of THF was added dropwise while stirring at. 0~5° C. The mixture was stirred at 20~25° C. for 1 hour. 5 mL of 1N hydrochloric acid was added dropwise at 20° C. or lower, followed by dilution with 25 mL of ethyl acetate. Then, the layers were separated. The organic layer was washed successively with 5 mL (×2) of 1N hydrochloric acid, 5 mL of water, 5 mL (×2) of an aqueous saturated sodium bicarbonate solution, and 5 mL (×2) of an aqueous saturated sodium chloride solution. After washing, the organic layer was dried with anhydrous magnesium sulfate. After concentration under reduced pressure, purification with silica gel column (developing solvent; ethyl acetate/n-hexane=1/3, 1/2) afforded 0.65 g of the desired product (yield 87%).

$^1$H NMR (CDCl$_3$), (ppm): δ 1.26 (3H, t, J=7.1 Hz), 1.88 (3H, d, J=1.4 Hz), 2.07 (3H, d, J=1.4 Hz), 2.48 (1H, d, J=15.4 Hz), 2.88 (1H, d, J=15.4 Hz), 3.76 (1H, s), 4.18 (2H, q, J=7.1 Hz), 6.06 (1H, d, J=1.3 Hz), 6.77 (1H, d, J=1.5 Hz).

Example 37

Preparation of ethyl(2,5-dichloro-1-hydroxy-4-oxocyclohexa-2,5-dien-1-yl)acetate

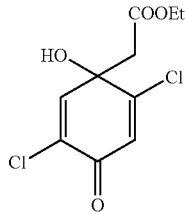

Under nitrogen atmosphere, 6 mL of THF was added to 1.22 g (2 mmol, 0.6 equivalent) of (BrZnCH$_2$COOEt.THF)$_2$. Under argon atmosphere, a solution of 0.59 g (3.33 mmol) of 2,5-dichloro-p-benzoquinone in 6.5 mL of THF was added dropwise while stirring at 0~5° C. The mixture was stirred at 20~25° C. 5 mL of 1N hydrochloric acid was added dropwise at 20° C. or lower, followed by dilution with 25 mL of ethyl acetate, and the layers were separated. The organic layer was washed successively with 5 mL (×2) of 1N hydrochloric acid, 5 mL of water, 5 mL (×2) of an aqueous saturated sodium bicarbonate solution, and 5 mL (2) of an aqueous saturated sodium chloride solution. After washing, the organic layer was dried with anhydrous magnesium sulfate. After concentration under reduced pressure, purification with silica gel column (developing solvent; ethyl acetate/n-hexane=1/3, 1/2) afforded 0.81 g of the desired product (yield 92%).

$^1$H NMR (CDCl$_3$), (ppm): δ 1.29 (3H, t, J=7.1 Hz), 2.71 (1H, d, J=16.1 Hz), 3.11 (1H, d, J=16.1 Hz), 4.23 (2H, q, J=7.1 Hz), 4.30 (1H, s), 6.54 (1H, s), 7.24 (1H, s).

Example 38

Preparation of ethyl(1-hydroxy-2,3,5,6-tetramethyl-4-oxocyclohexa-2,5-dien-1-yl)acetate

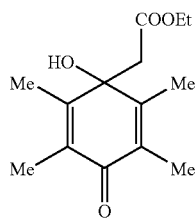

Under nitrogen atmosphere, 6 mL of THF was added to 1.22 g (2 mmol, 0.6 equivalent) of (BrZnCH$_2$COOEt.THF)$_2$. Under argon atmosphere, a solution of 0.45 g (3.33 mmol) of 2,3,5,6-tetramethyl-1,4-benzoquinone in 4 mL of THF was added dropwise while stirring at 0~5° C. The mixture was stirred at 20~25° C. for 1 hour. 5 mL of 1N hydrochloric acid was added dropwise at 20° C. or lower, followed by dilution with 25 mL of ethyl acetate. Then, the layers were separated. The organic layer was washed successively with 5 mL (×2) of 1N hydrochloric acid, 5 mL of water, 5 mL (×2) of an aqueous saturated sodium bicarbonate solution, and 5 mL (×2) of an aqueous saturated sodium chloride solution. After cooling, the organic layer was dried with anhydrous magnesium sulfate. Concentration under reduced pressure afforded 0.79 g of the desired product (yield 94%).

$^1$H NMR (CDCl$_3$), (ppm): δ 1.09 (3H, t, J=7.1 Hz), 1.84 (6H, d, J=0.9 Hz), 2.05 (6H, d, J=0.9 Hz), 2.76 (1H, s), 2.77 (2H, s), 3.96 (2H, q, J=7.1 Hz).

Example 39

Preparation of ethyl(2,3,5,6-tetrachloro-1-hydroxy-4-oxocyclohexa-2,5-dien-1-yl)acetate

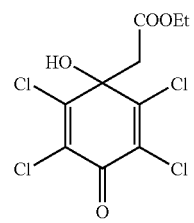

Under nitrogen atmosphere, 6 mL of THF was added to 1.22 g (2 mmol, 0.6 equivalent) of (BrZnCH$_2$COOEt.THF)$_2$. Under argon atmosphere, a solution of 0.82 g (3.33 mmol) of 2,3,5,6-tetrachloro-1,4-benzoquinone in 26 mL of THF was added dropwise while stirring at 0~5° C. The mixture was stirred at 20~25° C. for 1 hour. 10 mL of 1N hydrochloric acid was added dropwise at 20° C. or lower, followed by dilution with 50 mL of ethyl acetate. Then, the layers were separated. The organic layer was washed successively with 5 mL (×2) of 1N hydrochloric acid, 5 mL of water, 10 mL (×2) of an aqueous saturated sodium bicarbonate solution, and 5 mL (×2) of an aqueous saturated sodium chloride solution. After washing, the organic layer was dried with anhydrous magnesium sulfate. Concentration under reduced pressure afforded 1.04 g of the desired product (yield 94%).

$^1$H NMR (CDCl$_3$), (ppm): δ 1.22 (3H, t, J=7.2 Hz), 3.17 (2H, s), 4.13 (2H, q, J=7.2 Hz), 4.25 (1H, s).

Example 40

Preparation of ethyl(1-hydroxy-3,5-dimethyl-4-oxo-cyclohexa-2,5-dien-1-yl)acetate

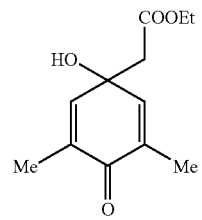

Under nitrogen atmosphere, 6 mL of. THF was added to 1.22 g (2 mmol, 0.6 equivalent) of (BrZnCH$_2$COOEt.THF)$_2$. Under argon atmosphere, a solution of 0.45 g (3.33 mmol) of 2,6-dimethyl-p-benzoquinone in 3 mL of THF was added dropwise while stirring at 0~5° C. The mixture was stirred at 20~25° C. for 1 hour. 5 mL of 1N hydrochloric acid was added dropwise at 20° C. or lower, followed by dilution with 25 mL of ethyl acetate. Then, the layers were separated. The organic layer was washed successively with 5 mL (×2) of 1N hydrochloric acid, 5 mL of water, 10 mL (×2) of an aqueous saturated sodium bicarbonate solution, and 5 mL (×2) of an aqueous saturated sodium chloride solution. After washing, the organic layer was dried with anhydrous magnesium sulfate. After concentration under reduced pressure, purification with silica gel column (developing solvent; ethyl acetate/n-hexane=1/3) afforded 0.60 g of the desired product (yield 80%).

$^1$H NMR (CDCl$_3$), (ppm): δ 1.28 (3H, t, J=7.2 Hz), 1.89 (6H, s), 2.64 (2H, s), 3.87 (1H, s), 4.22 (2H, q, J=7.1 Hz), 6.68 (2H, s).

Example 41

Preparation of ethyl(3,5-dichloro-1-hydroxy-4-oxo-cyclohexa-2,5-dien-1-yl)acetate

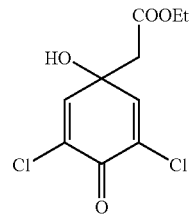

Under, nitrogen atmosphere, 6 mL of THF was added to 1.22 g (2 mmol, 0.6 equivalent) of (BrZnCH$_2$COOEt.THF)$_2$.

A solution of 0.59 g (3.33 mmol) of 2,6-dichloro-p-benzoquinone in 3 mL of THF was added dropwise while stirring at 0~5° C. The mixture was stirred at 20~25° C. for 1 hour. 5 mL of 1N hydrochloric acid was added dropwise at 20° C. or lower, followed by dilution with 25 mL of ethyl acetate. Then, the layers were separated. The organic layer was washed successively with 5 mL (×2) of 1N hydrochloric acid, 5 mL of water, 10 mL (×2) of an aqueous saturated sodium bicarbonate solution, and 5 mL (×2) of an aqueous saturated sodium chloride solution. After washing, the organic layer was dried with anhydrous magnesium sulfate. After concentration under reduced pressure, purification with silica gel column (developing solvent; ethyl acetate/n-hexane=1/3) afforded 0.76 g of the desired product (NMR yield 74%; internal standard trioxane). As a purified product, 0.48 g of the desired product was obtained (yield 54%).

$^1$H NMR (CDCl$_3$), (ppm): δ 1.31 (3H, t, J=7.2 Hz), 2.77 (2H, s), 4.21-4.29 (3H, m), 7.15 (2H, s).

Example 42

Preparation of diethyl(1,4-dihydroxycyclohexa-2,5-din-1,4-yl)diacetate

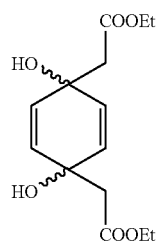

Under nitrogen atmosphere, 15 mL of THF was added to 3.05 g (5 mmol, 1.5 equivalent) of (BrZnCH$_2$COOEt.THF)$_2$. Under argon atmosphere, a solution of 0.36 g (3.33 mmol) of p-benzoquinone in 2.5 mL of THF was added dropwise while stirring at 0~5° C. The mixture was stirred at 20~25° C. for 3 hours. 7.5 mL of 1N hydrochloric acid was added dropwise at 20° C. or lower, followed by dilution with 25 mL of ethyl acetate. Then, the layers were separated. The organic layer was washed successively with 5 mL (×2) of 1N hydrochloric acid, 5 mL of water, 10 mL (×2) of an aqueous saturated sodium bicarbonate solution, and 5 mL (×2) of an aqueous saturated sodium chloride solution. After washing, the organic layer was dried with anhydrous magnesium sulfate. After concentration under reduced pressure, purification with silica gel column (developing solvent; ethyl acetate/n-hexane=1/1) afforded 0.62 g of the desired product (yield 66%).

$^1$H NMR (CDCl$_3$), (ppm): δ 1.26 (6H, t, J=7.1 Hz), 2.66 (4H, s), 3.49 (2H, s), 4.15 (4H, q, J=7.1 Hz), 5.97 (4H, s).

$^1$H NMR (CDCl$_3$), (ppm): δ 1.27 (6H, t, J=7.1 Hz), 2.55 (4H, s), 3.58 (2H, s), 4.17 (4H, q, J=7.1 Hz), 5.96 (4H, s).

(a cis compound and a trans compound were isolated, and measured by $^1$H NMR)

Example 43

Preparation of Solution of Ethyl Bromozincacetale in Tetrahydrofuran

Under argon atmosphere, 10 L of THF and 253. mL (2 mol) of chlorotrimethylsilane were added to 2616 g (40 gram atoms) of zinc powders. The mixture was stirred at 25° C. for 30 minutes. A solution of 2212 mL (20 mol) of ethyl bromoacetate in 25 L of THF was added dropwise at 25~35° C. The mixture was stirred at 31~35° C. for. 30 minutes. The solution was allowed to cool to 25° C., to obtain 37 L of an about 0.535 M solution of ethyl bromozincacetate in tetrahydrofuran.

Example 44

Preparation of ethyl(3S)-3-hydroxy-3-{6-[(methylamino)carbonyl]-2-naphthyl}-3-(1-trityl-1H-imidazol-4-yl)propanoate

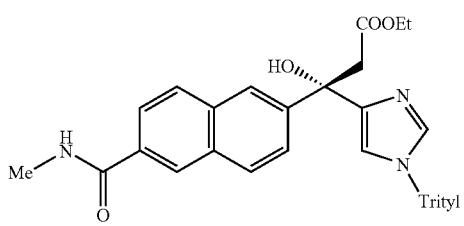

Under argon atmosphere, 21.2 g (72 mmol, 1.25 equivalent) of (+)-cinchonine was added to 431 mL (0.23 mol) of the solution of ethyl bromozincacetate in tetrahydrofuran obtained in Example 43 at 0~5° C. 18.6 mL (230 mmol, 4 equivalent) of pyridine was added dropwise at 0~5° C. over 7 minutes. The mixture was stirred at 0~5° C. for 20 minutes. A solution of 30 g (57.5 mmol) of N-methyl-6-[(1-trityl-1H-imidazol-4-yl)carbonyl]-2-naphthamide in 300 mL of THF was added dropwise at −42~−40° C. over 30 minutes. The mixture was stirred at −45~−40° C. for 1 hour. 430 mL of 1N hydrochloric acid was added dropwise, diluted with 430 mL of ethyl acetate, and the mixture was stirred at 20~25° C. for 30 minutes. After the layers were separated, the organic layer was washed successively with 290 mL of 1N hydrochloric acid, 290 mL of water, 290 mL (×2) of an aqueous saturated sodium bicarbonate solution, and 290 mL of an aqueous saturated sodium chloride solution. After washing and concentration under reduced pressure, to the concentration residue was added 90 mL of ethyl acetate, and this was warmed to 50° C. to dissolve it. The solution was stirred at 20~25° C. for 1 hour. 90 mL of IPE was added, and the mixture was stirred at, 0~5° C. for 2 hours. Crystals were filtered, and washed with 30 mL of IPE. After washing, vacuum drying (50° C.) to a constant weight afforded 29.2 g of ethyl (3S)-3-hydroxy-3-{6-[(methylamino)carbonyl]-2-naphthyl}-3-(1-trityl-1H-imidazol-4-yl)propanoate (yield 83%, enantiomer excess 93.5% ee).

$^1$H NMR (CDCl$_3$): δ 1.13 (3H, t, J=7.1 Hz), 3.05 (3H, d, J=4.8 Hz), 3.33 (2H, dd, J=98, 16 Hz), 4.04-4.13 (2H, m), 5.14 (1H, s), 6.35 (1H, brs), 6.84 (1H, d, J=1.5 Hz), 7.07-7.11 (6H, m), 7.26-7.38 (10H, m), 7.69-7.84 (4H, m), 8.03 (1H, s), 8.22 (1H, s).

Example 45

Preparation of ethyl(3S)-3-hydroxy-3-{6-[(methylamino)carbonyl]-2-naphthyl}-3-(1-trityl-1H-imidazol-4-yl)propanoate Under argon atmosphere, 0.37 g (1.25 mmol, 1.25 equivalent) of hydrocinchonine was added to 4.7 mL (2.5 mmol, 2.5 equivalent) of the solution of ethyl bromozincacetate in tetrahydrofuran obtained in Example 43 at 4~5° C. 0.32 mL (4 mmol, 4 equivalents) of pyridine was added dropwise at 5~6° C. The mixture was stirred at 3~6° C. for 20 minutes. A solution of 0.52 g (1 mmol) of N-methyl-6-[(1-trityl-1H-imidazol-4-yl)carbonyl]-2-naphthamide in 5.2 mL of THF was added dropwise at −36~−34° C. The mixture was stirred at −40~−34° C. for 1 hour and 15 minutes.

Further, 1.9 mL (1 mmol, 1 equivalent) of the solution of ethyl bromozincacetate in tetrahydrofuran obtained in Example 43 was added dropwise at −40~−35° C. The mixture was stirred at −40~−38° C. for 2 hours. 15 mL of 1N hydrochloric acid was added dropwise at 20° C. or lower, followed by dilution with 30 mL of ethyl acetate. Then, the layers were separated. The organic layer was washed successively with 5 mL (×2) of 1N hydrochloric acid, 5 mL of water, 5 mL (×2) of an aqueous saturated sodium bicarbonate solution, and 5 mL (×2) of an aqueous saturated sodium chloride solution. After concentration under reduced pressure, 5 mL of IPE was added to the concentration residue, this was recrystallized, crystals were filtered, and washed with 3 mL of IPE. After washing, vacuum drying (40° C.) to a constant weight afforded 0.49 g of ethyl(3S)-3-hydroxy-3-{6-[(methylamino)carbonyl]-2-naphthyl}-3-(1-trityl-1H-imidazol-4-yl)propanoate (yield 80%, enantiomer excess 90.9% ee).

$^1$H NMR was consistent with the compound obtained in Example 44.

Example 46

Preparation of ethyl 3-hydroxy-3-(1-trityl-1H-imidazol-4-yl)propanoate

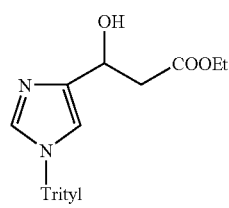

Under argon atmosphere, 5.6 mL (2.96 mmol, 1 equivalent) of the solution of ethyl bromozincacetate in tetrahydrofuran obtained in Example 43 was added dropwise to a solution of 1 g (2.96 mmol) of 1-trityl-1H-imidazol-4-carbaldehyde in 10 mL of THF at 3~6° C. The mixture was stirred at 0~5° C. for 1 hour and 25 minutes. 5.6 mL (2.96 mmol, 1 equivalent) of the solution of ethyl bromozincacetate in tetrahydrofuran obtained in Example 43 was added dropwise at 0~3° C. The mixture was stirred at 2~3° C. for 5 hours and 30 minutes. 5 mL of 1N hydrochloric acid was added dropwise at 20° C. or lower, followed by dilution with 30 mL of ethyl acetate. Then, the layers were separated. The organic layer was washed successively with 5 mL of 1N hydrochloric acid, 5 mL of water, 5 mL (×2) of an aqueous saturated sodium bicarbonate solution, and 5 mL (×2) of an aqueous saturated sodium chloride solution. After washing, the organic layer was dried with anhydrous magnesium sulfate. After concentration under reduced pressure, recrystallization with 3 mL of IPE afforded 1.16 g of the desired product (yield 92%).

$^1$H NMR (CDCl$_3$): δ 1.22 (3H, t, J=7.1 Hz), 2.83-2.86 (2H, m), 4.13 (2H, q, J=7.1 Hz), 5.09-5.13 (1H, m), 6.78 (1H, s), 7.10-7.15 (6H, m), 7.26-7.39 (10, m).

Example 47

Preparation of ethyl 3-hydroxy-3-(5-methyl-1-trityl-1H-imidazol-4-yl)propanoate

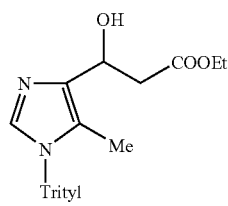

Under argon atmosphere, 3.2 mL (1.70 mmol, 2 equivalents) of the solution of ethyl bromozincacetate in tetrahydrofuran obtained in Example 43 was added dropwise to a solution of 0.3 g (0.85 mmol) of 5-methyl-1-trityl-1H-imidazol-4-carbaldehyde in 3 mL of THF at 4~7° C. The mixture was stirred at 2~5° C. for 2 hours. 5 mL of 1N hydrochloric acid was added dropwise at 20° C. or lower, followed by dilution with 15 mL of ethyl acetate. Then, the layers were separated. The organic layer was washed successively with 5 mL of 1N hydrochloric acid, 5 mL of water, 2.5 mL (×2) of an aqueous saturated sodium bicarbonate solution, and 2.5 mL (×2) of an aqueous saturated sodium chloride solution. After washing, the organic layer was dried with anhydrous magnesium sulfate. After concentration under reduced pressure, recrystallization with 3 mL of IPE afforded 0.30 g of the desired product (yield 80%).

$^1$H NMR (CDCl$_3$): δ 1.25 (3H, t, J=7.1 Hz), 1.47 (3H, s), 2.74-2.81 (1H, m), 2.98-3.06 (1H, m), 4.14 (2H, q, J=7.1 Hz), 5.02-5.06 (1H, m), 7.10-7.16 (6H, m), 7.30-7.33 (10, m).

Example 48

Preparation of ethyl 3-(3,5-di-tert-butyl-2-methoxyphenyl)-3-hydroxypropanoate

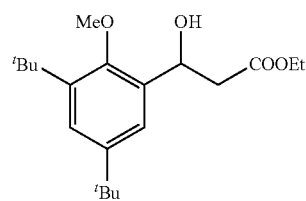

Under argon atmosphere, 7.5 mL (4.01 mmol, 2 equivalents) of the solution of ethyl bromozincacetate in terahydrofuran obtained in Example 43 was added dropwise to a solution of 0.5 g (2.01 mmol) of 3,5-di-tert-butyl-2-methoxybenzaldehyde in 5 mL of THF at 5~7° C. The mixture was stirred at 5~7° C. for 4 hours. 5 mL of 1N hydrochloric acid was added dropwise at 20° C. or lower, followed by dilution with 15 mL of ethyl acetate. Then, the layers were separated. The organic layer was washed successively with 5 mL (×2) of 1N hydrochloric acid, 5 mL of water, 5 mL (×2) of an aqueous saturated sodium bicarbonate solution, and 5 mL (×2) of an aqueous saturated sodium chloride solution. After washing, the organic layer was dried with anhydrous magnesium sulfate. After concentration under reduced pressure, crystals were loosened with 4 mL of n-hexane to obtain 0.58 g of the desired product (yield 86%).

$^1$H NMR (CDCl$_3$): δ 1.26-1.31 (12H, m), 1.39 (9H, s), 2.74-2.78 (2H, m), 3.26 (1H, d, J=3.2 Hz), 3.82 (3H, s), 4.21 (2H, q, J=7.1 Hz), 5.49-5.54 (1H, m), 7.30 (1H, d, J=2.5 Hz), 7.37 (1H, d, J=2.5 Hz).

Example 49

Preparation of ethyl 3-hydroxy-3-(6-methylpyridin-2-yl)propanoate

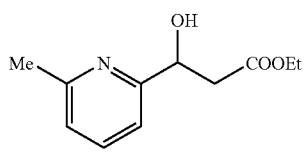

Under argon atmosphere, 30.9 mL (16.5 mmol, 2 equivalent) of the solution of ethyl bromozincacetate in tetrahydrofuran obtained in Example 43 was added dropwise to a solution of 1 g (8.25 mmol) of 2-methylpyridinecarboxyaldehyde in 10 mL of THF at 5~10° C. The mixture was stirred at 0~5° C. for 2 hours and 30 minutes. 10 mL of an aqueous saturated sodium bicarbonate solution was added dropwise at 20° C. or lower, followed by dilution with 30 mL of ethyl acetate. Then, insoluble materials were removed by filtration. The layers of the filtrate were separated, and the organic layer was washed successively with 10 mL (×3) of an aqueous saturated sodium bicarbonate solution, and 5 mL (×2) of an aqueous saturated chloride solution. After washing, the organic layer was dried with anhydrous magnesium sulfate. After concentration under reduced pressure, purification with silica gel column (developing solvent; ethyl acetate/n-hexane=1/3) afforded 1.48 g of the desired product (yield 86%).

$^1$H NMR (CDCl$_3$): δ 1.26 (3H, t, J=7.1 Hz), 2.54 (3H, s), 2.67-2.75 (1H, m), 2.82-2.89 (1H, m), 4.18 (2H, q, J=7.1 Hz), 4.49 (1H, d, J=5.5 Hz), 5.11-5.17 (1H, m), 7.06 (1H, d, J=7.6 Hz), 7.17 (1H, d, J=7.7 Hz), 7.58 (1H, d, J=7.7 Hz).

Example 50

Preparation of ethyl trifluoro-3-hydroxy-3-phenylbutanoate

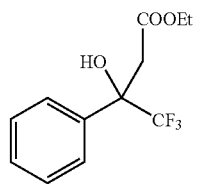

Under argon atmosphere, 20 mL (10.7 mmol, 2 equivalents) of the solution of ethyl bromozincacetate in tetrahydrofuran obtained in Example 43 was added dropwise to a solution of 0.75 mL (5.35 mmol) of trifluoroacetophenone in 2.75 mL of THF at 7~9° C. The mixture was stirred at 4~5° C. for 4 hours. 10 mL of 1N hydrochloric acid was added dropwise at 20° C. or lower, followed by dilution with 30 mL of ethyl acetate. Then, the layers were separated. The organic layer was washed successively with 5 mL (×2) of 1N hydrochloric acid, 5 mL of water, 5 mL (×2) of an aqueous saturated sodium bicarbonate solution, and 5 mL (×2) of an aqueous saturated sodium chloride solution. After washing, the organic layer was dried with anhydrous magnesium sulfate. Concentration under reduced pressure afforded 1.54 g of the desired product (NMR yield 97%; internal standard dioxane).

$^1$H NMR (CDCl$_3$): δ 1.16 (3H, t, J=7.1 Hz), 3.15 (2H, s), 4.07-4.15 (2H, m), 5.28 (1H, s), 7.36-7.43 (3H, m), 7.58-7.60 (2H, m).

Example 51

Preparation of ethyl 3-hydroxy-3-(2-methoxyphenyl)butanoate

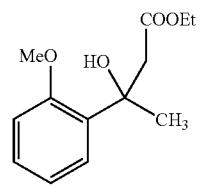

Under argon atmosphere, 20 mL (10.7 mmol, 2 equivalent) of the solution of ethyl bromozincacetate in tetrahydrofuran obtained in Example 43 was added dropwise to a solution of 0.74 mL (5.35 mmol) of o-methoxyacetophenone in 2.75 mL of THF at 7~10° C. The mixture was stirred at to 4~6° C. for 4 hours. 10 mL of 1N hydrochloric acid was added dropwise at 20° C. or lower, followed by dilution with 30 mL of ethyl acetate. Then, the layers were separated. The organic layer was washed successively with 5 mL (×2) of 1N hydrochloric acid, 5 mL of water, 5 mL (×2) of an aqueous saturated sodium bicarbonate solution, and 5 mL (×2) of an aqueous saturated sodium chloride solution. After washing, the organic layer was dried with anhydrous magnesium sulfate. Concentration under reduced pressure afforded 1.43 g of the desired product (NMR yield 96%; internal standard dioxane).

$^1$H NMR (CDCl$_3$): δ 1.07 (3H, t, J=7.1 Hz), 1.63 (3H, s), 2.86 (1H, d, J=15.0 Hz), 3.27 (1H, d, J=15.0 Hz), 3.86 (3H, s), 3.99 (2H, q, J=7.1 Hz), 4.54 (1H, s), 6.87-6.99 (2H, m), 7.21-7.27 (1H, m), 7.56-7.59 (1H, m).

Example 52

Preparation of ethyl 3-hydroxy-3-(2-methoxyphenyl)propanoate

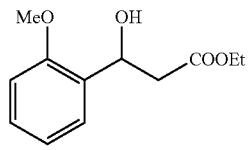

Under argon atmosphere, 20 mL (10.7 mmol, 2 equivalents) of the solution of ethyl bromozincacetate in tetrahydrofuran obtained in Example 43 was added dropwise to a solution of 0.65 mL (5.35 mmol) of o-methoxybenzaldehyde in 2.75 mL of THF at 5~10° C. The mixture was stirred at 5~7°

C. for 4 hours. 10 mL of 1N hydrochloric acid was added at 20° C. or lower, followed by dilution with 30 mL of ethyl acetate. Then, the layers were separated. The organic layer was washed successively with 5 mL (×2) of 1N hydrochloric acid, 5 mL of water, 5 mL (×2) of an aqueous saturated sodium bicarbonate solution, and 5 mL (×2) of an aqueous saturated sodium chloride solution. After washing, the organic layer was dried with anhydrous magnesium sulfate. Concentration under reduced pressure afforded 1.32 g of the desired produce (NMR yield 88%; internal standard trioxane).

$^1$H NMR (CDCl$_3$): δ 1.26 (3H, t, J=7.1 Hz), 2.66-2.86 (2H, m), 3.44-3.49 (1H, m), 3.85 (3H, s), 4.18 (2H, q, J=7.1 Hz), 5.33-5.39 (1H, m), 6.86-7.00 (1H, m), 7.23-7.29 (1H, m), 7.41-7.44 (1H, m).

Example 53

Preparation of ethyl 3-hydroxy-3-pyridin-2-ylpropanoate

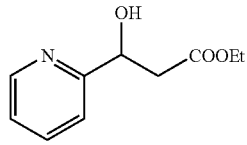

Under argon atmosphere, 39 mL (21 mmol, 2 equivalent) of the solution of ethyl bromozincacetate in tetrahydrofuran obtained in Example 43 was added dropwise to a solution of 1 mL (10.5 mmol) of 2-pyridinecarboxyaldehyde in 10 mL of THF at 5~12° C. The mixture was stirred at 5~10° C. for 3 hours. 15 mL of an aqueous saturated sodium bicarbonate solution was added dropwise at 20° C. or lower, followed by dilution with 30 mL of ethyl acetate. Then, insoluble materials were removed by filtration. The layers of the filtrate were separated and the organic layer was washed successively with 10 mL (×4) of an aqueous saturated sodium bicarbonate solution, and 10 mL (×2) of an aqueous saturated sodium chloride solution. After washing, the organic layer was dried with anhydrous magnesium sulfate. After concentration under reduced pressure, ethyl acetate was added, insoluble materials were filtered, and the filtrate was concentrated under reduced pressure to obtain 1.87 g of the desired product (NMR yield 83%; internal standard dioxane).

$^1$H NMR (CDCl$_3$): δ 1.25 (3H, t, J=7.1 Hz), 2.72-2.94 (2H, m), 4.14-4.30 (3H, m), 5.16-5.20 (1H, m), 7.19-7.27 (1H, m), 7.42 (1H, d, J=7.8 Hz), 7.68-7.73 (1H, m), 8.55 (1H, d, J=4.7 Hz).

Example 54

Preparation of ethyl 3-hydoxy-3-quinolin-2-ylpropanoate

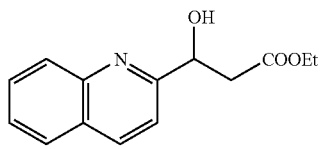

Under argon atmosphere, 23.8 mL (12.7 mmol, 2 equivalent) of the solution of ethyl bromozincacetate in tetrahydrofuran obtained in Example 43 was added dropwise to a solution of 1 g (6.36 mmol) of 2-quinolinecarboxyaldehyde in 10 mL of THF at 7~11° C. The mixture was stirred at 0~5° C. for 2 hours and 30 minutes. 10 mL of an aqueous saturated sodium bicarbonate solution was added dropwise at 20° C. or lower, followed by dilution with 30 mL of ethyl acetate. Then, insoluble materials were removed by filtration. The layers of the filtrate were separated, and the organic layer was washed successively with 10 mL (×2) of an aqueous saturated sodium bicarbonate solution, and 10 mL (×2) of an aqueous saturated sodium chloride solution. After washing, the organic layer was dried with anhydrous magnesium sulfate. Concentration under reduced pressure afforded 1.70 g of the desired product (NMR yield 74%; internal standard trioxane).

$^1$H NMR (CDCl$_3$): δ 1.25 (3H, t, J=7.1 Hz), 2.78-2.86 (1H, m), 2.94-3.00 (1H, m), 4.20 (2H, q, J=7.1 Hz), 4.86 (1H, d, J=5.3 Hz), 5.32-5.38 (1H, m), 7.48-7.57 (2H, m), 7.70-7.75 (1H, m), 7.80-7.84 (1H, m), 8.06 (1H, d, J=8.5 Hz), 8.18 (1H, d, J=8.5Hz).

Example 55

Preparation of Solution of Methyl Bromozincacetate in Tetrahydrofuran

Under argon atmosphere, 16 mL of THF and 0.24 mL (1.92 mmol) of chlorotrimethylsilane were added to 4.18 g (0.064 gram atoms) of zinc powders. The mixture was stirred at 26° C. for 30 minutes. A solution of 3.14 mL (32 mmol) of methyl bromoacetate in 40 mL of THF was added dropwise at 26~45° C. The mixture was stirred at 30~45° C. for 50 minutes. This was allowed to cool to 25° C., to obtain 59 mL of an about 0.530 M solution of methyl bromozincacetate in tetrahydrofuran.

Example 56

Preparation of methyl(3S)-3-hydroxy-3-{6-[(methylamino)carbonyl]-2-naphthyl}-3-(1-trityl-1H-imidazol-4-yl)propanoate

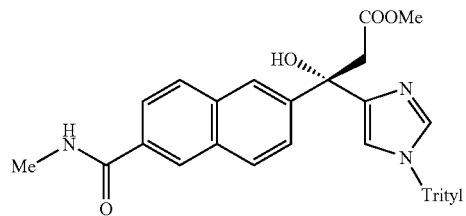

Under argon atmosphere, 0.49 g (1.66 mmol, 1.25 equivalents) of (+)-cinchonine was added to 10 mL (5.4 mmol) of the solution of methyl bromozincacetate in tetrahydrofuran obtained in Example 55 at 5~8° C. 0.43 mL (5.32 mmol, 4 equivalents) of pyridine was added dropwise at 6~8° C. The mixture was stirred at 4~6° C. for 20 minutes.

A solution of 0.69 g (1.32 mmol) of N-methyl-6-[(1-trityl-1H-imidazol-4-yl)carbonyl]-2-naphthamide in 6.9 mL of THF was added dropwise at −35~−40° C. The mixture was stirred at −40~−35° C. for 1 hour. 2.5 mL (1.32 mmol) of the solution of methyl bromozincacetate in tetrahydrofuran obtained in Example 55 was added dropwise at −40° C., and the mixture was stirred at −40~−35° C. for 1 hour. 20 mL of 1N hydrochloric acid was added dropwise at 0° C. or lower, followed by dilution with 30 mL of ethyl acetate. The layers were separated. The organic layer was washed successively with 5 mL of 1N hydrochloric acid, 5 mL of water, 5 mL (×2) of an aqueous saturated sodium bicarbonate solution, 5 mL of water, and 5 mL (×2) of an aqueous saturated sodium chloride solution. After washing and concentration under reduced pressure, 4 mL of IPE was added, crystals were loosened, filtered, and washed with 1 mL (×2) of IPE. After washing, vacuum drying (40° C.) to a constant weight afforded 0.72 g of methyl (3S)-3-hydroxy-3-{6-[(methylamino)carbonyl]-2-naphthyl}-3-(1-trityl-1H-imidazol-4-yl)propanoate (yield 92%, enantiomer excess 93.6% ee).

$^1$H NMR (CDCl$_3$): δ 3.05 (3H, d, J=4.9 Hz), 3.34 (2H, dd, J=108, 16.1 Hz), 3.62 (3H, s), 5.09 (1H, s), 6.37 (1H, d, J=4.6 Hz), 6.84 (1H, d, J=1.5 Hz), 7.05-7.10 (5H, m), 7.26-7.31 (10H, m), 7.39 (1H, d, J=1.2 Hz), 7.67-7.84 (4H, m), 8.01 (1H, s), 8.22 (1H, s).

Example 57

Preparation of Solution of N-Propyl Bromozincacetate in Tetrahydrofuran

Under argon atmosphere, 16 mL of THF and 0.24 mL (1.92 mmol) of chlorotrimethylsilane were added to 4.18 g (0.064, gram atoms) of zinc powders. The mixture was stirred at 23~25° C. for 30 minutes. A solution of 4.14 mL (32 mmol) of n-propyl bromoacetate in 40 mL of THF was added dropwise at 23~36° C. The mixture was stirred at 25~35° C. for 30 minutes. This was allowed to cool to 25° C., to obtain 60 mL of an about 0.530 M solution of n-propyl bromozincacetate in tetrahydrofuran.

Example 58

Preparation of n-propyl(3S)-3-hydroxy-3-{6-[(methylamino)carbonyl]-2-naphthyl}-3-(1-trityl-1H-imidazol-4-yl)propanoate

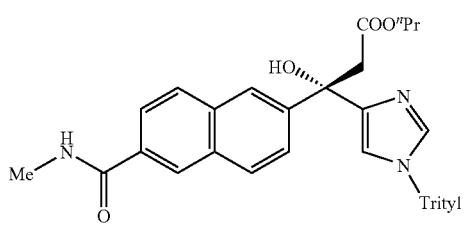

Under argon atmosphere, 0.49 g (1.66 mmol, 1.25 equivalents) of (+)-cichonine was added to 6.2 mL (3.3 mmol, 2.5 equivalents) of the solution of n-propyl bromozincacetate in tetrahydrofuran obtained in Example 57 at 3~4° C. 0.43 mL (5.32 mmol, 4 equivalents) of pyridine was added dropwise at 4~6° C. The mixture was stirred at 3~5° C. for 20 minutes. A solution of 0.69 g (1.32 mmol) of N-methyl-6-[(1-trityl-1H-imidazol-4-yl)carbonyl]-2-naphthamide in 6.9 mL of THF was added dropwise at −41~−35° C. 2.5 mL (1.32 mmol, 1 equivalent) of the solution of n-propyl bromozincacetate in tetrahydrofuran obtained in Example 57 was added at −43~−36° C., and the mixture was stirred at −43~−37° C. for 2 hours. 10 mL of 1N hydrochloric acid was added at 0° C. or lower, followed by dilution with 30 mL of ethyl acetate. The layers were separated. The organic layer was washed successively. with 5 mL (×3) of 1N hydrochloric acid, 5 mL of water, 5 mL (×2) of an aqueous saturated sodium bicarbonate solution, 5 mL (×2) of an aqueous saturated sodium chloride solution. After washing and concentration under reduced pressure, 2 mL of IPE was added, crystals were loosened, filtered, and washed with 1 mL (×2) of IPE. After washing, vacuum drying (4° C.) to a constant weight afforded 0.73 g of n-propyl (3S)-3-hydroxy-3-{6-[(methylamino)carbonyl]-2-naphthyl}-3-(1-trityl-1H-imidazol-4-yl)propanoate (yield 89%, enantiomer excessive rate 96.0% ee).

$^1$H NMR (DMSO-d$_6$): δ 0.66 (3H, t, J=7.4 Hz), 1.28-1.39 (2H, m), 2.84 (3H, d, J=4.4 Hz), 3.33 (2H, q, J=7.2 Hz), 3.79 (2H, t, J=6.5 Hz), 5.99 (1H, brs), 6.88 (1H, s), 7.05-7.08 (6H, m), 7.83-7.43 (9H, m), 7.70-7.73 (1H, m), 7.87-7.96 (3H, m), 8.01 (1H, s), 8.36 (1H, s), 8.56 (1H, d, J=4.6 Hz).

Example 59

Preparation of Solution of tert-butyl bromozincacetate in tetrahydrofuran

Under argon atmosphere, 20 mL of THF and 0.5 mL (3.9 mmol) of chlorotrimethylsilane were added to 5.2 g (0.08 gram atoms) of zinc powders. The mixture was stirred at 23~25° C. for 20 minutes. A solution of 5.9 mL (0.04 mol) of tert-butyl bromoacetate in 50 mL of THF was added dropwise at 24~42° C. The mixture was stirred at 42~45° C. for 20 minutes. This was allowed to cool to 25° C., to obtain 76 mL of an about 0.52 M solution of tert-butyl bromozincacetate in tetrahydrofuran.

Example 60

Preparation of tert-butyl 3-hydroxy-3-(1-trityl-1H-imidazol-4-yl)propanoate

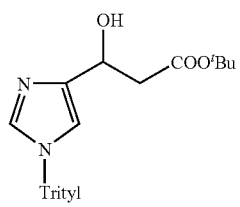

Under argon atmosphere, 8.5 mL (4.43 mmol, 1.5 equivalents) of the solution of tert-butyl bromozincacetate in tetrahydrofuran obtained in Example 59 was added dropwise to a solution of 1 g (2.96 mmol) of 1-trityl-1H-imidazol-5-carbaldehyde in 10 mL of THF at 5~9° C. The mixture was stirred at 2~5° C. for 3 hours and 30 minutes. 10 mL of 1N hydrochloric acid was added dropwise at 20° C. or lower, followed by dilution with 15 mL of ethyl acetate. Then, the layers were separated. The organic layer was washed successively with 5 mL of 1N hydrochloric acid, 5 mL of water, 5 mL (×2) of an aqueous saturated sodium bicarbonate solution, and 5 mL (×2) of an aqueous saturated sodium chloride solution. After washing, the organic layer was dried with anhydrous magnesium sulfate. Concentration under reduced pressure, the residue was loosened with 7 mL of IPE, filtered and washed with 7 mL of IPE. After washing, vacuum drying (40° C.) to a constant weight afforded 1.15 g of the desired product (yield 86%).

¹H NMR (CDCl₃): δ 1.42 (9H, s), 2.70-2.85 (2H, m), 3.52 (1H, d, J=4.8 Hz), 5.03-5.09 (1H, m), 6.79 (1H, s), 7.09-7.15 (6H, m), 7.30-7.38 (10H, m).

Example 61

Preparation of Solution of 2-bromozinc-γ-butyrolactone in tetrahydrofuran

Under argon atmosphere, 40 mL of tetrahydrofuran and 1 mL (0.96 mmol) of chlorotrimethylsilane were added to 10.45 g (0.16 gram atoms) of zinc powders, and the mixture was stirred at 23~25° C. for 20 minutes. A solution of 7.4 mL (0.08 mol) of 2-bromo-γ-butyrolactone in 100 mL of tetrahydrofuran was added dropwise at 24~35° C. The mixture was stirred at 28~35° C. for 20 minutes. This was allowed to cool to 25° C., to obtain 148 mL of an about 0.539 M solution of 2-buromozinc-γ-butyrolactone in tetrahydrofuran.

Example 62

Preparation of 3-(1-hydroxy-1-phenylethyl)dihydrofuran-2-(3H)-one

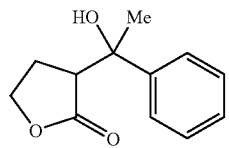

Under argon atmosphere, 39.7 mL (4.43 mmol, 1.5 equivalents) of the solution of 2-bromozinc-γ-butyrolactone in tetrahydrofuran obtained in Example 61 was added dropwise to a solution of 1.25 mL (10.7 mmol) of acetophenone in 10 mL of THF at 6~8° C. The mixture was stirred at 4~6° C. for 4 hours. 15 mL of 1N hydrochloric acid was added dropwise at 20° C. or lower, followed by dilution with 50 mL of ethyl acetate. Then, the layers were separated. The organic layer was washed successively with 10 mL of 1N hydrochloric acid, 10 mL of water, 20 ml, 15 mL and 10 mL of an aqueous saturated sodium bicarbonate solution, and 10 mL (×2) of an aqueous saturated sodium chloride solution. After washing, the organic layer was dried with anhydrous magnesium sulfate. After concentration under reduced pressure, purification with silica gel column (developing solvent; ethyl acetate/n-hexane=1/3, 1/2, 1/1) afforded 1.88 g of the desired product (NMR yield 62.5%; internal standard dioxane). 0.92 g of the desired product was obtained as crystals (yield 42%).

¹H NMR (CDCl₃): δ 1.38 (3H, s), 1.97-2.13 (2H, m), 2.96-3.04 (2H, m), 4.05-4.19 (2H, m), 7.24-7.44 (5H, m).

Example 63

Preparation of Solution of (−)-menthyl bromozincacetate in tetrahydrofuran

Under argon atmosphere, 20 mL of tetrahydrofuran and 0.5 mL (0.48 mmol) of chlorotrimethylsilane were added to 5.23 g (0.08 gram atoms) of zinc powders, and the mixture was stirred at 22° C. for 20 minutes. 50 mL of a solution of 11.09 g (0.04 mol) of (−)-menthyl bromoacetate in tetrahydrofuran was added dropwise at 22~35° C. The mixture was stirred at 25~33° C. for 30 minutes. This was allowed to cool to 25° C., to obtain 80 mL of an about 0.491 M solution of (−)-menthyl bromozincacetate in tetrahydrofuran.

Example 64

Preparation of (1R,2S,5R)-2-isopropyl-5-methylcyclohexyl 3-hydroxy-3-phenylbutanoate

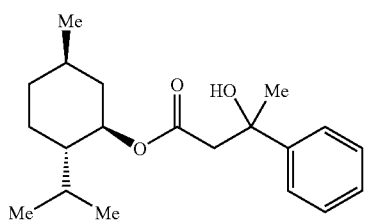

20.4 mL (20 mmol, 2 equivalents) of the solution of (−)-menthyl bromozincacetate in tetrahydrofuran obtained in Example 63 was added dropwise to a solution of 0.58 mL (5 mmol) of acetophenone in 3 mL of THF at 5~7° C. The mixture was stirred at 3~7° C. for 4 hours. 10 mL of 1H hydrochloric acid was added at 20° C. or lower, followed by dilution with 20 mL of ethyl acetate. Then, the layers were separated. The organic layer was washed successively with 5 mL of 1N hydrochloric acid, 5 mL of water, 10 mL and 5 mL of an aqueous saturated sodium bicarbonate solution, and 5 mL (×2) of an aqueous saturated sodium chloride solution. After washing, the organic layer was dried with anhydrous magnesium sulfate. After concentration under reduced pressure, purification with silica gel column (developing solvent; ethyl acetate/n-hexane=1/5, 1/3) afforded 1.69 g of the desired product (NMR yield 92%; internal standard dioxane). Recrystallization with n-hexane afforded 0.74 g of the desired product (yield 47%).

¹H NMR (CDCl₃): δ 0.67-0.96 (10H, m), 1.34-1.86 (9H, m), 2.87 (2H, dd, J=61.9, 15.6 Hz), 4.53-4.65 (2H, m), 7.21-7.33 (3H, m), 7.43-7.45 (2H, m).

Example 65

Preparation of Solution of ethyl bromozincacetate in cyclopentyl methyl ether

Under argon atmosphere, 38 mL of cyclopentyl methyl ether and 1.9 mL (15 mmol) of chlorotrimethylsilane were added to 19.6 g (0.3 gram atoms) of zinc powders, and the mixture was stirred for 20 minutes. A solution of 16.6 mL (0.15 mol) of ethyl bromoacetate in 94 mL of cyclopentyl methyl ether was added dropwise at 30~40° C. for 40 minutes. The mixture was stirred at the same temperature for 30 minutes. This was allowed to cool 25° C., to obtain 150 mL of an about 1.0 M solution of ethyl bromozincacetate in cyclopentyl methyl ether.

Example 66

Preparation of ethyl(3S)-3-hydroxy-3-{6-[(methylamino)carbonyl]-2-naphthyl}-3-(1-trityl-1H-imidazol-4-yl)propanoate 75.0 mL (75.0 mmol) of the solution of ethyl bromozincacetate in cyclopentyl methyl ether obtained in Example 65 was added dropwise to 100 mL of THF at −15~−5° C. 11.0 g (37.5 mmol) of cinchonine was added at −15~−5° C., 9.7 mL (120 mmol) of pyridine was added dropwise, and the mixture was stirred for 20 minutes. 15.6 g (30.0 mmol) of N-methyl-6-[(1-trityl-1H-imidazol-4-yl)carbonyl]-2-naphthamide was added at once by assisting by 25 mL of flowing THF at −15~−5° C., and the mixture was stirred at the same temperature for 1 hour. 30.0 mL (30.0 mmol) of the solution of ethyl bromozincacetate in cyclopentyl methyl ether obtained in Example 65 was added dropwise at −15~−5° C. over 40 minutes, and the mixture was stirred at the same temperature for 1 hour. 420 mL of ethyl acetate and 210 mL of 1N hydrochloric acid were added in this order at −15~10° C., and the mixture was stirred at 15~25° C. for 30 minutes. The organic layer was washed with 210 mL of 1N hydrochloric acid, and further 210 mL (×3) of water, 210 mL (×2) of an aqueous saturated sodium bicarbonate solution, and 210 mL of water. After washing, the organic layer was concentrated to about 50 mL under heating and reduced pressure (inner temperature 20~40° C.). 50 mL of ethyl acetate was added, followed by re-concentration procedure two times. 50 mL of ethyl acetate was added to the residue, the mixture was stirred at room temperature for 1 hour, 50 mL of IPE was added, and the mixture was stirred at room temperature. After stirred at 0~10° C. for 1 hour, crystals were filtered, washed with 16 mL (×2) of IPE, and dried to obtain 17.0 g of ethyl (3S)-3-hydroxy-3-{6-[(methylamino)carbonyl]-2-naphthyl}-3-(1-trityl-1H-imidazol-4-yl)propanoate (yield 93%, enantiomer excess 94.3% ee).

$^1$H NMR was consistent with the compound obtained in Example 44.

Example 67

Preparation of Solution of ethyl bromozincacetate in 2-methyltetrahydrofuran

Under argon atmosphere, 40 mL of 2-methyltetrahydrofuran and 1 mL (0.96 mmol) of chlorotrimethylsilane were added to 10.45 g (0.16 gram atoms) of zinc powders, and the mixture was stirred at 23~25° C. for 20 minutes. A solution of 8.85 mL (0.08 mol) of ethyl bromoacetate in 100 mL of 2-methyltetrahydrofuran was added dropwise at 24~35° C. The mixture was stirred at 27~35° C. for 20 minutes. This was allowed to cool to 25° C., to obtain 150 mL of an about 0.535 M solution of ethyl bromozincacetate in 2-methyltetrahydrofuran.

Example 68

Preparation of ethyl 3-hydroxy-3-(1-trityl-1H-imidazol-4-yl)propanoate

Under argon atmosphere, 8.3 mL (4.43 mmol, 1.5 equivalent) of the solution of ethyl bromozincacetate in 2-methyltetrahydrofuran obtained in Example 67 was added dropwise to a solution of 1 g (2.96 mmol) of 1-trityl-1H-imidazol-4-carbaldehyde in 10 mL of THF at 5~8° C. The mixture was stirred at 3~6° C. for 2 hours and 20 minutes. The mixture was stirred at 20~25° C. for 1 hour and 15 minutes. 10 mL of 1N hydrochloric acid was added dropwise at 20° C. or lower, followed by dilution with 15 mL of ethyl acetate. Then, the layers were separated. The organic layer was washed successively with 5 mL (×2) of 1N hydrochloric acid, 5 mL of water, 5 mL (×2) of an aqueous saturated sodium bicarbonate solution, and 5 mL (×2) of an aqueous saturated sodium chloride solution. After washing, the organic layer was dried with anhydrous magnesium sulfate. After concentration under reduced pressure, recrystallization with 5 mL of IPE afforded 1.04 g of the desired product (yield 83%).

$^1$H NMR was consistent with the compound obtained in Example 46.

Example 69

Preparation of Solution of ethyl bromozincacetate in DME

Under argon atmosphere, 30 mL of DME and 0.41 mL (3.20 mmol) of chlorotrimethylsilane were added to 4.18 g (0.064 gram atoms) of zinc powders, and the mixture was stirred for 20 minutes. A solution of 3.54 mL (32.0 mmol) of ethyl bromoacetate in 26 mL of DME was added dropwise at 30~40° C. The mixture was stirred at the same temperature for 30 minutes. This was allowed to cool to 25° C., to obtain 60 mL of an about 0.533 M solution of ethyl bromozincacetate in DME.

Example 70

Asymmetric Reformatsky Reaction Using Solution of ethyl bromozincacetate in DME

Under argon atmosphere, 2.34 mL (1.25 mmol) of the solution of ethyl bromozincacetate in DME obtained in Example 69 was added dropwise to 2.0 mL of THF at 0~5° C. 184 mg (0.625 mmol) of cinchonine was added at 0~5° C., 162 μL (2.00 mmol) of pyridine was added dropwise, and the mixture was stirred for 20 minutes. 261 mg (0.500 mmol) of N-methyl-6-[(1-trityl-1H-imidazol-4-yl)carbonyl]-2-naphthamide was added at once at 0~5° C., and the mixture was stirred at the same temperature for 1 hour. 0.938 mL (0.500 mmol) of the solution of ethyl bromozincacetate in DME obtained in Example 69 was added dropwise at 0~5° C., the mixture was stirred at the same temperature for 1 hour, and this was analyzed by HPLC (reaction yield>99%, enantiomer excess 91.0% ee).

Example 71

Stability of ethyl bromozinacetate.THF Binuclear Complex Crystal (($BrZnCH_2COOEt.THF)_2$)

Under argon atmosphere, 100 mL of THF and 2.5 mL (19.7 mmol) of chlorotrimethylsilane were added to 26.1 g (0.4 gram atoms) of zinc powders, and the mixture was stirred at 20~25° C. for 30 minutes. A solution of 22.2 mL (0.2 mol) of ethyl bromoacetate in 250 mL of THF was added dropwise at 20~35° C. The mixture was stirred at 20~35° C. for 1 hour, and allowed to cool to 25° C. Under nitrogen atmosphere, zinc was removed by filtration, followed by washing with 50 mL of THF. The filtrate was stirred at room temperature for 30 minutes and at 0~5° C. for 1 hour (precipitation of crystals). The mixture was stored in a refrigerator overnight. Under nitrogen atmosphere, crystals were filtered, press-filtered with nitrogen, and dried until completion of removal of a liquid, to obtain 35.3 g of ethyl bromozincacetate.THF binuclear complex crystals.

The resulting ethyl bromozincacetate.THF binuclear complex crystals (($BrZnCH_2COOEt.THF)_2$) were stored in a refrigerator at 0~5° C. and 2025° C.

Immediately after, and 30 days, 60 days and 180 days after preparation of ethyl bromozinacetate.THF binuclear complex crystals(($BrZnCH_2COOEt.THF)_2$), $^1$H NMR measurements for the crystals were performed, and stability was assessed by a ratio of ethyl bromozincacetate.THF binuclear complex crystals and ethyl acetate produced by degradation (Table 4).

TABLE 4

Stability for Crystal of Ethyl Bromozincacetate•THF Binuclear Complex ((BrZnCH$_2$COOEt•THF)$_2$)

| Storing Temperature (° C.) | Storing Period (day) | (BrZnCH$_2$COOEt•THF)$_2$/ Ethyl Acetate (%) |
|---|---|---|
| 20~25 | 0 | 89 |
|  | 30 | 73 |
| 0~5 | 0 | 89 |
|  | 30 | 89 |
|  | 60 | 87 |
|  | 180 | 93 |

As seen from Table 4, when the ethyl bromozincacetate.THF binuclear complex crystals ((BrZnCH$_2$COOEt.THF)$_2$) prepared by the present method are stored at 0~5° C. under inert gas atmosphere, remarkable degradation was not observed even after 6 months.

Example 72

Stability of Solution of ethyl bromozincacetate in tetrahydrofuran

Under argon atmosphere, 80 mL of tetrahydrofuran and 2.0 mL (16 mmol) of chlorotrimethyl silane were added to 20.9 g (0.33 gram atoms) of zinc powders, and the mixture was stirred at room temperature for 30 minutes. A solution of 17.7 mL (0.16 mol) of ethyl bromoacetate in 200 mL of tetrahydrofuran was added dropwise at 25~35° C. The mixture was stirred at 25~35° C. for 30 minutes. This was allowed to cool to 25° C. to obtain 300 mL of an about 0.535 M solution of ethyl bromozincacetate in tetrahydrofuran.

The resulting solution of ethyl bromozincacetate in tetrahydrofuran was stored in an inert gas in sealed state, reacted with N,N-diisopropyl-6-[(1-trityl-1H-imidazol-4-yl)carbonyl]-2-naphthamide, and a reaction rate into ethyl 3-{6-[(diisopropylamino)carbonyl]-2-naphthyl}-3-hydroxy-3-(1-trityl-1H-imidazol-4-yl)propanoate was measured. The procedure was as follows: 1.55 g (2.55 mmol) of N,N-diisopropyl-6-[(1-trityl-1H-imidazol-4-yl)carbonyl]-2-naphthamide was dissolved in 9 mL of THF, 5 mL (2.55 mmol) of a solution of ethyl bromozincacetate in tetrahydrofuran was added dropwise at −42° C., the mixture was stirred at −48~−42° C. until completion of the reaction, and stability was assessed by HPLC analysis (Table 5). A reaction rate was calculated from an area percentage of HPLC.

Immediately after, and 30 days and 60 days after preparation of the solution of ethyl bromozincacetate in tetrahydrofuran, this reaction was performed.

The solution of ethyl bromozincacetate in tetrahydrofuran was stored in the refrigerator at 0~5° C. and 20~25° C. under nitrogen atmosphere.

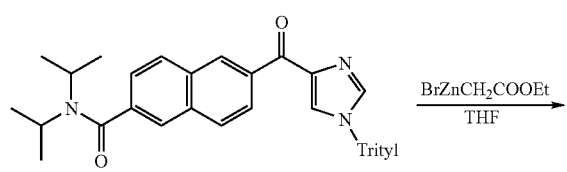

BrZnCH$_2$COOEt
THF

-continued

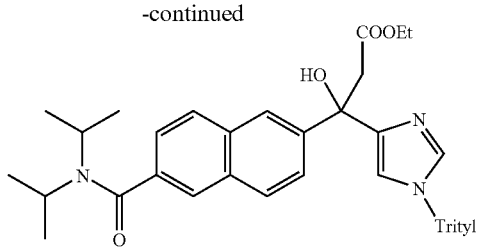

TABLE 5

Stability for Solution of Ethyl Bromozincacetate in Tetrahydrofuran

| Storing Temperature (° C.) | Storing Period (day) | Reaction Rate (%) |
|---|---|---|
| 20~25 | 0 | 83 |
|  | 30 | 17 |
|  | 60 | 0 |
| 0~5 | 0 | 83 |
|  | 30 | 76 |
|  | 60 | 76 |

HPLC Analysis Conditions
Column: L-column
Mobile phase: 0.05 M KH$_2$PO$_4$ aqueous solution:acetonitrile=30:70
Flow rate: 1.0 mL/min.
Detection: UV (254 nm)

As seen from Table 5, when the solution of ethyl bromozincacetate in THF prepared by the present method is stored at 0~5° C. under inert gas atmosphere, the solution exhibits a high reaction rate (76%) even after 2 months, and remarkable degradation was not observed.

Example 73

Stability of Solution of ethyl bromozincacetate in cyclopentyl methyl ether

Under argon atmosphere, 40 mL of cyclopentyl methyl ether and 0.51 mL (4 mmol) of chlorotrimethylsilane were added to 5.23 g (0.08 gram atoms) of zinc powders, and the mixture was stirred for 20 minutes. A solution of 4.42 mL (35 mmol) of ethyl bromoacetate in 35 mL of cyclopentyl methyl ether was added dropwise at 30~40° C. The mixture was stirred at the same temperature for 30 minutes. This was allowed to cool to 25° C., to obtain 80 mL of an about 0.5 M solution of ethyl bromozincacetate in cyclopentyl methyl ether. The resulting solution of ethyl bromozincacetate in cyclopentyl methyl ether was stored in an inert gas in sealed state, reacted with N-methyl-6-[(1-trityl-1H-imidazol-4-yl)carbonyl]-2-naphthamide, and a reaction rate into ethyl 3-hydroxy-3-{6-[(methylamino)carbonyl]-2-naphthyl}-3-(1-trityl-1H-imidazol-4-yl)propanoate was measured. The procedure was as follows: 261 mg (0.5 mmol) of N-methyl-6-[(1-trityl-1H-imidazol-4-yl)carbonyl]-2-naphthamide was dissolved in 5 mL of THF, 1 mL (0.5 mmol) of solution of ethyl bromozincacetate in cylopentyl methyl ether was added dropwise at 0~5° C., the mixture was stirred at 20~25° C. for 1 hour and stability was assessed by HPLC analysis (Table 6). A reaction rate was calculated from an area percentage of HPLC.

Immediately after, and 7 days and 30 days after preparation of the solution of ethyl bromozincacetate in cyclopentyl methyl ether, this reaction was performed. The solution of ethyl bromozincacetate in cyclopentyl methyl ether was stored in a refrigerator at 0~5° C. and 20~25° C. under nitrogen atmosphere.

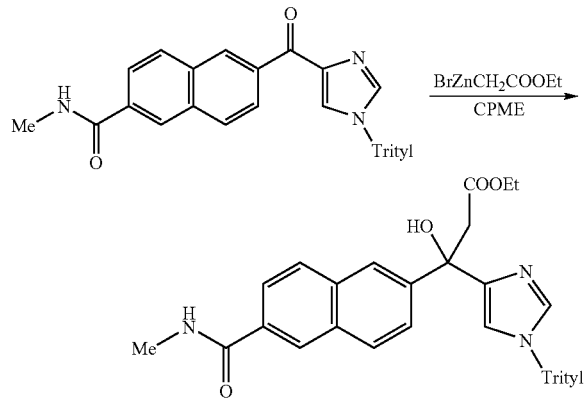

TABLE 6

Stability for Solution of Ethyl Bromozincacetate in Cyclopentyl Methyl Ether

| Storing Temperature (° C.) | Storing Period (day) | Reaction Rate (%) |
|---|---|---|
| 20~25 | 0 | 94 |
|  | 7 | 87 |
|  | 30 | 18 |
| 0~5 | 0 | 94 |
|  | 7 | 94 |
|  | 30 | 89 |

HPLC Analysis Conditions
  Column: Chiralcel OD-RH
  Mobile phase: 0.05 M potassium hexafluorophosphate aqueous solution:acetonitrile=55:45
  Flow rate: 1.0 mL/min.
  Detection: UV (254 nm)

As seen from Table 6, when the solution of ethyl bromozincacetate in cyclopentyl methyl ether prepared by the present method is stored at 0~5° C. under inert gas atmosphere, the solution exhibited a high reaction rate (89%) even after one month.

Example 74

Stability of Solution of ethyl bromozincacetate in DME

Under argon atmosphere, 30 mL of DME and 0.41 mL (3.20 mmol) of chlorotrimethylsilane were added to 4.18 g (0.064 gram atoms) of zinc powders and the mixture was stirred for 20 minutes. A solution of 3.54 mL (32.0 mmol) of ethyl bromoacetate in 26 mL of DME was added dropwise at 30~40° C. over 40 minutes. The mixture was stirred at the same temperature for 30 minutes. This was allowed to cool to 25° C., to obtain an about 0.533 M solution of ethyl bromozincacetate in DME. The solution of ethyl bromozincacetate in DME was stored in an inert gas in sealed state, reacted with N-methyl-6-[(1-trityl-1H-imidazol-4-yl)carbonyl]-2-naphthamide, and a reaction rate into ethyl 3-hydroxy-3-{6-[(methylamino)carbonyl]-2-naphthyl}-3-(1-trityl-1H-imidazol-4-yl)propanoate was measured. The procedure was as follows: 261 mg (0.5 mmol) of N-methyl-6-[(1-trityl-1H-imidazol-4-yl)carbonyl]-2-naphthamide was dissolved in 5 mL of THF, 0.938 mL (0.5 mmol) of a solution of ethyl bromozincacetate in DME was added dropwise at 0~5° C., the mixture was stirred at 20~25° C. for 1 hour, and stability was assessed by HPLC analysis (Table 7). A reaction rate was calculated from an area percentage of HPLC.

Immediately after, and 10 days and 30 days after preparation of the solution of ethyl bromozincacetate in DME, this reaction was performed.

The solution of ethyl bromozincacetate in DME was stored in a refrigerator at 0~5° C. and 20~25° C. under nitrogen atmosphere.

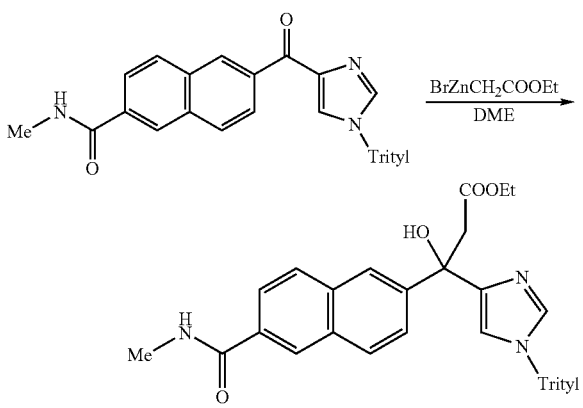

TABLE 7

Stability for Solution of Ethyl Bromozincacetate in DME

| Storing Temperature (° C.) | Storing Period (day) | Reaction Rate (%) |
|---|---|---|
| 20~25 | 0 | 90 |
|  | 10 | 55 |
|  | 30 | 0 |
| 0~5 | 0 | 90 |
|  | 10 | 84 |
|  | 30 | 68 |

HPLC Analysis Conditions
  Column: Chiralcel OD-RH
  Mobile phase: 0.05 M potassium hexafluorophosphate aqueous solution:acetonitrile=55:45
  Flow rate: 1.0 mL/min.
  Detection: UV (254 nm)

As seen from Table 7, when the solution of ethyl bromozincacetate in DME prepared by the present method is stored at 0~5° C. under inert gas atmosphere, the solution exhibited a high reaction rate (84%) even after 10 days.

Example 75

Stability of Solution of ethyl bromozincacetate in 2-methyltetrahydrofuran

Under argon atmosphere, 40 mL of 2-methyltetrahydrofuran and 1 mL (0.96 mmol) of chlorotrimethylsilane were added to 10.45 g (0.16 gram atoms) of zinc powders, and the mixture was stirred at 23 to 25° C. for 20 minutes. A solution of 8.85 mL (0.08 mol) of ethyl bromoacetate in 100 mL of 2-methyltetrahydrofuran was added dropwise at 24~35° C. The mixture was stirred at 27~35° C. for 20 minutes. This was allowed to cool to 25° C., to obtain 150 mL of an about 0.5M solution of ethyl bromozincacetate in 2-methyltetrahydrofuran. The resulting solution of ethyl bromozincacetate in 2-methyltetrahydrofuran was stored in an inert gas in sealed state, reacted with 1-trityl-1H-imidazol-4-carbaldehyde, ethyl 3-hydroxy-3-(1-trityl-1H-imidazol-4-yl)propanoate was isolated, and a remaining amount of ethyl bromozincacetate was obtained. The procedure was as follows: 1 g (2.96 mmol) of 1-trityl-1H-imidazol-4-carbaldehyde was dissolved in 10 mL of THF, 8.3 mL (4.34 mmol) of a solution of ethyl bromozincacetate in 2-methyltetrahydrofuran was added dorpwise at 0~5° C., and the mixture was stirred at 20~25° C. for 1 hour and 15 minutes. 10 mL of 1N hydrochloric acid was added dropwise at 20° C. or lower, followed by dilution with 15 mL of ethyl acetate. The layers were separated. The organic layer was washed successively with 5 mL (×2) of 1N hydrochloric acid, 5 mL of water, 5 mL (×2) of an aqueous saturated sodium bicarbonate solution, and 5 mL (×2) of an aqueous saturated sodium chloride solution. After washing, the organic layer was dried with anhydrous magnesium sulfate. After concentration under reduced pressure, recrystallization with 5 mL of IPE afforded the desired product, and stability was assessed (Table 8).

Immediately after, and 30 days after preparation of the solution of ethyl bromozincacetate in 2-methyltetrahydrofuran, this reaction was performed.

The solution of ethyl bromozincacetate in 2-methyltetrahydrofuran was stored in a refrigerator at 0~5° C. under nitrogen atmosphere.

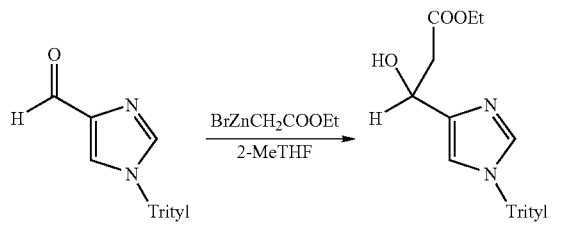

TABLE 8

| Stability for Solution of Ethyl Bromozincacetate in 2-Methyltetrahydrofuran | | |
|---|---|---|
| Storing Temperature (° C.) | Storing Period (day) | Isolation Yield (%) |
| 0~5 | 0 | 83 |
|  | 30 | 80 |

As seen from Table 8, when the solution of ethyl bromozincacetate in 2-methyltetrahydrofuran prepared by the present method is stored at 0~5° C. under inert gas atmosphere, the solution exhibited high reactivity (80%) even after one month.

INDUSTRIAL APPLICABILITY

As described above, according to the present invention, the steroid $C_{17,20}$ lyase inhibitor represented by the general formula (I) and an intermediate for preparing the same can be obtained by an industrial advantageous method, being very useful.

Further, the present invention can provide a Reformatsky reagent in a very stable form.

That is, the present invention provides a crystal of a Reformatsky reagent coordinated with THF $((BrZnCH_2COOC_2H_5 \cdot THF)_2)$. The Reformatsky reagent in this crystal form can be used as a reagent for at least 6 months without substantial manufacturing problem, by storing at a low temperature such as 0~5° C.

Also, the present invention provides a solution of a Reformatsky reagent $(BrZnCH_2COOC_2H_5)$ in THF, 1,2-dimethoxyethane or cyclopentyl methyl ether. The Reformatsky reagent in this solution form can be used as a reagent for at least 1 month without substantial manufacturing problem, by storing at a low temperature of around 0~5° C.

We claim:

1. A process for producing a compound represented by the Formula (II'):

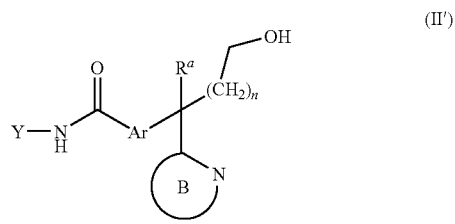

wherein $R^a$ is a hydrogen atom or a substituent, Ar is an aromatic hydrocarbon group which may have a substituent, Y is a hydrogen atom or a substituent, a ring B is a nitrogen-containing ring which may have a substituent, n is an integer of 1 to 3 or a salt thereof, which comprises reducing a compound represented by the Formula (III'):

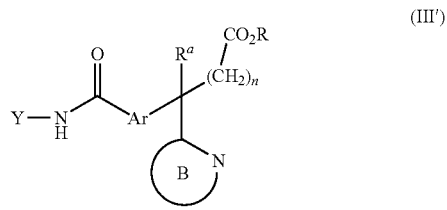

wherein R is an ester residue and each symbol is defined above or a salt thereof.

2. A process for producing a compound represented by the Formula (II):

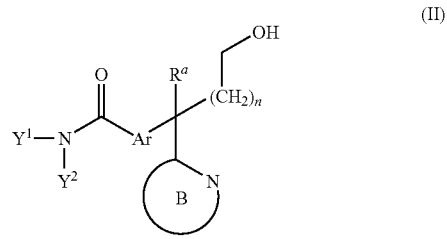

wherein $R^a$ is a hydrogen atom or a substituent, Ar is an aromatic hydrocarbon group which may have a substituent, $Y^1$ and $Y^2$ are, the same or different and independently, a hydrogen atom or a substituent, a ring B is a nitrogen-containing ring which may have a substituent, n is an integer of 1 to 3 or a salt thereof, which comprises reducing in the presence of a metal hydride complex and a metal halide compound a compound represented by the Formula (III):

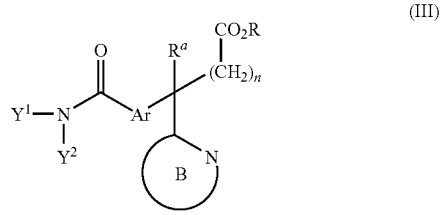

(III)

wherein R is an ester residue and each symbol is defined above or a salt thereof.

3. The process according to claim 1 or 2, wherein the Ring B is a heterocyclic ring which may have a substituent and one to three heteroatoms arbitrarily selected from a nitrogen atom, a sulfur atom, and an oxygen atom other than the nitrogen atom indicated in the formula.

4. A process for producing a compound represented by the Formula (IIa):

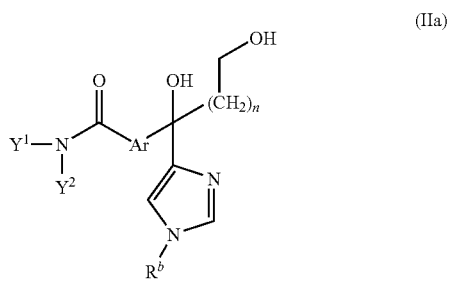

(IIa)

wherein Ar is an aromatic hydrocarbon group which may have a substituent, $Y^1$ and $Y^2$ are, the same or different and independently, a hydrogen atom or a substituent, $R^b$ is a protection group, n is an integer of 1 to 3 or a salt thereof, which comprises reducing a compound represented by the Formula (IIIa):

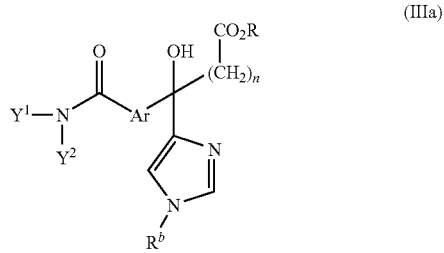

(IIIa)

wherein R is an ester residue and each symbol is defined above or a salt thereof in the presence of a metal hydride complex and a metal halide compound.

5. A process for producing a compound represented by the Formula (IIb):

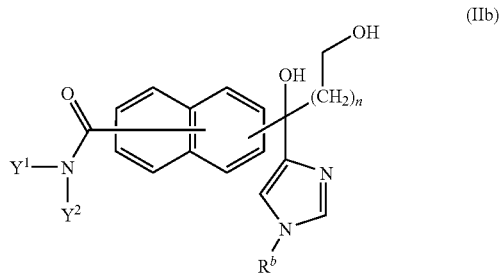

(IIb)

wherein $Y^1$ and $Y^2$ are, the same or different and independently, a hydrogen atom or a substituent, $R^b$ is a protection group, n is an integer of 1 to 3 or a salt thereof, which comprises reducing a compound represented by the Formula (IIIb):

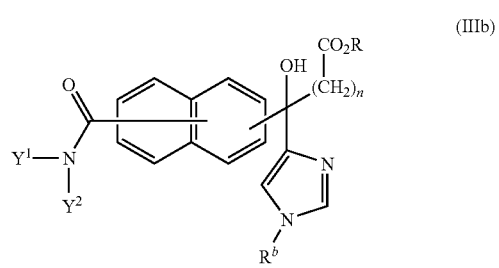

(IIIb)

wherein R is an ester residue and each symbol is defined above or a salt thereof in the presence of a metal hydride complex and a metal halide compound.

6. The process according to claim 2, wherein the metal hydride complex is an alkali metal hydride complex.

7. The process according to claim 6, wherein the alkali metal hydride complex is sodium borohydride.

8. The process according to claim 2, wherein the metal halide is a calcium halide.

9. The process according to claim 8, wherein the calcium halide is calcium chloride.

10. The process according to claim 1, wherein ether and alcohol are used as a solvent in a reduction reaction.

11. The process according to claim 10, which comprises adding alcohol to a reaction system in ether as a solvent.

12. The process according to claim 10 or 11, wherein the ether is a cyclic ether and the alcohol is $C_{1-6}$ alcohol.

13. The process according to claim 12, wherein the cyclic ether is tetrahydrofuran and the $C_{1-6}$ alcohol is ethanol or methanol.

14. A process for producing:
a compound represented by the Formula (II'):

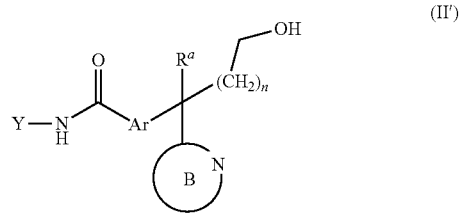

(II')

wherein $R^a$ is a hydrogen atom or a substituent, Ar is an aromatic hydrocarbon group which may have a substituent, Y is a hydrogen atom or a substituent, a ring B is a nitrogen-containing ring which may have a substituent, n is an integer of 1 to 3 or a salt thereof;

a compound represented by the Formula (II):

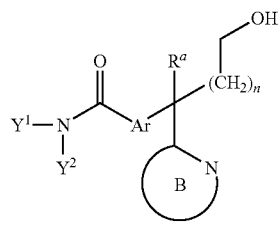

(II)

wherein $R^a$ is a hydrogen atom or a substituent, Ar is an aromatic hydrocarbon group which may have a substituent, $Y^1$ and $Y^2$ are, the same or different and independently, a hydrogen atom or a substituent, a ring B is a nitrogen-containing ring which may have a substituent, n is an integer of 1 to 3 or a salt thereof;

a compound represented by the Formula (IIa):

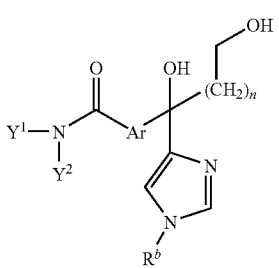

(IIa)

wherein Ar is an aromatic hydrocarbon group which may have a substituent, $Y^1$ and $Y^2$ are, the same or different and independently, a hydrogen atom or a substituent, $R^b$ is a protection group, n is an integer of 1 to 3 or a salt thereof;

or a compound represented by the Formula (IIb):

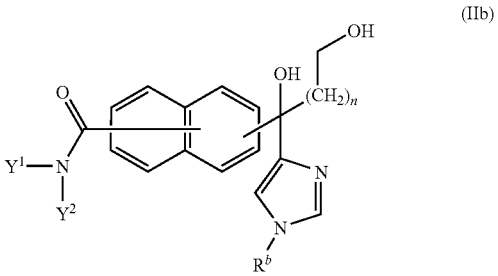

(IIb)

wherein $Y^1$ and $Y^2$ are, the same or different and independently, a hydrogen atom or a substituent, $R^b$ is a protection group, n is an integer of 1 to 3 or a salt thereof, which comprises selectively reducing (i) an esterified carboxyl group and (ii) an esterified carboxy group of a compound having an N-unsubstituted amino group or an N-monosubstituted amino group in an ether-alcohol solvent in the presence of metal hydride complex and a calcium halide.

15. The process according to claim 14, which comprises adding alcohol to a reaction system in ether as a solvent.

16. The process according to claim 14, wherein the metal hydride complex is an alkali metal hydride complex.

17. The process according to claim 14, wherein the calcium halide is calcium chloride.

18. The process according to claim 14, wherein the metal hydride complex is sodium borohydride, the calcium halide is calcium chloride, the ether is tetrahydrofuran, and the alcohol is ethanol or methanol.

\* \* \* \* \*